United States Patent [19]

Kishimoto et al.

[11] Patent Number: 4,921,851
[45] Date of Patent: May 1, 1990

[54] CEPHEM COMPOUNDS, THEIR PRODUCTION AND USE

[75] Inventors: Shoji Kishimoto, Hyogo; Kiminori Tomimatsu, Osaka; Akio Miyake, Osaka; Yoshinobu Yoshimura, Osaka, all of Japan

[73] Assignee: Takeda Chemical Industries, Ltd., Osaka, Japan

[21] Appl. No.: 396,758

[22] Filed: Aug. 22, 1989

Related U.S. Application Data

[63] Continuation of Ser. No. 309,952, Feb. 9, 1989, abandoned, which is a continuation of Ser. No. 59,952, Jun. 9, 1987, abandoned.

[30] Foreign Application Priority Data

Jun. 9, 1986 [JP] Japan ................... 61-133134
Jul. 10, 1986 [JP] Japan ................... 61-162610
Aug. 22, 1986 [JP] Japan ................... 61-197961
May 28, 1987 [JP] Japan ................... 62-132971

[51] Int. Cl.$^5$ .................... A61K 31/545; C07D 501/46
[52] U.S. Cl. ...................... 514/203; 514/202; 540/222; 540/225; 544/236
[58] Field of Search ............ 540/222, 225; 514/202, 514/203

[56] References Cited

U.S. PATENT DOCUMENTS

4,845,087 7/1989 Lattrell et al. .............. 540/222
4,864,022 9/1989 Miyake et al. ............... 540/222

FOREIGN PATENT DOCUMENTS

137441 4/1985 European Pat. Off. .
160252 11/1985 European Pat. Off. .
203271 12/1986 European Pat. Off. .

Primary Examiner—Donald G. Daus
Attorney, Agent, or Firm—Wegner & Bretschneider

[57] ABSTRACT

This invention relates to a compound of the formula:

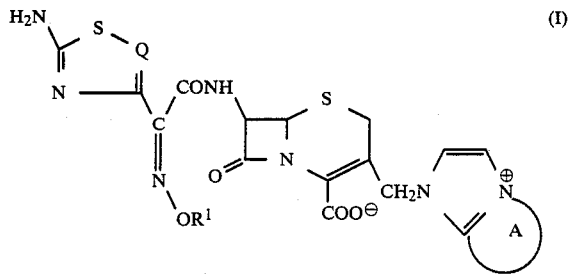

wherein Q is nitrogen or CH; $R^1$ is hydrogen or a lower alkyl group which may be substituted; and ring A is a pyridine or pyridazine ring which is substituted at the ring-constituting carbon atom by a group of the formula:

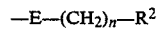

in which E is sulfur or NH; $R^2$ is an amino, carbamoylamino, formylamino, acetylamino, N-formimidoylamino, N-acetimidoylamino, lower alkylamino, hydroxyl or carbamoyloxy group; and n is an integer of 2 to 4, or a pharmaceutically acceptable salt thereof. The compound (I) or a pharmaceutically acceptable sale thereof has excellent antibacterial activity and is used as antibiotics.

8 Claims, No Drawings

CEPHEM COMPOUNDS, THEIR PRODUCTION AND USE

This application is a continuation of U.S. application Ser. No. 309,952 filed Feb. 9, 1989, which is a continuation of U.S. application Ser. No. 059,952 filed June 9, 1987 all abandoned.

The present invention relates to a novel cephem compound having excellent antibacterial activity.

More concretely, the present invention relates to a compound of the formula:

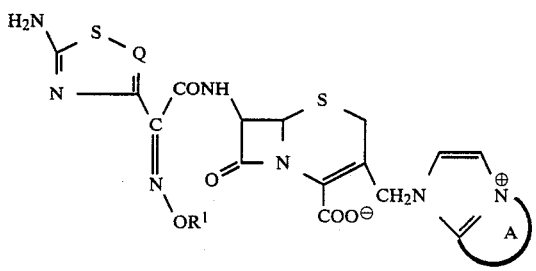

wherein Q is nitrogen or CH; $R^1$ is hydrogen or a lower alkyl group which may be substituted; and ring A is a pyridine or pyridazine ring which is substituted at the ring-constituting carbon atom by a group of the formula:

$$-E-(CH_2)_n-R^2$$

in which E is sulfur or NH; $R^2$ is an amino, carbamoylamino, formylamino, acetylamino, N-formimidoylamino, N-acetimidoylamino, lower alkylamino, hydroxyl or carbamoyloxy group; and n is an integer of 2 to 4, or a pharmaceutically acceptable salt thereof.

Cephem antibiotics have been widely used in the treatment of diseases caused by pathogenic bacteria in man and animals and are particularly useful for the treatment of diseases owing to bacteria which are resistant to penicillin antibiotics and for the treatment of penicillin-hypersensitive patients, for instance. In such applications, it is desirable to use a cephem antibiotic having activity against both of gram-positive and gram-negative bacteria and, for this reason, much research has hitherto been undertaken to find cephem antibiotics having a broad antibacterial spectrum. So far, several kinds of third-generation cephalosporin compounds have been launched into the market. However, the antibacterial activity of these compounds is not fully satisfactory and there remains yet to be developed a compound which is active against both of *Staphylococcus aureus* and *Pseudomonas aeruginosa* or a compound which is highly inhibitory to clinically isolated highly β-lactamase-producing strains of *Citrobacter freundii*, or *Enterobacter cloacae*. Therefore, there is a demand for the development of a compound having an extended antibacterial spectrum which covers gram-positive and gram-negative bacteria inclusive of such clinical isolates.

Hitherto a variety of cephem compounds each having a quaternary ammonium-methyl substituent at the 3-position and a 2-(2-aminothiazol-4-yl or 5-amino-1,2,4-thiadiazol-3-yl)-2-(optionally substituted hydroxy)iminoacetamido substituent at the 7-position have been synthesized and some patent applications have been reported (e.g. DE-OLS No. 2,715,385; U.S. Pat. Nos. 4,278,793; 4,258,041; U.K. Patent No. 2,098,216; EP-A-27599; EP-A-111934).

However, these cephem compounds mostly contain at the 3-position a moncyclic pyridinium group.

Furthermore, for example, EP-A-62321 describes cephem compounds of the formula:

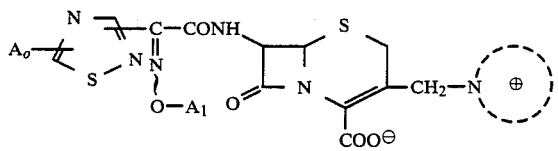

wherein $A_0$ is amino or a protected amino group:

$A_1$ is a lower aliphatic hydrocarbon group which may be substituted with suitable substituent(s), or cyclo(lower)alkenyl, and a group of the formula;

is a heterocyclic cation group containing more than one nitrogen atom which may be substituted with suitable substituent(s).

As the heterocyclic cation group containing more than one nitrogen atom represented by a group of the formula:

there are mentioned unsaturated 5 to 6-membered heteromonocyclic cation group containing more than one nitrogen atom, for example imidazolio, pyrazolio etc.; and unsaturated condensed heterocyclic cation group containing more than none nitrogen atom, for example, indazolio, benzimidazolio, etc. However EP-A-62321 neither describes nor suggests a group of the formula:

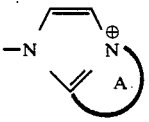

which is the substituent at the 3-position of the cephem compound of the present invention.

Reference to a cephem compound having an imidazo[1,2-a]pyridinium-1-yl

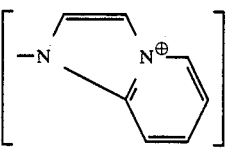

or imidazo[1,2-b]pyridazinium-1-yl

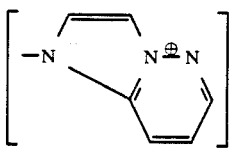

substitutent at the 3-position of the cephem ring is not found in EP-A-160,252 but this reference does not teach a cephem compound having a group of the formula:

—E—(CH$_2$)$_n$—R$^2$ wherein E is sulfur or NH; R$^2$ is an amino, carbamoylamino, formylamino, acetylamino, N-formimidoylamino, N-acetimidoylamino, lower alkylamino, hydroxyl or carbamoyloxy group; and n is an integer of 2 to 4, on the imidazo[1,2-a]pyridine ring or imidazo[1,2-b]pyridazine ring.

In addition, these cephem compounds are not always satisfactory with respect to antibacterial activity and toxicity to man and animals.

The compound (I) or a salt thereof is structurally characterized in that it contains a group of the formula:

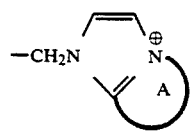

namely a group of the formula:

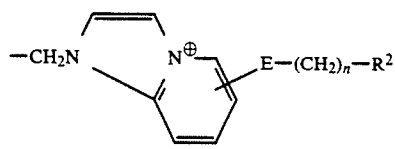

and a group of the formula:

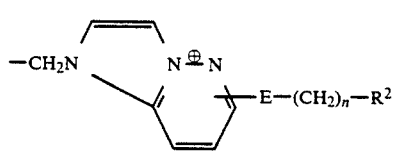

wherein the symbols are as defined hereinbefore, at the 3-position of its cephem nucleus. Based on the unique chemical structure including this specific 3-substituent group and the 7-acyl group as described hereinafter, the compound (I) or a salt thereof exhibits excellent antibacterial activity against a broad range of gram-positive and gram-negative pathogenic bacteria inclusive of various clinical strains (for example, clinically isolated strains belonging to *Citrobacter freundii* and *Enterobacter cloacae*). Particularly noteworthy is the activity of the compound (I) or a salt thereof against *Staphylococcus aureus*, and the compound (I) or a salt (I) thereof substantially has no toxicity to man and animals.

The present invention provides the compound (I) and a salt thereof having such excellent characteristics.

Referring to the above formula (I), Q is a nitrogen atom or CH. Thus, a group of the formula:

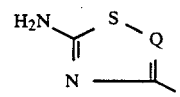

is a 5-amino-1,2,4-thiadiazol-3-yl or 2-aminothiazol-4-yl group.

R$^1$ is hydrogen or a lower alkyl group which may be substituted. The lower alkyl group R$^1$ is preferably a straight-chain or branched-chain alkyl group containing 1 to 6 carbon atoms, such as methyl, ethyl, n-propyl, isopropyl, n-butyl, isobutyl, sec-butyl, tert-butyl, n-pentyl or n-hexyl. The lower alkyl group R$^1$ may have 1 to 3 substituents such as vinyl, carboxyl, C$_{1-6}$alkoxycarbonyl (e.g. methoxycarbonyl ethoxycarbonyl or n-propoxycarbonyl), amino, hydroxy, or a halogen (e.g. fluorine or chlorine). Examples of the substituted lower alkyl group R$^1$ include alkyl, 2-fluoroethyl, 2-chloroethyl, carboxymethyl, 1-methyl-1-carboxyethyl, methoxycarbonylmethyl, 2-aminoethyl, 3-aminopropyl, 4-aminobutyl, 2-hydroxyethyl, 3-hydroxypropyl and 4-hydroxybutyl. Preferably R$^1$ is methyl or ethyl.

Examples of the group of the formula:

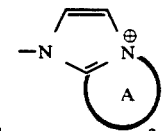

include, among others a group of the formula:

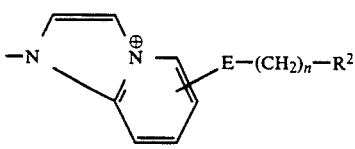

and a group of the formula:

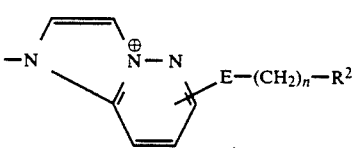

Examples of the group of the formula:

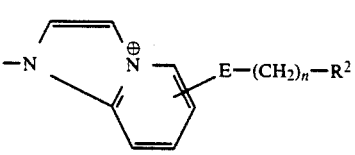

include a group of the formula:

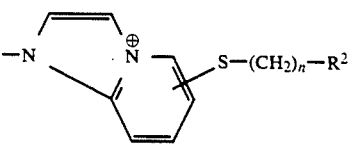

(imidazo[1,2-a]pyridinium-1-yl substituted by —S—(CH$_2$)$_n$—R$^2$) and a group of the formula:

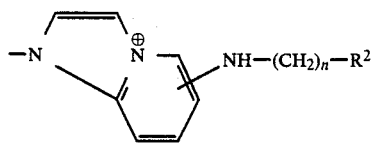

(imidazo[1,2-a]pyridinium-1-yl substituted by —NH—(CH$_2$)$_n$—R$^2$).

Examples of the group of the formula:

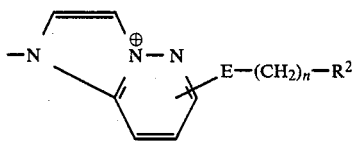

include a group of the formula:

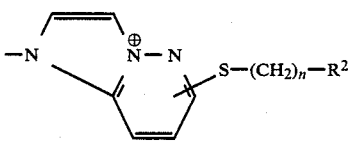

(imidazo[1,2-b]pyridazinium-1-yl substituted by —S—(CH$_2$)$_n$—R$^2$) and a group of the formula:

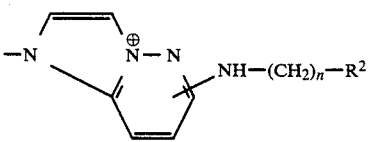

(imidazo[1,2-b]pyridazinium-1-yl substituted by —NH—(CH$_2$)$_n$—R$^2$).

The group of the formula:

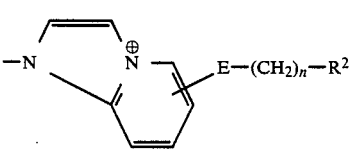

means any one of the group of the formula:

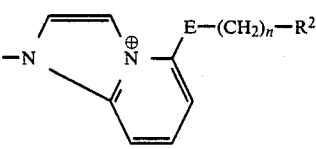

(5-substituted imidazo[1,2-a]pyridinium-1-yl),

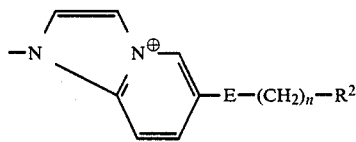

(6-substituted imidazo[1,2-a]pyridinium-1-yl),

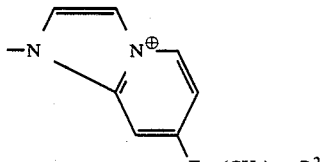

(7-substituted imidazo[1,2-a]pyridinium-1-yl) or

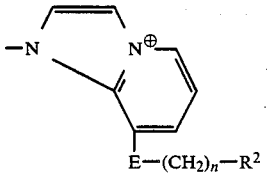

(8-substituted imidazo[1,2-a]pyridinium-1-yl).

The group of the formula:

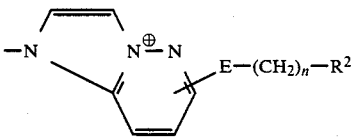

means any one of the group of the formula:

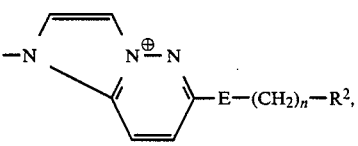

(6-substituted imidazo[1,2-b]pyridazinium-1-yl),

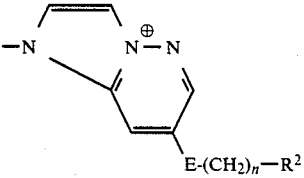

(7-substituted imidazo[1,2-b]pyridazinium-1-yl) or

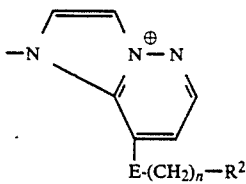

(8-substituted imidazo[1,2-b]pyridazinium-1-yl).

Among the above-mentioned groups, preferred are 5-substituted imidazo[1,2-a]pyridinium-1-yl and 6-substituted imidazo[1,2-b]pyridazinium-1-yl. The most preferred is 5-substituted imidazo[1,2-a]pyridinium-1-yl.

$R^2$ is an amino, carbamoylamino, formylamino, acetylamino, N-formimidoylamino, N-acetimidoylamino, lower alkylamino, hydroxyl or carbamoyloxy group. The lower alkyl group in the lower alkylamino group represented by $R^2$ may be one of those mentioned for $R^1$. Preferably $R^2$ is an amino, carbamoylamino, formylamino, acetylamino, N-formimidoylamino, N-acetimidoylamino, hydroxyl or carbamoyloxy group. More preferably $R^2$ is an amino, formylamino or carbamoyloxy group. Most preferably $R^2$ is a formylamino or carbamoyloxy group.

The symbol n represents an integer of 2 to 4. Preferably n is 2.

Preferable specific examples of the group of the formula:

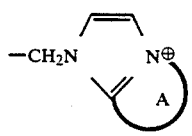

are ① a group of the formula:

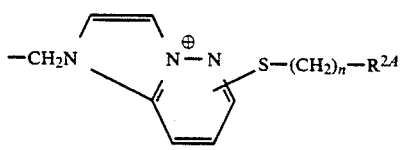

wherein $R^{2A}$ is an amino, N-formimidoylamino, N-acetimidoylamino, carbamoylamino, formylamino, acetylamino, hydroxyl or carbamoyloxy group, n is an integer of 2 to 4, and ② a group of the formula:

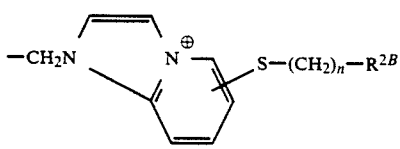

wherein $R^{2B}$ is an amino, N-acetimidoylamino, formylamino, hydroxyl or carbamoyloxy group; and n is an integer of 2 to 4; and ③ a group of the formula:

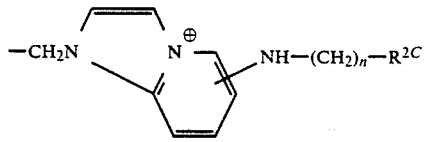

or

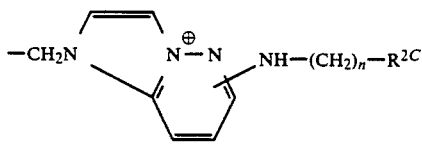

wherein $R^{2C}$ is an amino or N-acetimidoylamino group; and n is an integer of 2 to 4.

In the above groups of the formulas, $R^{2A}$ is preferably an amino group. $R^{2B}$ is preferably an amino, formylamino or carbamoyloxy group. $R^{2C}$ is preferably an amino group.

Of the compounds (I) and salts which have the above substituent ① at the 3-position, the following specific compounds may be mentioned as examples of the particularly effective compounds.

(1) 7β-[2-(5-amino-1,2,4-thiadiazol-3-yl)-(Z)-2-methoxyiminoacetamido]-3-[[6-(2-aminoethylthio)imidazo[1,2-b]pyridazinium-1-yl]methyl]-3-cephem-4-carboxylate, (2) 7β-[2-(5-amino-1,2,4-thiadiazol-3-yl)-(Z)-2-ethoxyiminoacetamido]-3-[6-(2-aminoethylthio)imidazo[1,2-b]pyridazinium-1-yl]methyl]-3-cephem-4-carboxylate, (3) 7β-[2-(2-aminothiazol-4-yl)-(Z)-2-methoxyiminoacetamido]-3-[[6-(2-aminoethylthio)imidazo[1,2-b]-pyridazinium-1-yl]methyl]-3-cephem-4-carboxylate, (4) 7β-[2-(5-amino-1,2,4-thiadiazol-3-yl)-(Z)-2-methoxyiminoacetamido]-3-[[6-(2-hydroxyethylthio)imidazo[1,2-b]pyridazinium-1-yl]methyl]-3-cephem-4-carboxylate, (5) 7β-[2-(5-amino-1,2,4-thiadiazol-3-yl)-(Z)-2-ethoxyiminoacetamido]-3-[[6-(2-hydroxyethylthio)imidazo[1,2-b]pyridazinium-1-yl]methyl]-3-cephem-4-carboxylate, (6) 7β-[2-(2-aminothiazol-4-yl)-(Z)-2-methoxyiminoacetamido]-3-[[6-(2-hydroxyethylthio)imidazo-[1,2-b]pyridazinium-1-yl]methyl]-3-cephem-4-carboxylate, (7) 7β-[2-(2-aminothiazol-4-yl)-(Z)-2-ethoxyiminoacetamido]-3-[[6-(2-aminoethylthio)imidazo[1,2-b]-pyridazinium-1-yl]methyl]-3-cephem-4-carboxylate.

Of the compounds (I) and salts which have the above substituent ②, the following specific compounds may be mentioned as examples of the particularly effective compounds. (1) 7β-[2-(5-amino-1,2,4-thiadiazol-3-yl)-(Z)-2-methoxyiminoacetamido]-3-[[5-(2-aminoethylthio)imidazo[1,2-a]pyridinium-1-yl]methyl]-3-cephem-4-carboxylate, (2) 7β-[2-(5-amino-1,2,4-thiadiazol-3-yl)-(Z)-2-ethoxyiminoacetamido]-3-[[5-(2-aminoethylthio)imidazo[1,2-a]pyridinium-1-yl]methyl]-3-cephem-4-carboxylate, (3) 7β-[2-(2-aminothiazol-4-yl)-(Z)-2-methoxyiminoacetamido]-3-[[5-(2-aminoethylthio)imidazo[1,2-a]-pyridinium-1-yl]methyl]-3-cephem-4-carboxylate, (4) 7β-[2-(5-amino-1,2,4-thiadiazol-3-yl)-(Z)-2-methoxyiminoacetamido]-3-[[5-(2-hydroxyethylthio)imidazo[1,2-a]pyridinium-1-yl]methyl]-3-cephem-4-carboxylate, (5) 7β-[2-(5-amino-1,2,4-thiadiazol-3-yl)-(Z)-2-ethoxyiminoacetamido]-3-[[5-(2-hydroxyethylthio)imidazo[1,2-a]pyridinium-1-yl]methyl]-3-cephem-4-carboxylate, (6) 7β-[2-(2-aminothiazol-4-yl)-(Z)-2-methoxyiminoacetamido]-3-[[5-(2-hydroxyethylthio)imidazo[1,2-a]pyridinium-1-yl]methyl]-3-cephem-4-carboxylate, (7) 7β-[2-(2-aminothiazol-4-yl)-(Z)-2-ethoxyiminoacetamido]-3-[[5-(2-aminoethylthio)imidazo[1,2-a]-pyridinium-1-yl]methyl]-3-cephem-4-carboxylate, (8) 7β-[2-(2-aminothiazol-4-yl)-(Z)-2-ethoxyiminoacetamido]-3-[[5-(2-formylaminoethylthio)imidazo[1,2-a]pyridinium-1-yl]methyl]-3-cephem-4-carboxylate, (9) 7β-[2-(2-aminothiazol-4-yl)-(Z)-2-ethoxyiminoacetamido]-3-[[5-(2-carbamoyloxyethylthio)imidazo[1,2-a]pyridinium-1-yl]methyl]-3-cephem-4-carboxylate.

Of the compounds (I) and salts which have the above substituent ③, the following specific compounds may be mentioned as examples of the particularly effective compounds.

(1) 7β-[2-(2-aminothiazol-4-yl)-(Z)-2-ethoxyiminoacetamido]-3-[[5-(2-aminoethylamino)imidazo[1,2-a]-pyridinium-1-yl]methyl]-3-cephem-4-carboxylate, (2) 7β-[2-(2-aminothiazol-4-yl)-(Z)-2-ethoxyiminoacetamido]-3-[[6-(2-aminoethylamino)imidazo[1,2-b]pyridazinium-1-yl]methyl]-3-cephem-4-carboxylate, (3) 7β-[2-(2-aminothiazol-4-yl)-(Z)-2-methoxyiminoacetamido]-3-[[5-(2-aminoethylamino)imidazo[1,2-a]-pyridinium-1-yl]methyl]-3-cephem-4-carboxylate, (4) 7β-[2-(2-aminothiazol-4-yl)-(Z)-2-methoxyiminoacetamido]-3-[[6-(2-aminoethylamino)imidazo[1,2-b]-pyridazinium-1-yl]methyl]-3-cephem-4-carboxylate, (5) 7β-[2-(5-amino-1,2,4-thiadiazol-3-yl)-(Z)-2-methoxyiminoacetamido]-3-[[5-(2-aminoethylamino)imidazo[1,2-a]pyridinium-1-yl]methyl]-3-cephem-4-carboxylate, (6) 7β-[2-(5-amino-1,2,4-thiadiazol-3-yl-(Z)-2-methoxyiminoacetamido]-3-[[6-(2-aminoethylamino)imidazo[1,2-b]-pyridazinium-1-yl]methyl]-3-cephem-4-carboxylate.

A desirable class of the compound (I) or a salt thereof comprises the compounds wherein a group of the formula:

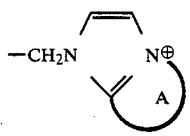

is ① a group of the formula:

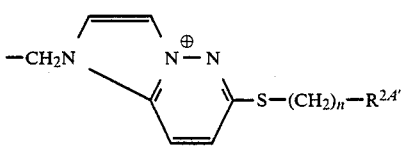

wherein $R^{2A'}$ is an amino or hydroxyl group; n is an integer of 2 to 4; or ② a group of the formula:

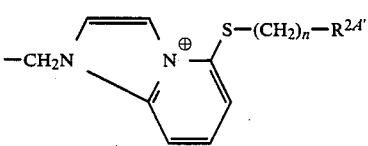

wherein the symbols have the same meanings as defined above; or ③ a group of the formula:

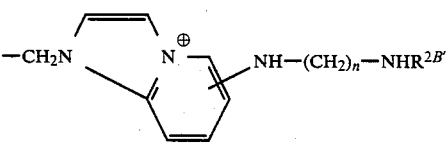

or

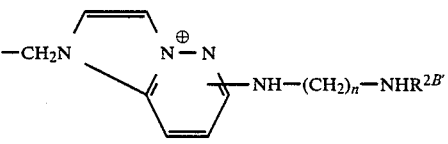

wherein $R^{2B'}$ is hydrogen or a lower alkyl group; and n is an integer of 2 to 4, or a salt thereof.

The lower alky group $R^{2B'}$ is as mentioned for $R^1$.

Referring to the formula (I), the positive charge ⊕ on the 3-substituent of the cephem nucleus may be present on the 1-nitrogen atom, or non-localized on the imidazole ring or the whole fused ring structure of the 3-substituent.

Therefore, as to the group of the formula:

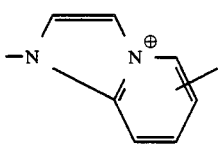

in the substituent;

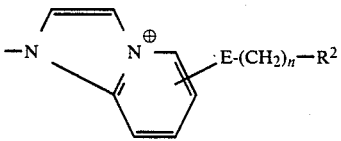

it may be written as

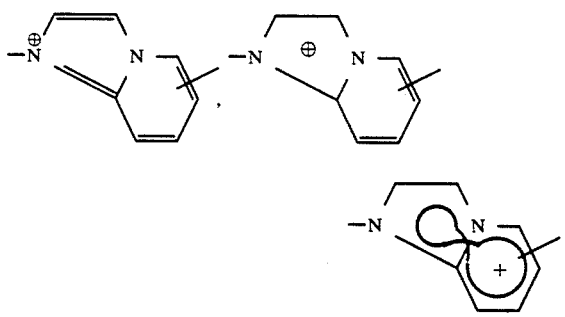

for instance. As to the group of the formula;

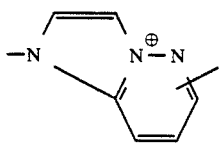

in the substituent;

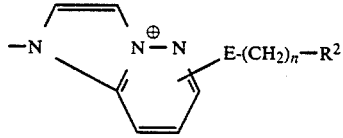

it may be written as

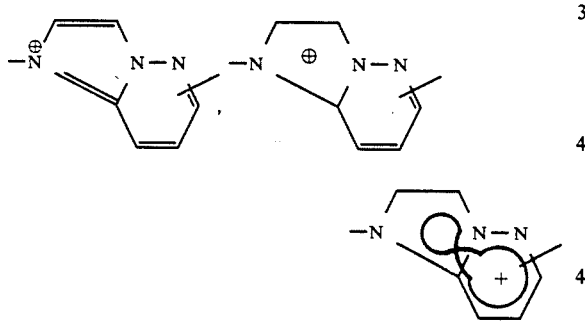

The location of this positive charge varies according to the state (solid or in solution) of compound (I) or a salt thereof, type of solvent, pH, temperature, type of substituent, etc. and the present invention should be construed to cover all cases in which the positive charge is localized at the nitrogen atom and in which the charge is non-localized on the imidazole ring or the whole fused ring structure.

The compound (I) or a salt thereof is a syn-isomer ([Z]-isomer).

The salt of compound (I) is preferably a pharmaceutically acceptable salt. As the pharmaceutically acceptable salt, use is made of inorganic base salts, ammonium salts, organic base salts, inorganic acid addition salts, organic acid addition salts, or basic amino acid salts. Inorganic bases capable of giving the inorganic base salts include alkali metals (e.g. sodium or potassium), alkaline earth metals (e.g. calcium). Organic bases capable of giving the organic base salts include procaine, 2-phenylethylbenzylamine, dibenzylethylenediamine, ethanolamine, diethanolamine, tris-hydroxymethylaminomethane, polyhydroxyalkylamines and N-methylglucosamine. Inorganic acids capable of giving the inorganic acid addition salts include hydrochloric acid, hydrobromic acid, sulfuric acid, nitric acid and phosphoric acid. Organic acids capable of giving the organic acid addition salts include p-toluenesulfonic acid, methanesulfonic acid, formic acid, trifluoroacetic acid and maleic acid. Basic amino acids capable of giving basic amino acid salts include lysine, arginine, ornithine and histidine. Of these salts, base salts (namely inorganic base salt, ammonium salts, organic base salts, and basic amino acid salts) are the salts formed when an acidic group such as carboxyl is present in the substituent $R^1$ of the compound (I). The acid addition salts (namely inorganic acid addition salts and organic acid addition salts) are the acid addition salts of the amino group in the 3-substituent of the cephem nucleus and the acid addition salts formed when a basic group such as amino is contained in the substituent group $R^1$.

The acid addition salts further include (1) a salt formed on addition of 1 mole of an acid per mole of the compound (I) having 4-carboxylate ($COO^-$) moiety and 3-substituent shown by

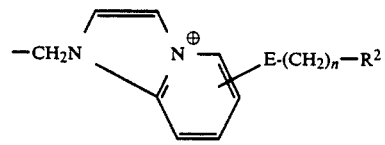

or

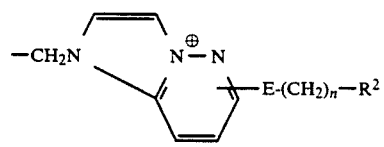

wherein the symbols have the same meanings as defined hereinbefore, i.e. a salt containing a free carboxyl group at the 4-position and a group of the formula:

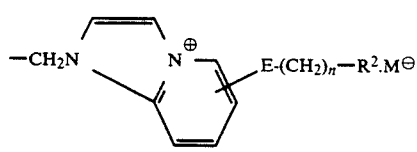

or

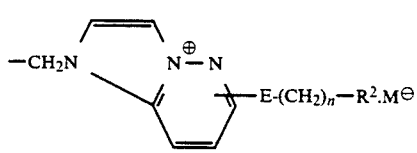

wherein $M^-$ is an anion formed on elimination of a proton ($H^+$) from an inorganic or organic acid, such as chloride ion, bromide ion, ½ sulfate ion, p-toluene-sulfonate ion, methanesulfonate ion or trifluoroacetate ion; and the symbols have the same meanings as defined hereinbefore, at the 3-position, and (2) a salt formed on addition of 2 moles of an acid per mole of the compound (I) having 4-carboxylate ($COO^-$) moiety and 3-substituent shown by

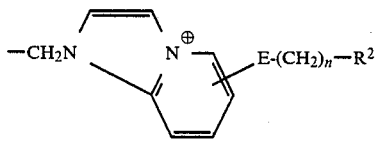

or

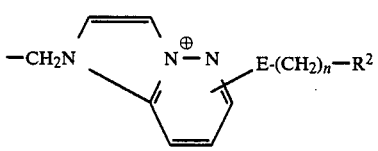

where $R^2$ is an amino, N-forminidoylamino, N-acetimidoylamino or lower alkylamino group; and n is an integer of 2 to 4, i.e. a salt containing a free carboxyl group at the 4-position and a group of the formula:

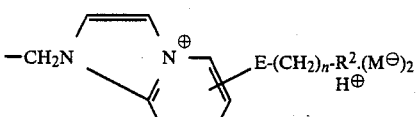

or

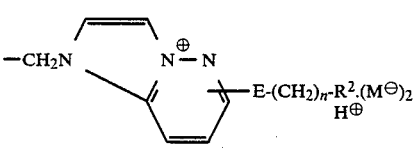

wherein $M^-$ is an anion formed on elimination of a proton ($H^+$) from an inorganic or organic acid, such as chloride ion, bromide ion, ½ sulfate ion, p-toluenesulfonate ion, methanesulfonate ion or trifluoroacetate ion; and $R^2$ is an amino, N-formimidoylamino, N-acetimidoylamino or lower alkylamino group, at the 3-position.

The compound (I) or a salt thereof is a valuable antibiotic showing excellent antibacterial activity against gram-positive and gram-negative bacteria inclusive of clinical isolates and can be safely used as medicines for man and animals in the treatment and prevention of infections caused by various bacteria.

Furthermore, the compound (I) or a salt thereof can be added to animal foods as antibacterial additives for antisepsis of feedstuffs. Moreover, it can be used as bactericides for eradication of harmful bacteria from medical or dental equipment or as industrial bactericides for inhibiting growth of harmful bacteria in aqueous coating materials or paper mill white water.

The pharmaceutical preparation containing the above compound (I) or its pharmaceutically acceptable salt can be prepared according to the conventional manner.

The compound (I) or a salt thereof may be used alone or in combination with other active substances. The compound (I) or a salt thereof may be used with or without addition of pharmaceutically acceptable excipients such as stabilizers or dispersing agents in preparations such as capsules, tablets, powders, solutions, suspensions or elixirs. The compound (I) or a salt thereof can be administered parenterally (for example by intravenous or intramuscular injection) or orally.

Injectable preparations can be provided in unit dosage forms such as ampoules or vials containing an antiseptic agent. The injectable preparations may be suspensions, solutions or emulsions in oily or aqueous vehicles and may contain pharmaceutically acceptable excipients such as the known suspending agents, stabilizers and/or dispersing agents. Moreover, the compound (I) or a salt thereof can be provided as powders for use as extemporaneously dissolved in a suitable vehicle such as sterilized pyrogen-free water.

The compound (I) or a salt thereof can also be formulated with a suitable binder such as syrup, gum arabic, gelatin, sorbitol, gum tragacanth, polyvinylpyrrolidone, etc., a filler such as lactose, carbohydrates, corn starch, calcium phosphate, sorbitol, glycine, etc., a lubricating agent such as magnesium stearate, talc, polyethylene glycol, silica, etc., a disintegrating agent such as potato starch, etc. and/or a wetting agent such as sodium laurylsulfate, into preparations for oral administration such as tablets, capsules, granules or powders in a conventional manner. The tablets and granules, may be film-coated by the established pharmaceutical procedure. Preparations for oral administration may be provided in liquid dosage forms such as aqueous or oil suspensions, solutions, emulsions, syrups or elixirs.

Further, the known antioxidants, preservatives, lubricating agents, thickening agents, flavors and other additives may be further incorporated into such pharmaceutical preparations. Moreover, it is also feasible to provide a preparation having an extended antimicrobial spectrum by adding other active substances, such as β-lactam antibiotics (e.g. penicillins, cephalosporins, monobactams exemplified by aztreonam) to the preparation containing the compound (I) or a salt thereof.

For administration to domestic animals, the compound (I) or a salt thereof can be provided in the form of an intra-udder preparation by incorporating it in a medium adapted to release the active substance slowly over an extended time or a medium adapted to release it rapidly.

The compound (I) or a salt thereof according to the present invention can be used as a therapeutic agent for bacterial infections, for example in the treatment and prevention of respiratory tract infection, urinary tract infection, suppurative diseases, biliary tract infection, enteral infection, gynecological and obstetric infections, surgical infections, etc. in man and other mammalian animals. The daily dosage of compound (I) or a salt thereof varies with the patient's condition and body weight, route of administration, etc. In parenteral administration to adult humans, about 0.5 to 80 mg, preferably about 1 to 20 mg of active substance (compound (I) or salt thereof) per kg body weight can be intravenously administered daily in 2 to 4 divided doses. The daily dosage for oral administration to adult humans is about 5 to 100 mg of active substance (compound (I) or salt thereof) per kg body weight in 1 to 3 divided doses.

The compound (I) or a salt thereof can be produced by the methods known per se (for example by the method described in EP-A-160,252). More specifically, it can be produced by the methods 1 to 4 described hereinafter.

Production Method 1

The compound (I) or a salt thereof can be produced by reacting a compound of the formula (II)

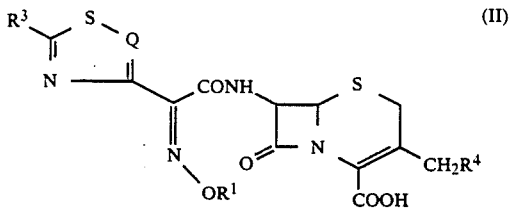 (II)

wherein Q and R¹ have the same meanings as defined hereinbefore; R³ is an amino group which may be protected; R⁴ is a hydroxyl group, an acyloxy group, a carbamoyloxy group, a substituted carbamoyloxy group, or a halogen atom, or a salt thereof with a compound of the formula

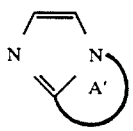 (III)

wherein ring A' is a pyridine or pyridizine ring which is substituted at the ring-constituting carbon atom by a group of the formula:

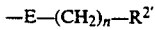

wherein $R^{2'}$ is an amino or lower alkyl amino group which is protected; a hydroxyl, carbamoylamino or carbamoyloxy group which may be protected; or a formylamino or acetylamino group; and the other symbols have the same meanings as defined hereinbefore, or a salt thereof, and if desired, followed by eliminating the protective group, or converting the resulting salt to the corresponding free acid or base, or converting the resulting free acid or base to a pharmaceutically acceptable salt, in an optional order.

Examples of the compound (III) include a compound of the formula:

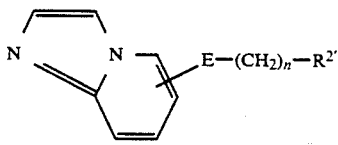 (III')

and a compound of the formula:

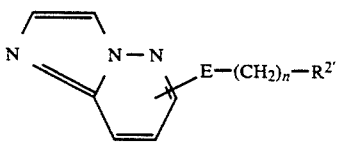 (III'')

wherein the symbols have the same meanings as defined hereinbefore.

Referring to the above formulas, the acyloxy group represented by R⁴ may for example be a group of the formula: A—O— wherein A is an acyl group derived from an organic carboxylic acid, such as an alkanoyl group preferably containing 1 to 7 carbon atoms (for example, formyl, acetyl, propionyl, butyryl, isobutyryl, pentanoyl, hexanoyl or heptanoyl), an arylcarbonyl group preferably containing 7 to 15 carbon atoms (for example, benzoyl or naphthalene-carbonyl), an alkoxy-carbonyl group preferably containing 2 to 7 carbon atoms (for example, methoxycarbonyl, ethoxy-carbonyl, propoxycarbonyl or butoxycarbonyl), an aryloxycarbonyl group preferably containing 7 to 15 carbon atoms (for example, phenoxycarbonyl), an aralkylcarbonyl group preferably containing 8 to 20 carbon atoms (for example, benzylcarbonyl or benzhydrylcarbonyl), a 5 or 6 membered heterocyclic carbonyl group preferably containing 1 to 4 hetero atoms such as nitrogen atom (which may be oxidized), oxygen atom or sulfur atom (which may be oxidized) in the heterocycle, (for example 2- or 3-thienylcarbonyl or 1,2,3-thiadiazol-4 or 5-ylcarbonyl) or a 5 or 6 membered heterocyclic acetyl group, preferably containing 1 to 4 hetero atoms such as nitrogen atom (which may be oxidized), oxygen atom or sulfur atom (which may be oxidized) in the heterocycle (for example, 2- or 3-thienylacetyl, or 2- or 3-furylacetyl), which may be substituted by suitable substituents, such as a halogen (e.g. chlorine or bromine), oxo, carboxyl, $C_{1-4}$ alkoxy (e.g. methoxy or ethoxy), carbamoyl which may be substituted by esterified carboxyl or sulfamoyl which may be substituted by esterified carboxyl.

Examples of the acyloxy group include formyloxy, acetoxy, propionyloxy, butyryloxy, valeryloxy, pivaloyloxy, chloroacetoxy, dichloroacetoxy, trichloroacetoxy, 3-oxobutyryloxy, 4-chloro-3-oxobutyryloxy, 3-carboxypropionyloxy, 4-carboxybutyryloxy, 3-ethoxycarbamoylpropionyloxy, benzoyloxy, naphthoyloxy, p-methylbenzoyloxy, p-methoxybenzoyloxy, p-chlorobenzoyloxy, o-carboxybenzoyloxy, o-(ethoxycarbonylcarbamoy)benzoyloxy, o-(ethoxycarbonylsulfamoyl)benzoyloxy, phenylacetyloxy, p-methylphenylacetyloxy, p-methylphenylacetyloxy, p-chlorophenylacetyloxy, 2,2-diphenylacetyloxy, thienylcarbonyloxy, furylcarbonyloxy, thiazolylacetyloxy, thienylacetyloxy and furylacetyloxy. The substituted carbamoyloxy group represented by R⁴ may for example be mono- or di(an alkyl group of 1 to 6 carbon atoms) carbamoyloxy group, such as N-methylcarbamoyloxy, N,N-dimethylcarbamoyloxy or N-ethylcarbamoyloxy, or mono- or di-(an aryl group of 6 to 14 carbon atoms) carbamoyloxy group, such as N-phenylcarbamoyloxy. The halogen atom represented by R⁴ may for example be chlorine, bromine or iodine.

The amino-protecting group and the protective group for the amino moiety in the lower alkylamino, carbamoylamino and carbamoyloxy groups, represented by $R^{2'}$ and the protective group on the protected amino group R³ may respectively be a group which is commonly used in the fields of β-lactam chemistry and peptide synthesis. Among them, formyl, monochloroacetyl, tert-butoxycarbonyl, benzyloxycarbonyl, p-methoxybenzylcarbonyl, p-nitrobenzyloxycarbonyl, 2-trimethylsilylethoxycarbonyl, 2,2,2-trichloroethoxycarbonyl, trityl and o-nitrophenylthio are preferred.

The protective group on the protected hydroxyl group $R^{2'}$ may be selected from among the hydroxy-protecting groups used commonly in the fields of β-lactam chemistry and peptide synthesis. Particularly preferred are chloroacetyl, 2,2,2-trichloroethoxycarbonyl, 2-trimethylsilylethoxycarbonyl, benzyl, p-nitrobenzyl, trityl, methylthiomethyl, trimethylsilyl, tert-butyldimethylsilyl, 2-tetrahydropyranyl and 4-methoxy-4-tetrahydropyranyl.

Referring to the formula (II), the amino group, if any, in the substituent R¹ is preferably protected with a protective group. This protective group may be as mentioned for $R^3$ and $R^{2'}$. When a hydroxyl group is present in the substituent $R^1$, it is preferably protected with a protective group mentioned for $R^{2'}$.

When a carboxyl group is present in the substituent $R^1$, it is preferably protected with protective group. The protective group on the carboxyl group may be selected from among carboxyl-protecting groups commonly used in the fields of β-lactam chemistry and peptide synthesis. Particularly preferred are benzyl, p-nitrobenzyl, p-methoxybenzyl, benzhydryl, 2-methylsulfonylethyl, 2-trimethylsilylethyl, 2,2,2-trichloroethyl, trityl and trimethylsilyl.

As the salt of compound (II), use is made of the salt with a base which can for example, accelerate the reaction, neutralize the acid produced in the course of the reaction and/or increase the solubility of the starting compound. Examples of the base include tertiary amines such as triethylamine, tri-n-butylamine or diisopropylethylamine and alkali metal hydrogen carbonates such as sodium hydrogen carbonate or potassium hydrogen carbonate. The base may be added together with the compound (II) to the reaction system for the above-mentioned purposes and the preferred amount of addition of the base is generally in the range of about 1 to 5 moles per mole of the compound (II). Examples of the salt of compound (III) include inorganic acid addition salts such as hydrochloride, hydrobromide, sulfate, nitrate or phosphate and organic acid addition salts such as formate, acetate, trifluoroacetate, methanesulfonate or p-toluenesulfonate.

(1): When $R^4$ is a hydroxyl group:

In this reaction, the compound (III) or salt thereof is used in the range of about 1 to 10 moles, preferably about 1 to 5 moles, per mole of the compound (II) or a salt thereof.

This reaction is generally conducted in an organic solvent which does not interfere with the reaction. The examples of the organic solvent, include amides such as formamide, dimethylformamide, dimethylacetamide; halogenated hydrocarbons such as dichloromethane, chloroform or 1,2-dichloroethane; ethers such as diethyl ether, tetrahydrofuran or dioxane; esters such as methyl acetate, ethyl acetate, isobutyl acetate or ethyl propionate; nitriles such as acetonitril or propionitrile; nitro compounds such as nitromethane or nitroethane; ketones such as acetone or methyl ethyl ketone; and aromatic hydrocarbons such as benzene or toluene. These solvents may be used singly or as mixed in appropriate proportions. Particularly preferred are dichloromethane, tetrahydrofuran, acetonitrile, formamide, dimethylformamide, dimethylformamide-acetonitrile, dichloromethane-acetonitrile and dichloromethane-tetrahydrofuran.

For the purpose of accelerating the reaction, use may be made of cyclic phosphorus compound described in EP-A-74611 or a phosphorous acid ester.

Thus, a cyclic phosphorus compound of the formula (VI)

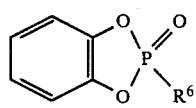

(VI)

wherein $R^6$ is a phenyl group or a lower alkoxy group may be employed. In the formula (VI), the lower alkoxy group $R^6$ is an alkoxy group of 1 to 4 carbon atoms, such as methoxy, ethoxy, propoxy or isobutoxy. Preferred among cyclic phosphorus compounds (VI) are methyl o-phenylene phosphate, ethyl o-phenylene phosphate and 2-phenyl-2-oxo-1,3,2-benzodioxaphosphole. The compound (VI) is used in an amount of about 1 to 10 moles, preferably about 1 to 6 moles per mole of the compound (II) or a salt thereof. When the compound (VI) is used in this reaction, it is preferable to react the compound (II) or a salt thereof, the compound (III) or a salt thereof, and the compound (VI) with one another in the above-mentioned organic solvent. Thus, this reaction may be carried out by mixing the compound (II) or a salt thereof with the compound (III) or a salt thereof in the organic solvent, followed by adding the compound (VI) or a solution of the compound (III) in an organic solvent, or mixing the compound (III) or a salt thereof with the compound (VI) in the organic solvent, followed by adding the compound (II) or a salt thereof or a solution of the compound (II) or a salt thereof in the organic solvent.

The reaction temperature is generally about −80° C. to 60° C., although it varies with the species and amounts of the starting compound (II) or a salt thereof, the starting compound (III) or a salt thereof, the cyclic phosphorus compound (VI), organic solvent, base, and so on. The reaction time is generally about 1 minutes to 24 hours.

(2): When $R^4$ is an acyloxy, carbamoyloxy or substituted carbamoyloxy group

Preferred solvents are water and mixtures of water and water-miscible organic solvents. Preferred water-miscible organic solvents are acetone, methyl ethyl ketone, and acetonitrile.

The compound (III) or a salt thereof is used generally in the range of about 1 to 5 moles, preferably 1 to 3 moles per mole of the compound (II) or a salt thereof. The reaction is conducted within the temperature range of about 10° to 100° C., preferably about 30° to 80° C. The reaction time is generally about 30 minutes to 5 days and preferably about 1 to 5 hours. The reaction is conducted with advantage in the pH range of 2 to 8 and preferably in the neighborhood of neutral region, i.e. pH 5 to pH 8. This reaction generally proceeds with increased facility in the presence of about 2 to 30 equivalents of an iodide or a thiocyanate. Examples of the iodide include sodium iodide and potassium iodide, and examples of the thiocyanate include sodium thiocyanate and potassium thiocyanate. The progress of the reaction may also be rendered smooth by adding a quaternary ammonium salt having surface activity, such as trimethylbenzylammonium bromide, triethylbenzylammonium bromide or triethylbenzylammonium hydroxide.

(3): When $R^4$ is a halogen atom

Preferred examples of the solvent include the above-mentioned ethers, esters, halogenated hydrocarbons, aromatic hydrocarbons, amides, ketones, nitriles, water, and alcohols such as methanol, ethanol or propanol. The compound (III) or a salt thereof is used generally in the range of about 1 to 5 moles, preferably about 1 to 3 moles per mole of the compound (II) or a salt thereof. The reaction is conducted at temperatures within the range of about 0° to 80° C., preferably about 20° to 60° C. The reaction time is generally in the range of about 30 minutes to 15 hours and preferably about 1 to 5 hours. To accelerate the reaction, the reaction may be conducted in the presence of a hydrogen halide acceptor. Examples of the hydrogen halide acceptor include inorganic bases such as sodium carbonate, potassium carbonate, calcium carbonate or sodium hydrogen carbonate, organic tertiary amines such as triethylamine, tri(n-propyl)amine, tri(n-butyl)amine, diisopropylethylamine, cyclohexyldimethylamine, pyridine, lutidine, γ-collidine, N,N-dimethylaniline, N-methylpiperidine, N-methylpyrrolidine or N-methylmorpholine, and alkylene oxides such as propylene oxide or epichlorohydrin. The compound (III) itself may serve as the hydrogen halide acceptor. In this case, the compound (III) is used in a proportion of 2 moles or more per mole of the compound (II) or a salt thereof. The halogen atom $R^4$ may be chlorine, bromine or iodine preferably iodine. The compound (II) wherein $R^4$ is iodine can be easily prepared by the process described in EP-A-74,268 or any process analogous thereto.

The reaction product can be isolated and purified by the known procedures such as solvent extraction, pH adjustment, phasic transfer, salting out, crystallization, recrystallization, or chromatography. When protective groups are present in the reaction product, the protective groups are removed to give the compound (I) or a salt thereof. In the fields of β-lactam and peptide syntheses, amino-, hydroxyl- or carboxyl-protecting groups have been sufficiently studied, and the method of protecting and deprotecting amino, hydroxyl or carboxyl groups has been established. As procedures to remove the protective groups, the known methods such as the method using an acid, the one using a base, the one using hydrazine, the reductive method, or the method using sodium N-methyldithiocarbamate can be employed properly according to the known techniques. More concretely, the protective groups on the amino, hydroxy and carboxyl groups can be eliminated for example by the method using an acid or a base or the reductive method according to the particular kinds of protective groups. The method using an acid, for instance, is conducted under conditions suited to the kind of protective groups and the acid may for example be an inorganic acid such as hydrochloric acid, sulfuric acid, or phosphoric acid; an organic acid such as formic acid, trifluoroacetic acid, propionic acid, benzenesulfonic acid, or p-toluenesulfonic acid, or an acid ion exchange resin. In the method using a base the base may for example be an inorganic base such as the hydroxides and carbonates of alkali metals, e.g. sodium, potassium, etc. or the hydroxides and carbonates of alkaline earth metals, e.g. calcium, or magnesium, an organic base such as metal alkoxides, organic amines, quaternary ammonium salts, or a basic ion exchange resin according to the kind of protective groups to be removed. In the above-mentioned method using an acid or a base, a hydrophilic organic solvent, water or a mixture of them is generally used. Examples of the reductive method are the method using a metal such as tin or zinc, or a metal compound such as chromium dichloride or chromium acetate, and an acid such as an organic or inorganic acid, e.g. acetic acid, propionic acid or hydrochloric acid, and the method of reduction in the presence of a metal catalyst. Examples of the catalyst used in the catalytic reduction method include platinum catalysts such as platinum wire, platinum sponge, platinum black, platinum oxide, colloidal platinum, etc., palladium catalysts such as palladium sponge, palldium black, palladium oxide, palladium-on-barium sulfate, palladium-on-barium carbonate, palladium-on-carbon, palladium-on-silica gel, colloidal palladium, etc. and nickel catalysts such as reducing nickel, nickel oxide, Urushibara nickel and so on. In the reduction using a metal and an acid, a metal compound such as iron or chromium is used in combination with an inorganic acid such as hydrochloric acid, or an organic acid such as formic acid, acetic acid or propionic acid. The reductive method is generally conducted in the presence of a solvent. Taking the catalytic reduction method as an example, an alcohol such as methanol, ethanol, propyl alcohol or isopropyl alcohol or ethyl acetate is generally employed. In the method using a metal and an acid, water or acetone is generally used and when the acid is liquid, the acid itself may be used as the solvent. The reactions in the method using an acid, the method using a base and the reductive method are generally conducted from under cooling to under warming. For eliminating silyl-containing protective groups, fluoride ion-containing compounds such as tetrabutylammonium fluoride or potassium fluoride can be used. Moreover, when the amino protecting group is monochloroacetyl, it can be easily removed using thiourea or sodium N-methyldithiocarbamate, for instance. Thus, removal of amino-, hydroxyl- or carboxyl-protecting groups can be efficiently accomplished by the per se known procedures.

Production Method 2

Alternatively, the compound (I) or a salt thereof can be produced by reacting a compound of the formula:

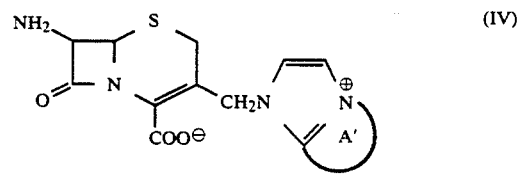

(IV)

wherein the symbols have the same meanings as defined hereinbefore, or a salt thereof with a compound of the formula:

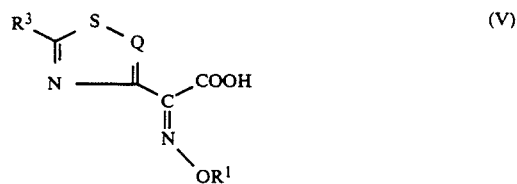

(V)

wherein the symbols have the same meanings as defined hereinbefore or a reactive derivative of the carboxyl group thereof, if desired, followed by removing the protective group or converting the resulting salt to the free acid or free base or converting the resulting free acid or free base to pharmaceutically acceptable salt, in an optional order.

Referring to the formula (V), when an amino group is present in the substituent $R^1$, the amino group is preferably protected and, as a protective group for the amino group, use is made of those mentioned hereinbefore for $R^3$ and $R^{2'}$. When a hydroxyl group is present, the hydroxyl group is preferably protected by the protective group as mentioned hereinbefore. When a carboxyl group is present, it is also preferably protected by the protective group as mentioned hereinbefore.

As the salt of compound (IV), the salt with a base such as those mentioned hereinbefore for the salt of compound (II) may be employed. The base may be added together with the compound (IV), generally in amount of about 1 to 10 moles, preferably about 1 to 5 moles, per mole of the compound (IV).

The reactive derivative of the carboxyl group of compound (V) may be any one of the acid halide, acid anhydride, active amide, active ester, and active thioester which can be prepared in conventional manner. Specific examples of the reactive derivatives are as follows.

(1) Acid halide:

For example, the acid chloride, or acid bromide, may be employed, (2) Acid anhydride:

For example, mixed acid anhydrides with mono-lower alkyl carbonates may be employed.

(3) Active amide:

For example, the amides with pyrazole, imidazole, 4-substituted imidazole, dimethylpyrazole, benzothiazole, or benzotriazole, may be employed.

(4) Active ester:

For example, the methoxymethyl ester, benzothiazole ester, benzotriazole ester, 4-nitrophenyl ester, 2,4-dinitrophenyl ester, trichlorophenyl ester, pentachlorophenyl ester, 1-hydroxyl-1H-2-pyridone ester, N-hydroxysuccinimide ester or N-hydroxyphthalamide ester may be employed.

(5) Active thioester:

For example, the thioesters with heterocycle-thiols such as 2-pyridylthiol or 2-benzothiazolylthiol may be employed.

In this reaction, the compound (V) or a reactive derivative of the carboxyl group thereof is used generally in a proportion of at least 1 mole, preferably about 1 to 4 moles per mole of the compound (IV) or a salt thereof.

This reaction is generally conducted in a solvent. Examples of the solvent include water, ketones such as acetone, ethers such as tetrahydrofuran or dioxane, nitriles such as acetonitrile, halogenated hydrocarbons such as dichloromethan, chloroform or 1,2-dichloroethane, esters such as ethyl acetate and amides such as dimethylformamide or dimethylacetamide. These solvents can be used singly or as mixed in appropriate proportions. When the compound (V) is used in its free form, the reaction is preferably conducted in the presence of a condensing agent. Examples of the condensing agent include N,N'-dicyclohexylcarbodiimide, N-cyclohexyl-N'-morpholinoethylcarbodiimide, N-cyclohexyl-N'-(4-diethylaminocyclohexyl)carbodiimide and N-ethyl-N'-(3-dimethylaminopropyl)carbodiimide.

The reaction may also be conducted in the presence of a base. Examples of the base include an alkali metal carbonate such as sodium carbonate or potassium carbonate, or a tertiary amine such as triethylamine, tri-n-butylamine, N-methylmorpholine, N-methylpiperidine, N,N-dimethylaniline, pyridine, picoline or lutidine. The base has the property to promote the reaction, neutralize the acid produced as a by-product in the course of the reaction and/or facilitate dissolution of the starting compounds. The base is used generally in an amount of about 0.01 to 10 moles, preferably about 0.1 to 5 moles per mole of the compound (IV) or a salt thereof.

There is no particular limitation on the reaction temperature but the reaction is preferably conducted at abut −30° C. to 50° C. in many instances. The reaction time may range from several minutes to about tens of hours (for example, 5 minutes to 30 hours). The reaction product can be isolated and purified by the known procedures as in the case of Production Method 1. When the product contains protective groups, they may be removed by the conventional procedures mentioned hereinbefore to give the compound (I) or a salt thereof.

Production Method 3

The compound (I) or a salt thereof can be produced by reaction a compound of the formula:

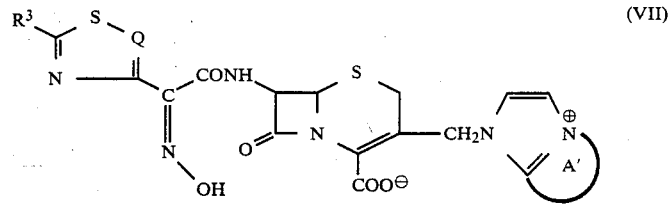

(VII)

wherein the symbols have the same meanings as defined hereinbefore or a salt thereof with a compound of the formula:

$R^{1'}OH$ (VIII)

wherein $R^{1'}$ is a lower alkyl group which may be substituted or a reactive derivative thereof, if desired, followed by removing the protective groups or converting the resulting salt to the corresponding free acid or base or converting the resulting free acid or base to a pharmaceutically acceptable salt, in an optional order.

The lower alkyl group which may be substituted, as represented by $R^{1'}$ in the above formula (VIII), is as defined for $R^1$.

Referring to the formula (VIII), when the substituent represented by $R^{1'}$ contains an amino group, the amino group is preferably protected. Examples of the protective group for the amino group include the protective group mentioned for $R^3$ and $R^{2'}$. When a hydroxyl group is present, the hydroxyl group is preferably protected with a protective group such as those mentioned for $R^1$. When a carboxyl group is present in the substituent, it is also preferably protected with a group such as those mentioned for $R^1$.

In this production method, the hydroxyimino compound (VII) or a salt thereof is reacted with the compound (VIII) ($R^{1'}OH$) or a reactive derivative thereof to give the compound (I) or a salt thereof. The compound (VIII) may be used in its free form or in the form of a reactive derivative. As the reactive derivative of compound (VIII), use is made of derivatives of $R^{1'}OH$ having a substituent which leaves with the hydrogen atom of hydroxyimino compound (VII), such as a compound of the formula $R^{1'}Y$, diazoalkane or dialkyl sulfate. In the formula $R^{1'}Y$, Y may be a halogen atom or a mono-substituted sulfonyloxy group. The halogen atom may for example be chlorine, bromine or iodine. Examples of the mono-substituted sulfonyloxy group include alkylsulfonyloxy groups such as methylsulfonyloxy or ethylsulfonyloxy and arylsulfonyloxy groups such as benzenesulfonyloxy or p-toluenesulfonyloxy. Examples of the diazoalkane include diazomethane and diazothane. Examples of the dialkyl sulfate include dimethyl sulfate and diethyl sulfate.

The compound (VII) or a salt thereof can be produced by the acylation reaction described in Production Method 2 or by the substitution reaction at the 3-position described in Production Method 1.

(1) When $R^{1'}OH$ is used:

The hydroxyimino compound (VII) or a salt thereof is reacted with the compound (VIII) in the presence of a dehydrating agent to give the compound (I) or a salt thereof. As the dehydrating agent, use is made of phosphorus oxychloride, thionyl chloride, dialkyl azodicarboxylate (generally used in combination with a phosphine), or N,N'-dicyclohexylcarbodiimide. Preferred is diethyl azodicarboxylate in combination with triphenylphosphine. The reaction using diethyl azodicarboxylate in the presence of triphenylphosphine is generally conducted in an anhydrous solvent, and the ethers or aromatic hydrocarbons as mentioned hereinbefore may be used for this purpose. Relative to each mole of hydroxyimino compound (VII) or a salt thereof, each of diethyl azodicarboxylate and triphenylphosphine is used in an amount of about 1 to 1.5 moles. The reaction temperature is about 0° to 50° C. The reaction time is about 1 to 4 days.

(2) When $R^{1'}Y$ is used:

The reaction between $R^{1'}Y$ and hydroxyimino compound (VII) or a salt thereof is conventional etherification reaction. This reaction is conducted in a solvent. The ethers, esters, halogenated hydrocarbons, aromatic hydrocarbons, amides, ketones, nitriles, alcohols or water as well as a mixture thereof which have been mentioned in connection with Production Method 1 may be used as the solvent for this reaction. Preferred is a mixture of a water-miscible solvent and water (e.g. aqueous methanol, aqueous ethanol, aqueous acetone or aqueous dimethyl sulfoxide). This reaction can be conducted smoothly in the presence of a base. Examples of the base include an inorganic base such as alkali metal carbonates or hydrogen carbonates, e.g. sodium carbonate, sodium hydrogen carbonate or potassium carbonate and alkali metal hydroxides, e.g. sodium hydroxide or potassium hydroxide. This reaction may be conducted in a buffer solution at pH 7.5 to 8.5. Relative to each mole of the compound (VII) or a salt thereof, the reagent $R^{1'}Y$ and the base are used in the amounts of about 1 to 5 moles, preferably about 1 to 3 moles and about 1 to 10 moles, preferably about 1 to 5 moles, respectively.

The reaction temperature is about $-30°$ C. to about 100° C., preferably about 0° to 80° C. The reaction time is about 10 minutes to 15 hours, preferably about 30 minutes to 5 hours.

(3) When a diazoalkane is used:

This reaction is generally conducted in a solvent. As the solvent, the above-mentioned ethers or aromatic hydrocarbons may be employed. The hydroxyimino compound (VII) or a salt thereof is dissolved in a solvent and a solution of a diazoalkane compound is added thereto, whereupon the reaction proceeds. The diazoalkane is used generally in an amount of about 1 to 10 moles, preferably about 1 to 5 moles per mole of the compound (VII) or a salt thereof. The reaction is carried out at a comparatively low temperature, namely at about $-50°$ C. to 20° C., preferably at about $-30°$ C. to 0° C. The reaction time is about 1 minute to 5 hours, preferably about 10 minutes to 1 hour.

(4) When a dialkyl sulfate is used:

The reaction is generally conducted in water or a mixture of a water-miscible organic solvent with water. As the mixed solvent, the aqueous solvents mentioned in connection with Production Method 3 (2) may be employed. This reaction is generally carried out in the presence of an inorganic base such as alkali metal hydroxides, e.g. sodium hydroxide or potassium hydroxide. The dialkyl sulfate is used in an amount of about 0.5 to 10 moles, preferably about 1 to 2 moles per mole of compound (VII) or a salt thereof.

The reaction temperature is about 20° to 100° C., preferably about 50° to 100° C. The reaction time is about 10 minutes to 5 hours, preferably about 30 minutes to 3 hours.

Following these reactions, if desired, removal of protective group, and isolation and purification are carried out to give the objective compound (I) or a salt thereof.

Production Method 4

The compound of the formula (I), wherein Q is CH, or a salt thereof can be produced in the following manner.

Thus, a compound of the formula:

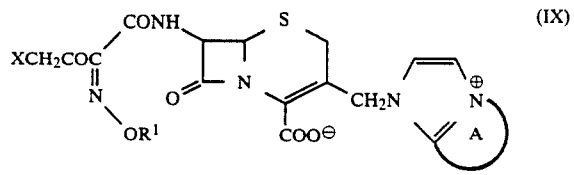

wherein X is a halogen atom and the other symbols have the same meanings as defined hereinbefore or a salt thereof is reacted with thiourea and, if desired, followed by eliminating protective group, or converting the resulting salt to the corresponding free acid or base, or converting the resulting free acid or base to a pharmaceutically acceptable salt, in an optional order to give a compound of the formula:

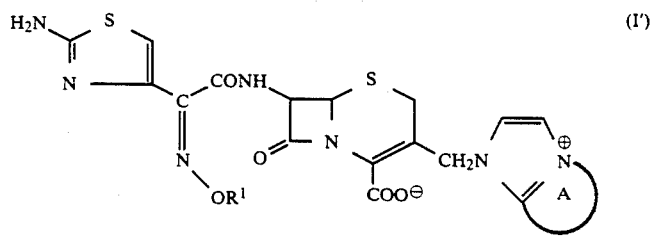

wherein the symbols have the same meanings as defined hereinbefore or a salt thereof.

Referring to the compound (IX), X is a halogen atom, such as chlorine, bromine or iodine. As the salt of compound (IX), use is made of the salts mentioned for the compound (II) described in Production Method 1 (e.g. inorganic base salts, ammonium salts, organic base salts, inorganic acid addition salts, organic acid addition salts).

This reaction is generally conducted in a solvent. Examples of the solvent include ethers such as dioxane, tetrahydrofuran or diethyl ether, alcohols such as methanol, ethanol or n-propanol and amides such as dimethylformamide or dimethylacetamide. Thiourea is used generally in an amount of about 1 to 5 moles, preferably about 1 to 3 moles per mole of the compound (IX) or a salt thereof. The reaction is conducted within the range of about 0° to 100° C., preferably about 20° to 60° C. The reaction time is generally about 30 minutes to 15 hours, preferably about 1 to 5 hours. The reaction product can be isolated and purified by the known procedures mentioned in connection with Production Method 1. When the reaction product contains protective group, the protective group can be removed by the aforementioned conventional procedures, if desired, to give the compound (I') or a salt thereof.

The compound (I) [wherein $R^2$ is an amino group] or a salt thereof, obtained by Production Method 1 through 4 may be subjected to imidation reaction, to obtain the compound (I) [wherein $R^2$ is a N-formimidoylamino or N-acetimidoylamino group] or a salt thereof. Thus, in the imidation reaction, the compound (I) wherein $R^2$ is an amino group or a salt thereof is reacted with a compound of the formula:

(XI)

wherein $R^8$ is hydrogen or a methyl group; $R^9$ is a lower alkyl group or an optionally substituted benzyl group; and Z is oxygen or sulfur, or a salt thereof.

Referring to the formula (XI), a lower alkyl group represented by $R^9$ is as defined for $R^1$, and preferably a methyl or ethyl group. The substituens on the substituted benzyl group represented by $R^9$ may be a lower alkyl group such as a methyl or ethyl group, or a lower alkoxy group such as a methoxy or ethoxy group. Preferably $R^9$ is a benzyl group. Preferably Z is oxygen.

This reaction is generally conducted in a solvent which does not interfere with the reaction. Examples of the solvent include organic solvent e.g. ethers such as dioxan or tetrahydrofuran; alcohols such as methanol, ethanol or n-propanol; amides such as dimethylacetamide, dimethylformamide; ketones such as acetone or methyl ethyl ketone; halogenated hydrocarbons such as dichloromethan or chloroform; or acetonitrile and water. These solvent may be used singly or as a mixture thereof. The preferable example of the solvent is water.

The compound (XI) or a salt thereof is used in an amount of about 1 to 20 moles, preferably about 2 to 10 moles per mole of the compound (I) or a salt thereof.

The reaction temperature is about −20° C. to 60° C., preferably about 0° to 20° C. The reaction time is about 5 minutes to 15 hours, preferably about 10 minutes to 2 hours. In the case where water or a mixture of water and organic solvent described above is used as a solvent, the reaction is generally conducted at a pH value of from about 8 to 13, preferably about 8 to 10. In the case where organic solvents described above are used, the reaction is preferably conducted preferably in the presence of an organic base. Preferable examples of the base include triethylamine and ethyldiisopropylamine.

The organic base is generally used in an amount of about 1 to 5 moles per mole of the compound (I) or a salt thereof.

The resulting compound can be isolated and purified according to per se known procedures, as in Production Method 1 through 4. The compound [XI] is known and described in e.g. Japanese Published Unexamined Patent Application N. 52-85188.

The starting compound (IX) or a salt thereof can be easily produced by reacting a compound of the formula:

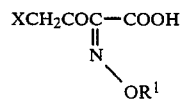

wherein the symbols have the same meanings as defined hereinbefore or a salt or reactive derivative thereof with the compound (IV) or a salt thereof in the manner described in Production Method 2.

The above compound of the formula:

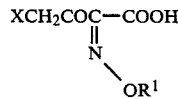

or a reactive derivative thereof can be easily prepared by the per se known method or a method analogous thereto.

When the compound (I) obtained according to the above Production Methods 1 through 4 is a free acid or a free base, it can be converted to a desired pharmaceutically acceptable salt by a per se known procedure and when the compound (I) is a salt, it can be converted to the corresponding free acid or free base by a per se known procedure. It is also feasible to effect such conversion to the salt, free acid or free base in the stage of crude product and, then, purify and isolate the compound (I) or a salt thereof by the above-mentioned purification procedures.

The conversion may be carried out before or after the removal of protective group.

In Production Methods 1 through 4, there are cases in which the compound (I) (syn[Z]-isomer) is obtained in a mixture with the anti[E]-isomer. To separate the desired syn-isomer (i.e. the compound (I) or a salt thereof) from such a mixture, the per se known method or any method analogous thereto can be employed. Thus, fractionation procedures utilizing a difference in solubility or crystallizability or chromatographic procedures can be utilized.

The starting compound (II) or a salt thereof which is employed in Production Methods 1 and 2 described hereinbefore can be prepared by the methods described for example in DE-OLS Nos. 2,715,385; 2,707,565; 2,223,375; U.S. Pat. Nos. 4,098,888; 4,203,899; 4,205,180; 4,298,606; 4,355,160 or by methods analogous thereto. Moreover, the compound (III) can be prepared for example by the method described in EP-A-160,252 or the method which is hereinafter described as Reference Example or any method analogous thereto or the method mentioned below.

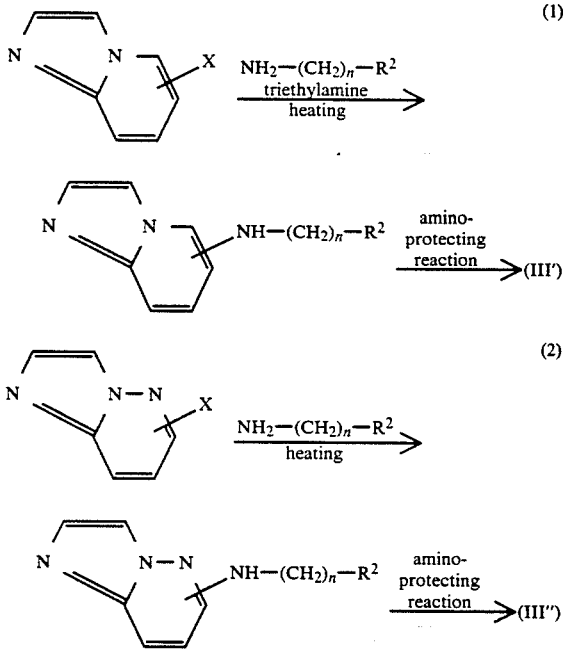

wherein the symbols have the same meanings as defined hereinbefore. The compound (IV) or a salt thereof can be prepared for example by reacting a compound of the formula:

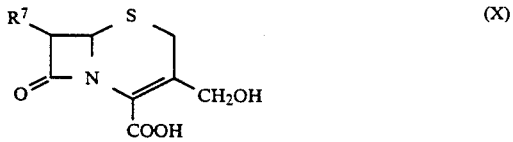

wherein $R^7$ is a protected amino group such as those mentioned hereinbefore or a salt thereof with the compound (III) or a salt thereof, followed by removing the amino-protecting group. Thus, the reaction of the compound (X) or a salt thereof with the compound (III) or a salt thereof can be conducted in the same manner as the aforementioned reaction of the compound (II) or a salt thereof with the compound (III) or a salt thereof. Following this reaction, the amino-protecting group is removed by the procedure described hereinbefore and, if desired, conversion to a salt is conducted in the conventional manner to give the compound (X) or a salt thereof. As the salt of compound (X), salts with the bases mentioned for salts of compound (II) can be used. Moreover, the compound (V) or a reactive derivative of the carboxyl group can be prepared by the methods described for example in DE-OLS Nos. 2,223,375; 2,715,385; 2,702,501; 2,713,272; Japanese Published Examined Patent Application No. 59-19101; DE-OLS No. 2,707,565; U.S. Pat. Nos. 4,098,888; 4,203,899; 4,205,180; 4,298,606; 4,355,160; DE-OLS No. 2,556,736 or the methods analogous thereto.

The compound (I) or a salt thereof which is provided by the present invention shows high antibacterial activity and a broad antibacterial spectrum which makes it of value as a medicine for the prevention and treatment of various diseases caused by pathogenic bacteria in man and animals, such as respiratory and urinary tract infections. The outstanding characteristics of the antibacterial spectrum of antimicrobially active compound (I) or a salt thereof are as follows.

(1) Very high activity against a large variety of gram-negative bacteria;

(2) High activity against gram-positive bacteria (for example, Staphylococcus aureus and Corynebacterium diphtheriae);

(3) Marked efficacy against Pseudomonas aeruginosa strains which are not sensitive to therapy with the conventional cephem antibiotics;

(4) High activity against high β-lactamase producing clinical strains of Citrobacter freundii, Enterobacter cloacae and so on.

Hitherto, aminoglycoside antibiotics such as amikacin or gentamicin have been used against Pseudomonas genus inclusive of Ps. aeruginosa but the compound (I) or a salt thereof according to the present invention is advantageous over these known antibiotics in that it not only exhibits antibacterial activity comparable to that of such aminoglycosides but is by far less toxic to man and animals than are the aminoglycosides.

The compound (I) or a salt thereof is substantially nontoxic to internal organs, such as the liver, kidney, gall bladder or spleen in man and animal, and is readily soluble in water and stable, thus being particularly suited for injection administration.

The present invention is hereinafter described in further detail by way of Reference Examples and working Examples which, however, are merely intended to illustrate and not to restrict the invention.

In the column chromatographic procedures described in the Reference Examples and working Examples, elution was invariably carried out under TLC (thin-layer chromatography) monitoring. For TLC monitoring, Merck 60 $F_{254}$ plates were used as TLC plates and the solvent used as the eluent in column chromatography was used as the developer. For detection, a UV detector was employed. As silica gel for columns, Merck's Kieselgel 60 (230–400 mesh) was used. The "Sephadex" used was the product of Pharmacia Fine Chemicals. The XAD-II resin was the product of Rohm & Hass Co. and the Diaion HP20 was the product of Mitsubishi Kasei Ltd. (Japan). The NMR spectra were measured by means of an XL-100A (100 MHz), EM 360 (60 MHz), EM 390 (90 MHz) or $T_{60}$ (60 MHz) spectrometer using tetramethylsilane either as the internal standard or the external standard and all chemical shifts are shown in δ ppm. The figure given in parentheses for each solvent mixture is the volumetric proportions of constituent solvents. The symbols used in Reference Examples and working Examples have the following meanings.

s: singlet
d: doublet
t: triplet
q: quartet
aBq: AB-pattern quartet
dd: double doublet
m: multiplet
br.: broad
J: coupling constant

REFERENCE EXAMPLE 1

In 100 ml of water is suspended 10 g of 7-aminocephalosporanic acid (briefly, 7-ACA), and with ice-cooling and stirring, 2N-aqueous sodium hydroxide solution is added gradually to maintain the pH at 12.5 to 13.4. After about 2 hours of stirring, the reaction mixture is assayed by TLC and after confirming the disappearance of the starting material (7-ACA), the reaction mixture is adjusted to pH 3.4 with 4N-hydrochloric acid. The crystals that separate out are collected by filtration, washed with water and acetone, and dried in vacuo over phosphorus pentoxide to give 5.4 g light yellow crystals of 7β-amino-3-hydroxymethyl-3-cephem-4-carboxylic acid.

IR(KBr)cm$^{-1}$: 3400, 3190, 3000, 2930, 2600, 1795, 1615.

Elemental analysis: $C_8H_{10}N_2O_4S.\frac{1}{2}H_2O$: Calcd.(%): C, 41.33; H, 4.44; N, 12.05. Found (%): C, 41.29; H, 4.39; N, 11.84.

REFERENCE EXAMPLE 2

In 800 ml of water-tetrahydrofuran (briefly, THF) (1:1) is suspended 16.9 g of 7β-amino-3-hydroxymethyl-3-cephem-4-carboxylic acid, and with ice-cooling and stirring, 27.72 g of sodium hydrogen carbonate is added. Then, 29.4 g of 2-(2-chloroacetamidothiazol-4-yl)-(Z)-2-methoxyiminoacetyl chloride hydrochloride is added gradually thereto and the mixture is stirred for 30 minutes. To this reaction mixture are added 150 ml of water and 200 ml of ethyl acetate and the water layer is separated. Under ice-cooling and stirring, this water layer is adjusted to pH 7.0 with 1N-hydrochloric acid. Under stirring at room temperature, 18.9 g of sodium N-methyldithiocarbamate is added gradually to thereby eliminate the aminoprotective group (This is confirmed by TLC). To the reaction mixture is added 300 ml of ethyl acetate and the water layer is separated and concentrated under reduced pressure to 70 ml. The residue is chromatographed on a column of XAD-II (1 l) and eluted with water. The fractions rich in the desired compound are pooled and concentrated to 100 ml, and with ice-cooling and stirring, the residue is adjusted to pH 2.5 with 4N-hydrochloric acid. The resulting crystals are collected by filtration, washed with 100 ml of water, 50 ml of ethyl acetate and 50 ml of THF, and dried under reduced pressure. The above procedure yields 19.3 g of 7β-[2-(2-aminothiazol-4-yl)-(Z)-2-methoxyiminoacetamido]-3-hydroxymethyl-3-cephem-4-carboxylic acid IR(KBr)cm$^{-1}$: 3330, 3250, 2930, 1760, 1655.

NMR(d$_6$-DMSO)δ: 3.84 (3H, s), 4.25 (2H, s), 6.73 (1H, s).

Elemental analysis: $C_{14}H_{15}N_5I_6S_2\frac{1}{2}H_2O$: Calcd.(%): C, 39.81; H, 3.82; N, 16.58. Found (%): C, 39.73; H, 3.74; N, 16.39.

To a solution of 1.85 g of tri-n-butylamine in 150 ml of methanol is added 4.13 g of the above product compound at $-20°$ C. with stirring. After stirring until a clear solution is obtained, the methanol is distilled off under reduced pressure and 200 ml of dry dichloromethane is added to the residue. The solvent is then distilled off under reduced pressure and the residue is dried to give 7β-[2-(2-aminothiazol-4-yl)-(Z)-2-methoxyiminoacetamido]-3-hydroxymethyl-3-cephem-4-carboxylic acid tri-n-butylamine salt as a foamy product in a nearly quantitative yield.

In the same manner as above, the following compound is synthesized.

(a) 7β-[2-(2-Aminothiazol-4-yl)-(Z)-2-ethoxyiminoacetamido]-3-hydroxymethyl-3-cephem-4-carboxylic acid IR(KBr)cm$^{-1}$: 1765, 1665.

NMR(d$_6$-DMSO)δ: 1.23 (3H, t, J=7 Hz), 4.11 (2H, q, J=7 Hz), 4.26 (2H, s), 6.72 (1H, s).

(b) 7β-[2-(2-Aminothiazol-4-yl)-(Z)-2-ethoxyiminoacetamido]-3-hydroxymethyl-3-cephem-4-carboxylic acid tri-n-butylamine salt (foamy powders)

REFERENCE EXAMPLE 3

To 100 ml of dichloromethane are added 1.08 g of 2-(5-amino-1,2,4-thiadiazol-3-yl)-(Z)-2-ethoxyiminoacetic acid, 1.03 g of dicyclohexylcarbodiimide, and 0.765 g of 1-hydroxybenzotriazole monohydrate and the mixture is stirred at room temperature for 2 hours, at the end of which time the crystals are collected by filtration. On the other hand, 1.26 g of sodium 7β-amino-3-hydroxymethyl-3-cephem-4-carboxylate is suspended in 25 ml of dimethylacetamide, and to this suspension is added the whole amount of the above crystals, followed by stirring at room temperature for 4 hours and at 5° C. for 14 hours. This reaction mixture is shaken with 30 ml of water and 100 ml of ethyl acetate and the water layer is separated and concentrated under reduced pressure to about 10 ml. The concentrate is subjected to silica gel (170 g) column chromatography. After the column is washed with acetonitrile, elution is carried out with acetonitrile-water (4:1) and the eluate is concentrated under reduced pressure to 20 ml. The concentrate is then chromatographed on an XAD-II (200 ml) column and after the column is washed with water, elution is carried out with 10% (v/v) ethanol. The eluate is concentrated under reduced pressure and the concentrate is freeze-dried to give 1.29 g of colorless powders of sodium 7β-[2-(5-amino-1,2,4-thiadiazol-3-yl)-(Z)-2-ethoxyiminoacetamido]-3-hydroxymethyl-3-cephem-4-carboxylate.

IR(KBr)cm$^{-1}$: 3300, 1760, 1670, 1610.

NMR(d$_6$-DMSO)δ: 1.26 (3H, t, J=7 Hz), 3.96 (2H, ABq, J=12 Hz), 4.16 (2H, q, J=7 Hz), 4.92 (1H, d, J=5 Hz), 5.60 (1H, dd, J=5.8 Hz).

Elemental analysis: $C_{14}H_{15}N_6NaO_6S_2.2H_2O$: Cacld.(%): C, 34.57; H, 3.94; N, 17.28. Found (%): C, 34.76; H, 3.84; N, 17.18.

In the same manner as above, the following compound is synthesized.

Sodium 7β-[2-(5-amino-1,2,4-thiadiazol-3-yl)-(Z)-2-methoxyiminoacetamido]-3-hydroxymethyl-3-cephem-4-carboxylate IR(KBr)cm$^{-1}$: 1760, 1665, 1600.

NMR(D$_2$O)δ: 4.18 (3H, s), 4.37 (2H, s), 5.30 (1H, d, J=5 Hz), 5.92 (1H, d).

Elemental analysis: $C_{13}H_{13}N_6NaO_6S_2.2H_2O$: Cacld.(%): C, 33.05; H, 3.63; N, 17.79. Found (%): C, 33.09; H, 3.55; N, 17.61.

REFERENCE EXAMPLE 4

To 150 ml of dichloromethane are added 5.90 g of triphenylphosphine and 7.48 g of 2,2'-dithiobis(benzothiazole) and the mixture is stirred at room temperature for 30 minutes. Then, with ice-cooling and stirring, 6.65 g of 2-(2-tritylaminotbiazol-4-yl)-(Z)-2-methoxyiminoacetic acid and the whole mixture is stirred for 3.5 hours. The reaction mixture is filtered and the filtrate is concentrated under reduced pressure. The residue is chromatographed on a silica gel (300 g) column and elution is carried out with chloroform-ethyl acetate (50:1). The fractions rich in the desired thioester are pooled and the solvent is distilled off to give 7.0 g of a foamy product. On the other hand, 2.88 g of 7β-amino-3-hydroxymethyl-3-cephem-4-carboxylic acid is suspended in 50 ml of water, and with ice-cooling and stirring, the suspension is adjusted to pH 7.5 by dropwise addition of 1N aqueous sodium hydroxide solution, whereupon a substantially clear solution is obtained. To this solution is added a solution preprared by dissolving the whole amount of the above foamy product (thioester) in 100 ml of THF and the mixture is stirred at room temperature for 22 hours. The reaction mixture is concentrated under reduced pressure and the residue is subjected to XAD-II (300 ml) column chromatography. Successive elution is carried out with 1 l of water, 200 ml each of 10%, 20% and 30% (v/v) ethanol-water mixtures, and finally 1 l of 50% (v/v) ethanol. The fractions rich in the desired compound are pooled and concentrated under reduced pressure and the residual aqueous solution is freeze-dried to give 4.82 g of light yellow powders of sodium 7β-[2-(2-tritylaminothiazol-4-yl)-(Z)-2-methoxyiminoacetamido]-3-hydroxymethyl-3-cephem-4-carboxylate.

IR(KBr)cm$^{-1}$: 3400, 1760.

NMR(d$_6$-DMSO)δ: 3.80 (3H, s), 3.95 (2H, ABq), 6.68 (1H, s).

Elemental analysis: $C_{33}H_{28}N_5NaO_6S_2 \cdot 1.5H_2O$: Calcd.(%): C, 56.24; H, 4.43; N, 9.94. Found (%): C, 56.18; H, 4.55; N, 9.68.

REFERENCE EXAMPLE 5

In 180 ml of acetonitrile is suspended 6.87 g of 2-(2-formamidothiazol-4-yl)-(Z)-2-methoxyiminoacetic acid, followed by addition of 4.56 g of N-methylmorpholine with stirring, which results in substantial dissolution. Then, 11.97 g of 2,2'-diothiobis(benzothiazole) is added and with ice-cooling and stirring, a solution of 8.67 g of triethyl phosphite in 42 ml of acetonitrile is added dropwise over a period of 30 minutes. The mixture is stirred under ice-cooling for 5 hours and, then, allowed to stand in a refrigerator for 2 days. The solvent is then distilled off under reduced pressure, and after addition of 500 ml of isopropyl ether, the residue is stirred for 1 hour. The insolubles are collected by filtration, washed twice with 100 ml portions of isopropyl ether and once with 100 ml of water, and dried. Recrystallization from acetone-ethanol (10:1) gives 5.7 g of benzothiazol-2-ylthioethyl 2-(2-formamidothiazol- 4-yl)-(Z)-2-methoxyiminoacetate as light yellow needles melting at 172° to 173° C.

IR(KBr)cm$^{-1}$: 3140, 3040, 2930, 1690

NMR(d$_6$-DMSO)δ: 4.02 (3H, s), 7.66 (1H, s), 8.52 (1H, s).

Elemental analysis: $C_{14}H_{10}N_4O_3S_3$: Calcd.(%): C, 44.43; H, 2.66; N, 14.80. Found (%): C, 44.63; H, 2.71; N, 14.46.

Then, 1.15 g of 7β-amino-3-hydroxymethyl-3-cephem-4-carboxylic acid is suspended in 18 ml of water and the suspension is adjusted to pH 7.5 with 1N aqueous sodium hydroxide solution, whereupon a clear solution is obtained. To this solution are added 1.92 g of the above thioester and 32 ml of THF and the mixture is stirred at room temperature for 6 hours. The THF is distilled off under reduced pressure and the residual aqueous solution is washed with 30 ml of ethyl acetate and filtered. The filtrate is subjected to XAD-II (200 ml) column chromatography. After the column is washed with water, elution is carried out with 500 ml of 10% (v/v) ethanol and the eluate is concentrated under reduced pressure and freeze-dried to give 1.98 g of sodium 7β-[2-(2-formamidothiazol-4-yl)-(Z)-2-methoxyiminoacetamido]-3-hydroxymethyl-3-cephem-4-carboxylate as colorless powders.

IR(KBr)cm$^{-1}$: 3275, 2950, 1760, 1675, 1600.

NMR(d$_6$-DMSO)δ: 3.89 (3H, s), 4.02 (2H, ABq), 7.39 (1H, s), 8.52 (1H, s).

Elemental analysis: $C_{15}H_{14}N_5NaO_7S_2 \cdot 2H_2O$. Calcd.(%): C, 36.07; H, 3.63; N, 14.02. Found (%): C, 36.39; H, 3.60; N, 14.33.

Reference Example 6

In 15 ml of water is suspended 2.37 g of 7β-amino-3-hydroxymethyl-3-cephem-4-carboxylic acid. Under ice-cooling and stirring 3 ml of triethylamine is added, followed by addition of 4.5 g of di-tert-butyl bicarbonate and 15 ml of dioxane. The mixture is stirred at room temperature for 16 hours, after which 2.18 g of di-tert-butyl bicarbonate and 1.4 ml of triethylamine are further added. The mixture is further stirred for 16 hours. The reaction mixture is diluted with water and ethyl acetate and the water layer is separated and adjusted to pH 2 with diluted hydrochloric acid under ice-cooling. The solution is extracted with ethyl acetate and the extract is washed with aqueous sodium chloride solution and dried over magnesium sulfate. This solution is added to a solution of 2.9 ml of triethylamine in 50 ml of dichloromethane and the solvent is distilled off under reduced pressure. The solid residue is dried to give 3.18 g of 7β-tert-butoxycarbonylamino-3-hydroxymethyl-3-cephem-4-carboxylic acid triethylamine salt as yellow foamy powders.

IR(KBr)cm$^{-1}$: 3300 (br), 1770, 1710, 1600.

NMR(d$_6$-DMSO)δ: 1.13 (9H, t, J=7Hz), 1.39 (9H, s), 4.08 (2H, ABq).

REFERENCE EXAMPLE 7

In 50 ml of water is suspended 2.30 g of 7β-amino-3-hydroxymethyl-3-cephem-4-carboxylic acid and the suspension is adjusted to pH 8.5 with 1N-aqueous sodium hydroxide solution, whereupon a clear solution is obtained. To this solution are added 4.56 g of S-p-methoxybenzyloxycarbonyl-4,6-dimethyl-2-mercaptopyridine and 50 ml of dioxane and the mixture is stirred at room temperature for 7 hours. The reaction mixture is diluted with water and ethyl acetate and the water layer is separated and concentrated under reduced pressure. The residue is subjected to XAD-II (500 ml) column chromatography and after the column is washed with water, elution is carried out with 10% (v/v) ethanol. The eluate is concentrated under reduced pressure and freeze-dried to give 1.63 g of sodium 7β-(p-methoxybenzyloxycarbonylamino)-3-hydroxymethyl-3-cephem-4-carboxylate as colorless powders.

IR(KBr)cm$^{-1}$: 1760, 1695, 1610.

NMR(d$_6$-DMSO)δ: 3.76 (3H, s), 4.02 (2H, ABq), 5.02 (2H, s).

Elemental analysis: $C_{17}H_{17}N_2NaO_7S \cdot \frac{1}{2}H_2O$. Calcd.(%): C, 48.00; H, 4.26; N, 6.59. Found (%): C, 47.78; H, 4.08; N, 6.77.

REFERENCE EXAMPLE 8

In 106 ml of dichloromethane are suspended 3.1 g of triphenylphosphine and 3.93 g of 2,2'-dithiobis(benzothiazole) and the suspension is stirred at room temperature for 30 minutes. Then, with ice-cooling, 1.49 g of 2-(5-amino-1,2,4-thiadiazol-3-yl)-(Z)-2-ethoxyiminoacetic acid is added and the mixture is stirred for 15 hours. The reaction mixture is then filtered and the filtrate is concentrated under reduced pressure. The residue is subjected to silica gel (50 g) column chromatography and elution is carried out with ethyl acetate-hexane (2:1). By the above procedure there is obtained S-(2-benzothiazolyl) 2-(5-amino-1,2,4-thiadiazol-3-yl)-(Z)-2-ethoxyiminothioacetate as light yellow crystals.

IR(KBr)cm$^{-1}$ 3375, 3260, 3120, 2980, 1700, 1620.
NMR(CDCl$_3$+d$_6$-DMSO)δ: 1.35 (3H, t, J=7 Hz), 4.37 (2H, q, J=7 Hz), 7.21 (2H, s)

In the same manner as above, the following compound is produced. S-(2-Benzothiazolyl) 2-(5-amino-1,2,4-thiadiazol-3-yl)-(Z)-2-methoxyiminothioacetate
NMR(d$_6$-DMSO)δ: 4.04 (3H, s), 8.31 (2H, s).

REFERENCE EXAMPLE 9

In 50 ml of ethanol is suspended 1.48 g of cysteamine hydrochloride. Then, with ice cooling, 1.04 g of sodium hydride (oily, 60 wt.%) is added and the mixture is stirred for 10 minutes. Then, 1.54 g of 6-chloroimidazo[1,2-b]pyridazine is added and the mixture is stirred at room temperature for 1 hour and further at 45° C. for 4 hours. The solvent is then distilled off under reduced pressure and the residue is shaken well with chloroform and saturated aqueous sodium hydrogen carbonate solution. The chloroform layer is separated and dried over magnesium sulfate and the solvent is distilled off under reduced pressure. The residue is subjected to silica gel (80 g) column chromatography and after the column is washed with ethyl acetate and acetonitrile-water (1:1), elution is carried out with acetonitrile-water-triethylamine (20:5:1). The eluate is concentrated to 20 ml under reduced pressure, and 20 ml of ethanol and 2.18 g of di-tert-butyl bicarbonate are added to the residual aqueous solution. After 30 minutes' stirring at room temperature, the ethanol is distilled off under reduced pressure. The residue is diluted with saturated aqueous sodium hydrogen carbonate solution and extracted with chloroform. The extract is dried over magnesium sulfate and the solvent is distilled off under reduced pressure. The residue is subjected to silica gel (80 g) column chromatography and after the column is washed with chloroform, elution is carried out with ethyl acetate. The procedure gives 2.29 g of 6-(2-tert-butoxycarbonylaminoethylthio)imidazo[1,2-b]pyridazine as colorless powders.

IR(KBr)cm$^{-1}$: 3250, 3060, 2890, 1708.
NMR(CDCl$_3$)δ: 1.43 (9H, s), 6.83 (1H, d, J=10 Hz), 7.74 (1H, d, J=10 Hz).

REFERENCE EXAMPLE 10

In 30 ml of ethanol is suspended 1.46 g of 2-hydroxyethylmercaptan. With ice-cooling, 897 mg of sodium hydride (oily, 60 wt.%) is added and the mixture is stirred for 10 minutes. Then, 1.91 g of 6-chloroimidazo[1,2-b]pyridazine is added and the mixture is stirred at room temperature for 6 hours. The solvent is distilled off under reduced pressure and the residue is shaken well with dichloromethane and water. The dichloromethane layer is separated and dried over magnesium sulfate and the solvent is distilled off under reduced pressure. The residue is subjected to silica gel (200 g) column chromatography and after the column is washed with ethyl acetate, elution is carried out with acetone. The fractions rich in the desired compound are pooled and the solvent is distilled off under reduced pressure. To the residue are added dichloromethane and isopropyl ether and the resulting pale-brown powder is collected by filtration. This procedure gives 500 mg of 6-(2-hydroxyethylthio)imidazo[1,2-b]pyridazine.

NMR(CDCl$_3$+d$_6$-DMSO)δ: 3.37 (2H, t, J=6 Hz), 3.87 (2H, q, J=6 Hz), 4.58 (1H, t, J=6 Hz), 6.91 (1H, d, J=10 Hz), 7.75 (1H, d, J=10 Hz)

REFERENCE EXAMPLE 11

In 100 ml of ethanol is suspended 2.95 g of cysteamine hydrochloride. With ice-cooling, 2.08 g of sodium hydride (oily, 60 wt.%) is added thereto and the mixture is stirred for 5 minutes. Then, 3.05 g of 5-chloroimidazo[1,2-a]pyridine[prepared by the process described in Journal of Heterocyclic Chemistry 2, 53-62 (1965) is added and the mixture is refluxed for 3 hours. After cooling, 6.55 g of di-tert-butyl bicarbonate is added and the mixture is stirred at room temperature for 30 minutes. The solvent is distilled off under reduced pressure and the residue is shaken with 100 ml of water and 150 ml of chloroform. The chloroform layer is separated, washed with water and dried over magnesium sulfate. The solvent is distilled off under reduced pressure and the residue is subjected to silica gel (90 g) column chromatography. After the column is washed with chloroform, elution is carried out with ethyl acetate to give 5.1 g of 5-(2-tertbutoxycarbonylaminoethylthio)imidazo[1,2-a]pyridine as light yellow powders melting at 105° to 107° C.

NMR(CDCl$_3$)δ: 1.42 (9H, s), 3.02–3.50 (4H, m), 4.93 (1H, br.), 6.92–7.30 (2H, m), 7.52–7.90 (3H, m)

Elemental analysis: C$_{14}$H$_{19}$N$_3$O$_2$S: Calcd. (%): C, 57.31; H, 6.53; N, 14.32. Found (%): C, 57.27; H, 6.53; N, 14.34.

REFERENCE EXAMPLE 12

A mixture of 4.61 g of 6-chloroimidazo[1,2-b]pyridazine, 18.03 g of ethylenediamine and 30.36 g of triethylamine is refluxed for 20 hours. The solvent is distilled off under reduced pressure and 50 ml of ethanol is added to the residue. The solvent is then distilled off again under reduced pressure. To the residue are added 150 ml of dichloromethane and 50 ml of water, followed by addition of 7.86 g of di-tert-butyl bicarbonate. The mixture is stirred at room temperature for 10 minutes. Then, 7.86 g of di-tert-butyl bicarbonate is further added and the mixture is stirred for 10 minutes. Then, the same amount of di-tert-butyl bicarbonate is further added, followed by 30 minutes' stirring. The dichloromethane layer is separated and dried over magnesium sulfate and the solvent is distilled off under reduced pressure. The residue is subjected to silica gel (150 g) column chromatography and after development with dichloromethane, elution is carried out with ethyl acetate-ethanol (10:1). The solvent is distilled off under reduced pressure to give 5.88 g of 6-(2-tertbutoxycarbonylaminoethylamino)imidazo[1,2-b]pyridazine as light blue powders.

IR(KBr)cm$^{-1}$: 3370, 3230, 3050, 2990, 1685, 1630.
NMR(CDCl$_3$): 1.43 (9H, s), 3.30–3.57 (4H, m), 5.13 (1H, br. s), 5.30 (1H, br. s), 6.37 (1H, d, J=9.5 Hz), 7.57 (1H, d, J=9.5 Hz), 7.47 (1H, s), 7.62 (1H, s)

REFERENCE EXAMPLE 13

To 24 g of ethylenediamine is added 9.34 g of 5-chloroimidazo[1,2-a]pyridine hydrobromide and the mixture is refluxed for 22 hours. The excess ethylenediamine is distilled off under reduced pressure and the residue is dissolved in a mixture of 150 ml of water and 150 ml of ethanol. Then, 26.2 g of di-tert-butyl bicarbonate is added at room temperature and the mixture is stirred for 2 hours. Then, 13.1 g of di-tert-butyl bicarbonate is further added and the mixture is stirred for 1 hour. The reaction mixture is filtered and washed with water. The filtrate and washings are combined and extracted with 200 ml of dichloromethane. The extract is dried over magnesium sulfate and concentrated under reduced pressure. The residue is subjected to silica gel (300 g) column chromatography and elution is carried out with ethyl acetate. The eluate is concentrated under reduced pressure to give 6.28 g of 5-(2-tert-butoxycarbonylaminoethylamino)imidazo[1,2-a]pyridine as a yellow foamy product.

IR(KBr)cm$^{-1}$: 1685, 1630.

NMR(CDCl$_3$)δ: 1.46 (9H, s), 3.24–3.67 (4H, m), 5.45 (1H, br. t, J=6 Hz), 5.75 (1H, dd, J=2, 6 Hz), 5.95 (1H, br. s), 6.97–7.20 (2H, m), 7.45–7.61 (2H, m)

REFERENCE EXAMPLE 14

In 50 ml of dimethylformamide is dissolved 7.41 g of ethyl 2-(2-tritylaminothiazol-4-yl)-(Z)-2-hydroxyiminoacetate hydrochloride and with stirring at room temperature, 4.15 g of potassium carbonate and 2.75 g of 1-bromo-2-(2-methoxyethoxy)ethane are added. The mixture is stirred for 48 hours, after which it is poured into 500 ml of ice water and extracted with ethyl acetate. The extract is washed with water, dried over magnesium sulfate and concentrated under reduced pressure. The residue is chromatographed on silica gel (150 g) column and elution is carried out with hexane-ethyl acetate (1:1). The fractions rich in the desired compound are pooled and concentrated under reduced pressure to give 4.84 g of ethyl 2-(2-tritylaminothiazol4-yl)-(Z)-2-[2-(2-methoxyethoxy)ethoxyimino]acetate as a yellow foamy product.

IR (Neat) cm$^{-1}$: 3270, 2970, 2910, 2850, 1730.

NMR (CDCl$_3$)δ: 1.32 (3H, t, J=7Hz), 3.35 (3H, s), 3.4–3.8 (6H, m), 4.2–4.5 (4H, m), 6.48 (1H, s), 6.93 (1H, br.s), 7.30 (15H, br.s)

In a mixture of 4.9 ml of dioxane and 34 ml of ethanol is dissolved 4.81 g of the above product, followed by addition of 4.9 ml of 2N aqueous sodium hydroxide solution. The mixture is stirred at room temperature for 20 hours, after which 0.5 ml of dioxane and 0.5 ml of 2 N aqueous sodium hydroxide solution are further added. After stirring for another 48 hours, 300 ml of ether is added to the reaction mixture. Precipitated crystals are collected by filtration, washed with ether and dissolved in water. Under cooling with ice-water, the solution is adjusted to pH 2.0 and extracted with ethyl acetate. The extract is washed with water, dried over magnesium sulfate and concentrated under reduced pressure. A mixture of ethyl acetate and hexane (1:3) is added to the residue and the resulting powders are collected by filtration to give 4.59 g of 2-(2-tritylaminothiazol-4-yl)-(Z)-2-[2-(2-methoxyethoxy)ethoxyimino]acetic acid.

Melting point, 113°–117° C. (decomposition).

IR (KBr) cm$^{-1}$: 3380, 3250, 2910, 1700.

NMR (d$_6$-DMSO) δ:3.23 (3H, s), 3.4–3.7 (6H, m), 4.13 (2H, t, J=5 Hz), 6.78 (1H, s), 7.30 (15H, br.s), 8.75 (1H, br.s).

Elemental analysis: C$_{29}$H$_{29}$N$_3$O$_5$S.0.5H$_2$O. Calcd. (%): C, 64.42; H. 5.59; N, 7.77. Found (%): C, 64.15; H, 5.58: N, 7.58.

REFERENCE EXAMPLE 15

14.04 g of 28% (w/w) sodium methoxide solution is diluted with 60 ml of methanol and, with ice-cooling and stirring, 4.14 g of cysteamine hydrochloride and 5.07 g of 6-chloroimidazo[l,2-b]pyridazine are added to the solution, and the mixture is refluxed for 4 hours. After cooling, methanol is distilled off under reduced pressure and the residue is dissolved in a mixture of 100 ml of water and tetrahydrofuran (1:1). With ice-cooling and stirring, 3.36 g of sodium hydrogen carbonate and 1.87 g of 2-methylsulfonylethoxycarbonyl chloride are added to the solution and the mixture is stirred for 2 hours. Then, 0.84 g of sodium hydrogen carbonate and 1.87 g of 2-methylsulfonylethoxycarbonyl chloride are added and under ice-cooling, the mixture is stirred for 1 hour. The reaction mixture is extracted with chloroform and the extract is dried over magnesium sulfate and concentrated under reduced pressure. The residue is column-chromatographed on silica gel (250 g) and after the column is washed with ethyl acetate, elution is carried out with ethyl acetate-ethanol (4:1). The eluate is concentrated under reduced pressure and to the residue are added hexane and a small amout of dichloromethane. The resulting colorless powders are collected by filtration to give 9.13 g of 6-[2-(2-methylsulfonylethoxycarbonylamino)ethylthio]imidazo[1,2-b]pyridazine.

mp. 91° to 93° C.

IR (KBr) cm$^{-1}$: 3330, 3130, 1690.

NMR (d$_6$-DMSO)δ: 3.02 (3H, s), 3.2–3.6 (6H, m), 4.32 (2H, t, J=6Hz), 7.10 (1H, d, J=10 Hz), 7.59 (1H, br.s), 7.67 (1H, d, J=1 Hz), 7.95 (1H, d, J=10 Hz), 8.12 (1H, d, J=1 Hz).

Elemental analysis: C$_{12}$H$_{16}$N$_4$O$_4$S$_2$·0.3H$_2$O. Calcd. (%): C, 41.20; H, 4.78; N, 16.02. Found (%): C, 41.25; H, 4.63; N, 15.77.

REFERENCE EXAMPLE 16

In 15 ml of dimethylformamide are dissolved 1.25 g of sodium 7β-(p-methoxybenzyloxycarbonylamino)-3-hydroxymethyl-3-cephem-4-carboxylate and 2.76 g of 6-[2-(2-methylsulfonylethoxycarbonylamino)ethylthio]imidazo[1,2-b]pyridazine. After the solution is cooled to −30° C., 2.0 g of ethyl o-phenylenephosphate is added and the mixture is stirred for 1 hour, with the temperature being gradually raised t 0° C. The reaction mixture is concentrated under reduced pressure and the residue is subjected to silica gel (120 g) column chromatography. After the column is washed with acetonitrile, elution is carried out with acetonitrile-water (5:1). The eluate is concentrated under reduced pressure and the residual aqueous solution is freeze-dried to give 1.55 g of colorless powders. In a mixture of 3 ml of anisole and 30 ml of dichloromethane is suspended 1.40 g of the above powders. With ice-cooling and stirring, 30 ml of trifluoroacetic acid is added to the suspension and the resultant mixture is stirred with ice-cooling for 30 minutes. Following addition of 30 ml of toluene to the reaction mixture, the mixture is concentrated under reduced pressure. Water and dichloromethane are added to the residue and the mixture is shaken. The water layer is separated, adjusted to pH 3.0 and concentrated under reduced pressure. The residue is subjected to column chromatography on XAD-II (400 ml). After the column is washed with water, elution is carried out with 20% (v/v) ethanol. The eluate is concentrated under reduced pressure and freeze-dried to give 0.71 g of 7β-amino-3-[[6-[2-(2-methylsulfonylethoxycarbonylamino)ethylthio]imidazo[1,2-b]pyridazinium- 1-yl]methyl]-3-cephem-4-carboxylate as colorless powders.

IR (KBr) cm$^{-1}$: 1765, 1710, 1610.

NMR (D$_2$O)δ: 3.27 (3H, s), 3.2–3.9 (8H, m), 4.65 (2H, t, J=5 Hz), 5.01 (1H, d, J=5 Hz), 5.32 (1H, d, J=5 Hz), 5.52 (2H, br.s), 7.92 (1H, d, J=10 Hz), 8.33 (1H, d, J=2 Hz), 8.52 (1H, d, J=2 Hz), 8.60 (1H, d, J=10 Hz).

Elemental analysis: $C_{20}H_{24}N_6O_7S_3 \cdot 2.3H_2O$. Calcd. (%): C, 40.16; H, 4.82; N, 14.05. Found (%): C, 40.11; H, 4.60; N, 13.88.

REFERENCE EXAMPLE 17

In a mixture of 100 ml of water and 100 ml of tetrahydrofuran are dissolved 8.76 g of 3-bromopropylamine hydrochloride and 6.72 ml of triethylamine. After addition of 8.73 g of di-tert-butyl bicarbonate, the mixture is stirred at room temperature for 16 hours. The reaction mixture is extracted with ethyl acetate, and the extract is washed with water, 5% aqueous citric acid solution and aqueous sodium chloride solution in that order and then dried over magnesium sulfate. The solvent is then distilled off under reduced pressure to give a light yellow oil. This is dissolved in 80 ml of dimethyl sulfoxide. To the solution are added 8.12 g of ethyl 2-(2-aminothiazol-4-yl)-(Z)-2-hydroxyiminoacetate and 16.56. g of potassium carbonate, and the mixture is stirred at 60° C. for 5 hours. After cooling, the reaction mixture is poured into 800 ml of ice-water and extracted with dichloromethane. The extract is washed with aqueous potassium carbonate solution and aqueous sodium chloride solution, dried over magnesium sulfate and concentrated under reduced pressure. The residue is subjected to silica gel (250 g) column chromatography, elution being carried out with hexane-ethylacetate (2:3). The fractions rich in the desired compound are collected and concentrated under reduced pressure to give 5.27 g of ethyl 2-(2-aminothiazol-4-yl)-(Z)-2-(3-tert-butoxycarbonylaminopropoxyimino)acetate as a yellow foamy product.

IR (KBr) cm$^{-1}$: 3330, 3130, 2980, 2930, 1730, 1690.

NMR (d$_6$-DMSO) δ: 1.27 (3H, t, J=7 Hz), 1.37 (9H, s), 1.5–1.9 (2H, m), 2.97 (2H, q, J=7 Hz), 4.07 (2H, t, J=7 Hz), 4.28 (2H, q, J=7 Hz), 6.70 (1H, br.s), 6.82 (1H, s), 7.17 (2H, br.s).

REFERENCE EXAMPLE 18

In a mixture of 15 ml of dimethylacetamide and 15 ml of dichloromethane are dissolved 5.17 g of ethyl 2-(2-aminothiazol-4-yl)-(Z)-2-(3-tert-butoxycarbonylaminopropoxyimino)acetate and 1.1 ml of pyridine and, under ice-cooling and stirring, 2.21 ml of chloroacetyl chloride is added dropwise. With ice-cooling, the mixture is stirred for 30 minutes and the reaction mixture is poured into 150 ml of ice-water and extracted with dichloromethane. The extract is washed with water, aqueous sodium hydrogen carbonate solution and aqueous sodium chloride solution in that order and dried over magnesium sulfate. The solvent is distilled off under reduced pressure and the residue is subjected to silica gel (200 g) column chromatography, elution being carried out with chloroform-ethyl acetate (9:1 and 5:1). Fractions containing the desired compound are collected and concentrated under reduced pressure. The residue is dissolved in a mixture of 8.8 ml of dioxane and 62 ml of ethanol, followed by addition of 8.8 ml of 2 N aqueous sodium hydroxide solution. The mixture is stirred at room temperature for 48 hours and, then, 1.2 ml of 2 N aqueous sodium hydroxide solution is added and stirring is continued for 6 hours. The reaction mixture is concentrated under reduced pressure and the residue is dilluted with water and washed with ethyl acetate. The solution is adjusted to pH 2.0 with diluted hydrochloric acid and extracted with ethyl acetate. The extract is washed with aqueous sodium chloride solution and dried over magnesium sulfate. The solvent is distilled off under reduced pressure and a mixture of hexane and ethyl acetate (4:1) is added to the residue. The resulting light yellow powder is collected by filtration to give 2.47 g of 2-(2-chloroacetamidothiazol-4-yl)-(Z)-2-(3-tert-butoxycarbonylaminopropoxyimino)acetic acid.

mp. 127° to 132° C.(dec.).

IR (KBr) cm$^{-1}$: 3340, 3180, 2980, 2930, 1710–1680, 1570, 1520.

NMR (d$_6$-DMSO) δ: 1.38 (3H, s), 1.5–1.85 (2H, m), 3.00 (2H, q, J=7 Hz), 4.13 (2H, t, J=7 Hz), 4.36 (2H, s), 6.55–6.85 (1H, br.s), 7.53 (1H, s), 12.93 (1H, br.s)

Elemental analysis: $C_{15}H_{21}N_4O_6ClS$. Calcd. (%): C, 42.81; H, 5.03; N, 13.31. Found (%): C, 43.14; H, 5.15; N, 13.41.

REFERENCE EXAMPLE 19

In 50 ml of water is suspended 4.60 g of 7β-amino-3-hydroxymethyl-3-cephem-4-carboxylic acid and, with ice-cooling and stirring, 20 ml of 1N aqueous sodium hydroxide solution is added to the suspension for dissolving the acid. To the solution is added 1.85 g of sodium hydrogen carbonate and, then, a solution of 4.11 g of 2-methylsulfonylethoxycarbonyl chloride in 40 ml of tetrahydrofuran is added dropwise. The mixtrue is stirred with ice-cooling for 2 hours, then adjusted to pH 6.5, washed with ethyl acetate, and concentrated under reduced pressure. The residue is subjected to column chromatography on XAD-II (600 ml). Elution is performed with water and the eluate is concentrated under reduced pressure and freeze-dried to give 3.10 g of sodium 7β-(2-methylsulfonylethoxycarbonylamino)-3-hydroxymethyl-3-cephem-4-carboxylate as light yellow powders.

IR (KBr) cm$^{-1}$: 1760, 1710, 1600, 1540.

NMR (D$_2$O) δ: 3.36 (3H, s), 3.4–4.05 (4H, m), 4.56 (2H, s), 5.30 (1H, d, J=5 Hz), 5.70 (1H, d, J=5 Hz)

Elemental analysis: $C_{12}H_{15}H_2O_8NaS_2 \cdot 1.5H_2O$. Calcd. (%): C, 33.57; H, 4.23; N, 6.52. Found (%): C, 33.67; H, 4.57; N, 6.69.

REFERENCE EXAMPLE 20

In a mixture of 30 ml of dimethylformamide and 15 ml of acetonitrile are dissolved 3.00 g of sodium 7β-(2-methylsulfonylethoxycarbonylamino)-3-hydroxymethyl-3-cephem-4-carboxylate and 4.41 g of 6(2-tert-butoxycarbonylaminoethylthio)imidazo[1,2-b]-pyridazine. At −30° C., 3.73 g of ethyl o-phenylene phosphate is added and the mixture is stirred for 1 hour, the temperature being gradually raised to −5° C. The reaction mixture is concentrated under reduced pressure and the residue is subjected to silica gel (250 g) column chromatography. The column is washed with acetonitrile and elution is carried out with acetonitrile-water (4:1). The eluate is concentrated under reduced pressure and freeze-dried to give 2.77 g of light yellow powders. In 50 ml of water is dissolved 2.58 g of this product and at 8° C., 1N aqueous sodium hydroxide solution is added. The mixture is adjusted to pH 12.3 and, with the pH being maintained at 11.7–12.3, stirred at 8°–10° C. for 30 minutes. The solution is adjusted to pH 3.1 with 8 ml of 1N hydrochloric acid and subjected to column chromatography on XAD-II (400 ml). The column is washed with water and elution is carried out with 20% (v/v) ethanol. The eluate is concentrated under reduced pressure and freeze-dried to give 1.25 g of 78-amino-3-[[6-(2- tert-butoxycarbonylaminoethylthio)imidazo[1,2-b]pyridazinium-1-yl]methyl]-3-cephem-4-carboxylate as colorless powders.

IR (KBr) cm$^{-1}$: 2980, 2930, 1760, 1695, 1610.

NMR (D$_2$O) δ: 1.51 (9H, s), 3.84 (2H, ABq, J=18 Hz), 3.45-3.7 (4H, m), 5.00 (1H, d, J=5 Hz), 5.25 (1H, d, J=5 Hz), 5.45 (2H, br.s), 7.88 (1H, d, J=10 Hz), 8.28 (1H, d, J=2 Hz), 8.48 (1H, d, J=2 Hz), 8.56 (1H, d, J=10 Hz).

REFERENCE EXAMPLE 21

In 10 ml of dimethylformamide is suspended 0.976 g of S-cyanomethylisothiourea hydrochloride prepared according to the method described in Japanese Published Unexamined Patent Application No. 50-154279. Under cooling at −35° C. and stirring, 2.73 g of 28% (w/w) sodium methylate solution is added dropwise, after which the mixture is stirred at −40° C. to −35° C. for 10 minutes. Then, a solution of 3.94 g of ethyl 2-(2-tritylaminothiazol-4-yl)-(Z)-2-(2-iodoethoxyimino)acetate in 10 ml of dimethylformamide is added at the same temperature. The mixture is stirred at or below −30° C. for 5 minutes and then under ice-cooling for 4 hours. The reaction mixture is poured into 400 ml of ice-water and extracted with ethyl acetate. The extract is washed with aqueous sodium chloride solution, dried over magnesium sulfate and concentrated under reduced pressure. To the solid residue is added a mixture of ether-petroleum ether (1:1) and the mixture is filtered to give 3.18 g of ethyl 2-(2-tritylaminothiazol-4-yl)-(Z)-2-(2-cyanomethylthioethoxyimino)acetate as light yellow crystals.

mp. 137° to 139° C.

IR (KBr) cm$^{-1}$: 3370, 2980, 2920, 2560, 1740.

NMR (d$_6$-DMSO) δ: 1.12 (3H, t, J=7 Hz), 2.90 (2H, t, J=6 Hz), 3.69 (2H, s), 3.96 (2H, q, J=7 Hz), 4.26 (2H, t, J=6 Hz), 6.93 (1H,s), 7.0-7.45 (15H, m), 8.73 (1H, s).

Elemental analysis: $C_{30}H_{28}N_4O_3S_2$. Calcd. (%): C, 64.72; H, 5.07; N, 10.06. Found (%): C, 64.74; H, 5.15; N, 9.92.

REFERENCE EXAMPLE 22

In a mixture of 40 ml of ethanol and 5 ml of dioxane is suspended 2.78 g of ethyl 2-(2-tritylaminothiazol-4-yl)-(Z)-2-(2-cyanomethylthioethoxyimino)acetate, followed by addition of 5 ml of 2N aqueous sodium hydroxide solution. The mixture is stirred at room temperature for 2 hours, at the end of which time 40 ml of ethanol and 80 ml of tetrahydrofuran are added. The mixture is further stirred at room temperature for 19 hours. The reaction mixture is concentrated under reduced pressure and 500 ml of ether is added to the residue (about 50 ml). The resulting crystals are collected by filtration and washed with ether. The crystals are dissolved in a mixture of water, tetrahydrofuran and ethyl acetate (1:1:2) and the solution is adjusted to pH 2 and shaken. The organic layer is separated, washed with aqueous sodium chloride solution and dried over magnesium sulfate. The solvent is distilled off under reduced pressure and a mixture of ether and petroleum ether (2:1) is added to the residue. The resulting powders are collected by filtration to give 2.14 g of 2-(2-tritylaminothiazol-4-yl)-(Z)-2-(2-cyanomethylthioethoxyimino)acetic acid as light yellow powders.

IR (KBr) cm$^{-1}$: 3060, 2930, 2250, 1720, 1590.

NMR (d$_6$-DMSO) δ: 2.92 (2H, t, J=6 Hz), 3.72 (2H, s), 4.26 (2H, t, J=6 Hz), 6.83 (1H, s), 7.1-7.5 (15H, m), 8.73 (1H, br.s).

Elemental analysis: $C_{28}H_{24}N_4O_3S_2 \cdot 0.4H_2O$. Calcd. (%): C, 62.75; H, 4.67; N, 10.46. Found (%): C, 62.74; H, 4.72; N, 10.44.

REFERENCE EXAMPLE 23

To 100 ml of dimethyl sulfoxide are added 10.35 g of ethyl 2-(2-aminothiazol-4-yl)-(Z)-2-hydroxyiminoacetate, 14.33 g of N-(4-bromobutyl)phthalimide and 21 g of potassium carbonate and the mixture is stirred at 55°-60° C. for 5 hours. After cooling, the reaction mixture is added to 1 l of ice-water and extracted with ethyl acetate. The extract is washed with aqueous potassium carbonate solution and aqueous sodium chloride solution, dried over magnesium sulfate, and concentrated under reduced pressure. The residue is subjected to silica gel (250 g) column chromatography and elution is carried out with hexane-ethyl acetate (1:1). The eluate is concentrated under reduced pressure to give 9.99 g of a yellow foamy product. In a mixture of 200 ml of ethanol and 50 ml of tetrahydrofuran is dissolved 9.50 g of the above product, followed by addition of 1.33 ml of hydrazine hydrate. The mixture is refluxed. Then, with 1.1 ml of hydrazine hydrate being added at every hour, the refluxing is continued for a total of 6 hours. The reaction mixture is then filtered and the filtrate is concentrated under reduced pressure. The residue is dissolved in a mixture of 250 ml of water and 250 ml of tetrahydrofuran, followed by addition of 25.0 g of di-tert-butyl bicarbonate and 7.0 ml of triethylamine. The mixture is stirred at room temperature for 4 hours, after which it is extracted with ethyl acetate. The extract is washed with aqueous sodium chloride solution and dried over magnesium sulfate. The solvent is distilled off under reduced pressure and the residue is subjected to silica gel (100 g) column chromatography. Elution is carried out with hexane-ethyl acetate (2:3) and the eluate is concentrated under reduced pressure to give 5.27 g of a yellow gum. A 3.80 g portion of this gum and 1.67 ml of triethylamine are dissolved in a mixture of 15 ml of dichloromethane and 10 ml of dimethylformamide and under ice-cooling and stirring, 3.26 g of trityl chloride is added in small portions. The mixture is stirred at room temperature for 4 hours, after which it is diluted with dichloromethane and added to ice-water. The dichloromethane layer is separated, washed with water and dried over sodium sulfate. The solvent is then distilled off under reduced pressure and the residue is subjected to silica gel (100 g) column chromatography. Then, elution is carried out with hexane-ethyl acetate (2:1 and 3:2) and the eluate is concetnrated under reduced pressure. The above procedure yields 4.52 g of ethyl 2-(2-tritylaminothiazol-4-yl)-(Z)-2-(4-tert-butoxycarbonylaminobutoxyimino)acetate as a light yellow foamy product.

IR (KBr) cm$^{-1}$: 3370, 2970, 2930, 1735, 1710, 1690, 1530.

NMR (d$_6$-DMSO) δ: 1.11 (3H, t, J=7 Hz), 1.37 (9H, s), 1.3-1.65 (4H, m), 2.89 (2H, q, J=6 Hz), 3.8-4.1 (4H, m), 6.65-6.8 (1H, m), 6.88 (1H, s), 7.1-7.45 (15H, m), 8.73 (1H, s)

Elemental analysis: $C_{35}H_{40}N_4O_5S$: Calcd. (%): C, 66.86; H, 6.41; N, 8.91. Found (%): C, 66.83; H, 6.55; N, 8.64.

REFERENCE EXAMPLE 24

In a mixture of 50 ml of ethanol and 7.1 ml of dioxane is dissolved 4.46 g of ethyl 2-(2-tritylaminothiazol-4-yl)-(Z)-2-(4-tert-butoxycarbonylaminobutoxyimino)acetate, followed by addition of 7.1 ml of 2 N-aqueous sodium hydroxide solution. The mixture is stirred at room temperature for 10 hours. To this reaction mixture was added 500 ml of ether and the resulting precipitates are collected by filtration. The precipitate is dissolved in water and under ice-cooling the solution is adjusted to p 2 with 3 N-HCl and extracted with ethyl acetate. The extract is washed with aqueous sodium chloride solution and dried over magnesium sulfate, and the solvent is distilled off under reduced pressure. To the residue is added ether-petroleum ether (1:3) and the resulting light yellow powders are collected by filtration. The above procedure yields 4.01 g of 2-(2-tritylaminothiazol-4-yl)-(Z)- 2-(4-tert-butoxycarbonylaminobutoxyimino)acetic acid.

mp. 120° to 124° C.

IR (KBr) cm$^{-1}$: 3370, 2970, 2930, 1710, 1695.

NMR (d$_6$-DMSO) δ: 1.36 (9H, s), 1.4–1.7 (4H, m), 2.90 (2H, q, J=6 Hz), 3.99 (2H, t, J=6 Hz), 6.55–6.75 (1H, m), 6.71 (1H, s), 7.15–7.45 (15 H, m), 8.72 (1H, br.s)

REFERENCE EXAMPLE 25

In the same manner as Reference Example 2, 7β-[2-(2-aminothiazol-4-yl)-(Z)-2-allyloxyiminoacetamido]-3-hydroxymethyl-3-cephem-4-carboxylic acid is obtained.

IR (KBr) cm$^{-1}$: 3530, 3260, 1770, 1660, 1550.

NMR (d$_6$-DMSO) δ: 3.53 (2H, s), 4.24 (2H, s), 4.58 (2H, d, J=5 Hz), 5.05–5.4 (3H, m), 5.65–6.2 (2H, m), 6.7 (1H, s,), 7.16 (2H, s), 9.57 (1H, d, J=9 Hz).

This compound is converted to the corresponding tri-n-butylamine salt in the same manner as Reference Example 2.

REFERENCE EXAMPLE 26

In 30 ml of 1,2-dichloroethane is suspended 1.5 g of 6-(2-hydroxyethylthio)imidazo[1,2-b]pyridazine and with stirring at room temperature, 1.94 g of dihydropyran and 193 mg of pyridinium p-toluenesulfonate are added. The mixture is stirred at 65° C. for 4 hours, after which 1.5 g of dihydropyran and 100 mg of pyridinium p-toluenesulfonate are further added. The mixture is stirred for an additional 4 hours. After cooling, the reaction mixture is washed with 30 ml portions of water three times, dried over sodium sulfate, and concentrated under reduced pressure. The residue is subjected to silica gel (100 g) column chromatography and elution is carried out with ethyl acetate. The eluate is concentrated under reduced pressure to give 1.85 g of 6-[2-(2-tetrahydropyranyloxy)ethylthio]imidazo[1,2-b]pyridazine as colorless crystals melting at 60° to 62° C.

IR (KBr) cm$^{-1}$: 3110, 2920, 2860, 1600, 1530.

NMR (CDCl$_3$) δ: 1.35–2.0 (6H, m), 3.35–4.2 (6H, m), 4.6–4.75 (1H, m), 6.8–7.9 (4H, m)

Elemental analysis: C$_{13}$H$_{17}$N$_3$O$_2$S: Calcd. (%): C, 55.89; H, 6.13; N, 15.04. Found (%): C, 55.86; H, 6.11; N,. 14.93.

REFERENCE EXAMPLE 27

To 20 ml of 3 N-hydrochloric acid is added 2.94 g of 6-(2-tert-butoxycarbonylaminoethylthio)imidazo[1,2-b]pyridazine and the mixture is stirred at room temperature for 1.5 hours. Then, a solution of 4.06 g of potassium cyanate in 40 ml of water is added dropwise over 15 minutes with stirring at 35° C. and the mixture is further stirred at the same temperature for 1 hour and at 60° C. for 1 hour. To the reaction mixture are added 2.5 ml of acetic acid and 2.43 g of potassium cyanate and the mixture is stirred at 60° C. for 1 hour. Then, 20 ml of a saturated aqueous solution of sodium hydrogen carbonate and 20 ml of water are added and the mixture is cooled. The resulting crystals are collected by filtration, rinsed and dried to give 2.08 g of 6-(2-carbamoylaminoethylthio)imidazo[1,2-b]pyridazine as colorless crystals melting at 216° to 217° C.

IR (KBr) cm$^{-1}$: 3400, 3300, 1660, 1560, 1530.

NMR (d$_6$-DMSO) δ: 5.49 (2H, br.s), 6.15–6.35 (1H, m), 7.08 (1H, d, J=9 Hz), 7.65 (1H, br.s), 7.82 (1H, d, J=9 Hz), 8.12 (1H, br.s).

Elemental analysis: C$_9$H$_{11}$N$_5$OS·0.2H$_2$O: Calcd. (%): C, 44.88; H, 4.77; N, 29.07. Found (%): C, 45.18; H, 4.57; N, 29.35.

REFERENCE EXAMPLE 28

Sodium sulfide (Na$_2$S·9H$_2$O) (112.5 g) is melted at 75°–85° C. and saturated with hydrogen sulfide while stirring at the same temperature. Then, with stirring at the same temperature, 42.0 g of 3-chloropropanol is added dropwise and the mixture is further stirred at the same temperature for 30 minutes.

While the reaction mixture is stirred under ice-cooling, 30 ml of acetic acid is added dropwise and the mixture is extracted with 500 ml of ether. The extract is washed with 150 ml portions of water twice, dried over sodium sulfate, and concentrated under reduced pressure. The residue is distilled under reduced pressure to give 13.2 g of 3-mercaptopropanol as a colorless oil boiling at 80° to 82° C. (15 mm Hg). In 147 ml of ethanol is dissolved 9.03 g of this product and with ice-cooling and stirring, 3.92 g of sodium hydride (oily, 60 wt.%) is added in small portions. Then, 7.53 g of 6-chloroimidazo[1,2-b]pyridazine is added and the mixture is refluxed for 2.5 hours. The ethanol is distilled off under reduced pressure and 500 ml of dichloromethane is added to the residue. After stirring, the insolubles are filtered off. The filtrate is washed with 300 ml of a saturated aqueous solution of sodium chloride, dried over sodium sulfate, and concentrated under reduced pressure. To the solid residue is added 100 ml of ether and after stirring, the crystals are collected by filtration. The crystals are suspended in 100 ml of 1,2-dichloroethane, followed by addition of 7.0 g of dihydropyran and 700 mg of pyridinium p-toluenesulfonate. The mixture is stirred at 65° C for 15 hours. Then, 5.0 g of dihydropyran and 500 mg of pyridinium p-toluenesulfonate are further added, and the mixture is stirred at 65° C. for 5 hours. After cooling, the reaction mixture is washed with 150 ml portions of water three times and the organic layer is dried over sodium sulfate and concentrated under reduced pressure. The residue is subjected to silica gel (150 g) column chromatography and elution is carried out with ethyl acetate. The eluate is concentrated under reduced pressure to give 6- [3-(2-tetrahydropyranyloxy)propylthio]imidazo[1,2-b]pyridazine as a colorless syrup. IR (Neat) cm$^{-1}$: 3080, 2930, 2860, 1600, 1530.

NMR (CDCl$_3$) δ: 1.4–2.25 (8H, m), 3.2–4.3 (6H, m), 4.55–4.7 (1H, m), 6.8–7.9 (4H, m)

REFERENCE EXAMPLE 29

In a mixture of 30 ml of dichloromethane and 10 ml of dimethylformamide is dissolved 500 mg of 6-(2-hydroxyethylthio)imidazo[1,2-b]pyridazine, followed by addition of 2 drops of triethylamine. Then, with stirring and cooling at −20° C., 490 mg of chloroacetyl isocyanate is added dropwise. Thereafter, the mixture is stirred at −20° to −10° C. for 1 hour. The dichloromethane is distilled off under reduced pressure and the residual solution is subjected to silica gel (100 g) column chromatography, with elution being carried out with ethyl acetate. The eluate is concentrated under reduced pressure. To the solid residue is added 5 ml of water and after stirring, the crystals are collected by filtration. The crystals are washed with 5 ml each of water and ether and dried. The above procedure yields 6-[2-(N-chloroacetylcarbamoyloxy)ethylthio]imidazo[1,2-b]pyridazine as crystals melting at 190° to 195° C.

IR (KBr) cm$^{-1}$: 3090, 2920, 2825, 2700, 1740, 1710, 1690.

NMR (d$_6$-DMSO) δ: 3.50 (2H, t, J=7 Hz), 4.43 (2H, s), 7.13 (1H, d, J=10 Hz), 7.70 (1H, s), 7.99 (1H, d, J=10 Hz), 8.16 (1H, s).

REFERENCE EXAMPLE 30

In 30 ml of ethanol is dissolved 3 g of 6-[[3-(2-tetrahydropyranyloxy)propylthio]imidazo[l,2-b]pyridazine, followed by addition of 45 ml of 1 N-hydrochloric acid. The mixture is stirred at room temperature for 15 hours. With ice-cooling, the reaction mixture is adjusted to pH 7.0 with 10% aqueous sodium hydroxide solution and concentrated to 20 ml under reduced pressure. The residue is extracted with 150 ml of dichloromethane and the extract is dried over sodium sulfate and concentrated under reduced pressure to give 6-(3-hydroxypropylthio)imidazo[1,2-b]pyridazine as colorless crystals melting at 108° to 109° C.

IR (KBr) cm$^{-1}$: 3200, 3100, 2925, 2875, 1605, 1535.

NMR (d$_6$-DMSO) δ: 1.7–2.0 (2H, m), 3.23 (2H, t, J=7 Hz), 3.4–3.7 (2H, m), 4.59 (1H, t, J=5 Hz), 7.09 (1H, d, J=9 Hz), 7.67 (1H, s), 7.95 (1H, d, J=9 Hz), 8.17 (1H, s).

REFERENCE EXAMPLE 31

In the same manner as Reference Example 29, 6-[3-(N-chloroacetylcarbamoyloxy)propylthio]imidazo[1,2-b]pyridazine is obtained as light yellow crystals melting at 133° to 134° C.

IR (KBr) cm$^{-1}$: 3130, 3075, 2950, 2825, 2700, 1740, 1720, 1700.

NMR (d$_6$-DMSO) δ: 1.9–2.2 (2H, m), 4.23 (2H, t, J=6 Hz), 4.46 (2H, s), 7.08 (1H, d, J=9 Hz), 7.67 (1H, s), 7.95 (1H, d, J=9 Hz), 8.15 (1H, s)

Elemental analysis: $C_{12}H_{13}N_4O_3ClS$. Calcd. (%): C, 43.84; H, 3.99; N, 17.04. Found (%): C, 43.84; H, 4.02; N, 16.80.

REFERENCE EXAMPLE 32

To 30 ml of ethanol is added 1.79 g of N-acetylcysteamine and with ice-cooling and stirring, 720 mg of sodium hydride (oily, 60 wt.%) is added. Then, 1.54 g of 6-chloroimidazo[1,2-b]pyridazine is further added and the mixture is stirred at 50° C. for 4 hours. The solvent is distilled off under reduced pressure and the residue is diluted with a saturated aqueous solution of sodium hydrogen carbonate and extracted with chloroform. The extract is dried over magnesium sulfate and the solvent is distilled off under reduced pressure. The residue is subjected to silica gel (50 g) column chromatography and after the column is washed with ethyl acetate, elution is carried out with acetone. The eluate is concentrated under reduced pressure to give 1.83 g of 6-(2-acetylaminoethylthio)imidazo[1,2-b]pyridazine as colorless powders.

IR (KBr) cm$^{-1}$: 3270, 3230, 3070, 1670, 1580.

NMR (CDCl$_3$) δ: 2.00 (3H, s), 3.25–3.8 (4H, m), 6.44 (1H, br.s), 6.85 (1H, d, J=10 Hz), 7.68 (1H, s), 7.75 (1H, d, J=10 Hz), 7.88 (1H, s)

REFERENCE EXAMPLE 33

To 100 ml of 3N-hydrochloric acid is added 5.89 g of 6-(2-tert-butoxycarbonylaminoethylthio)imidazo[1,2-b]pyridazine and the mixture is refluxed with stirring for 20 minutes. The solvent is distilled off under reduced pressure and the residue is diluted with 50 ml of toluene and concentrated again under reduced pressure. To the residue is added ether and the resulting powers are collected by filtration and washed with ether, ethanol and ether in the order mentioned to give 5.26 g of 6-(2-aminoethylthio)imidazo[1,2-b]pyridazine dihydrochloride as colorless powders.

NMR (D$_2$O) δ: 3.45–3.9 (4H, m), 7.82 (1H, d, J=10 Hz), 8.14 (1H, d, J=2 Hz), 8.33 (1H, d, J=10 Hz), 8.42 (1H, d, J=2 Hz).

Elemental analysis: $C_8H_{10}N_4S \cdot 2HCl \cdot 0.5H_2O$: Calcd. (%): C, 34.79; H, 4.74; N, 20.29. Found (%): C, 34.85; H, 4.69; N, 20.33.

REFERENCE EXAMPLE 34

To 50 ml of 3N aqueous sodium hydroxide solution is added 10.69 g of 6-(2-aminoethylthio)imidazo[1,2-b]pyridazine dihydrochloride and the mixture is stirred and, then, extracted with chloroform twice (150 ml and 50 ml). The extracts are combined and dried over magnesium sulfate and the solvent is distilled off under reduced pressure to give 7.55 g of 6-(2-aminoethylthio)imidazo[1,2-b]pyridazine as light yellow crystals.

On the other hand, 5.52 g of formic acid is added to 12.25 g of acetic anhydride at room temperature and the mixture is stirred at 45°–50° C. for 1 hour. After cooling, 60 ml of tetrahydrofuran and 5.83 g of the above-prepared crystals of 6-(2-aminoethylthio)imidazo[1,2-b]pyridazine are added and the mixture is stirred at room temperature for 1 hour. The solvent is distilled off under reduced pressure and the residue made basic with a saturated aqueous solution of sodium hydrogen carbonate. The precipitated crystals are collected by filtration to give 2.83 g of 6-(2-formylaminoethylthio)imidazo[1,2-b]pyridazine as colorless crystals melting at 148° to 151° C.

IR (KBr) cm$^{-1}$: 3250, 3030, 1670, 1535.

NMR (d$_6$-DMSO) δ: 3.1–3.65 (4H, m), 7.13 (1H, d, J=9.5 Hz), 7.71 (1H, s), 8.09 (1H, s), 8.18 (1H, s), 8.23 (1H, br.s).

Elemental analysis: $C_9H_{10}N_4OS$: Calcd. (%): C, 48.63; H, 4.53; N, 25.21. Found (%): C, 48.86; H, 4.56; N, 24.97.

REFERENCE EXAMPLE 35

In 20 ml of water is suspended 260 mg of 7β-amino-3-hydroxymethyl-3-cephem-4-carboxylic acid, and with ice-cooling and stirring, the suspension is adjusted to pH 7.0 with 1N-aqueous sodium hydroxide solution. After dissolution, 930 mg of 2-(2-tritylaminothiazol-4-yl)-(Z)-2-(trityloxyimino)acetic acid benzothiazol-2-ylthio ester, 20 ml of tetrahydrofuran, 20 ml of dioxane and 10 ml of acetonitrile are added and the mixture is stirred at room temperature for 38 hours. The reaction mixture is filtered and the filtrate is concentrated under reduced pressure. The residue is dissolved in 30 ml of tetrahydrofuran and the solution is subjected to silica gel (100 g) column chromatography. After the column is washed with acetonitrile (500 ml) and acetonitrile-water (19:1, 200 ml; 9:1, 200 ml), elution is carried out with 300 ml of acetonitrile-water (17:3). The eluate is concentrated under reduced pressure and the concentrate is freeze-dried to give 420 mg of sodium 7β-[2-(2-tritylaminothiazol-4-yl)-(Z)-2-(trityloxyimino)acetamido]-3-hydroxymethyl-3-cephem-4-carboxylate as light yellow powders.

IR (KBr) cm$^{-1}$: 3380, 1770, 1690, 1595.

NMR (d$_6$-DMSO) δ: 4.18 (2H, ABq, J=13 Hz), 5.00 (1H, d, J=5 Hz), 5.64 (1H, d.d, J=5, 8 Hz), 6.59 (1H, s) 7.0–7.45 (30H, m).

REFERENCE EXAMPLE 36

In the same manner as Reference Example 28, 3-mercaptopropanol is reacted with 5-chloroimidazo[1,2-a]pyridine and, then, the hydroxyl group is protected to give 5-[[3-(2-tetrahydropyranyloxy)propylthio]imidazo[1,2-a]pyridine as a light yellow syrup.

IR (Neat) cm$^{-1}$: 2930, 2850, 1615.

NMR (CDCl$_3$) δ: 1.4–2.1 (8H, m), 3.12 (2H, t, J=7 Hz), 3.35–4.0 (4H, m), 4.5–4.65 (1H, m), 6.9–7.85 (5H, m)

REFERENCE EXAMPLE 37

In 100 ml of ethanol is dissolved 6.25 g of 2-mercaptoethanol and with ice-cooling and stirring, 3.2 g of sodium hydroxide (oily, 60 wt.%) is added in small portions. Then, 6.1 g of 5-chloroimidazo[1,2-b]pyridine is added and the mixture is refluxed for 2.5 hours. After cooling, the reaction mixture is filtered and the filtrate is concentrated under reduced pressure. The residue is shaken with 200 ml of dichloromethane and 100 ml of saturated aqueous sodium chloride solution and the dichloromethane layer is separated, washed with 100 ml of saturated aqueous sodium chloride solution, dried over sodium sulfate, and concentrated under reduced pressure. To the solid residue is added 100 ml of ether and the mixture is stirred and filtered. The precipitates are washed with 30 ml of ether to give 6.55 g of 5-(2-hydroxyethylthio)imidazo[1,2-a]pyridine as colorless crystals melting at 99° to 100° C.

IR (KBr) cm$^{-1}$: 3120, 1615, 1530.

NMR (d$_6$-DMSO) δ: 3.19 (2H, t, J=7 Hz), 3.65 (2H, t, J=7 Hz), 5.05 (1H, br.s), 7.0–7.95 (5H, m)

Elemental analysis: C$_9$H$_{10}$N$_2$OS: Calcd. (%): C, 55.65; H, 5.19; N, 14.42. Found (%): C, 55.37; H, 4.95; N, 14.27.

REFERENCE EXAMPLE 38

In a mixture of 10 ml of dimethylformamide and 10 ml of dichloromethane is dissolved 1.94 g of 5-(2-hydroxyethylthio)imidazo[1,2-a]pyridine, followed by addition of 2 drops of triethylamine. Under cooling at −20° C. and stirring, 1.67 g of chloroacetyl isocyanate is added dropwise. The mixture is stirred at −20° to −10° C. for 30 minutes, after which 1 ml of methanol is added and the mixture is further stirred at −20° to −10° C. for 10 minutes. The reaction mixture is subjected to silica gel (140 g) column chromatography and elution is carried out with 1.5 l of ethyl acetate. The eluate is concentrated under reduced pressure and 30 ml of ether is added to the solid residue, followed by stirring. Filtration gives 1.33 g (42%) of 5-[2-(N-chloroacetylcarbamoyloxy)ethylthio]imidazo[1,2a]pyridine as colorless crystals with a melting point of 175° to 180° C. (decomp.).

IR (KBr) cm$^{-1}$: 3075, 3000, 2960, 2800, 2675, 1750, 1725, 1700, 1620.

NMR (d$_6$-DMSO) δ: 3.40 (2H, t, J=6 Hz), 4.30 (2H, t, J=6 Hz), 4.43 (2H, s), 7.1–8.0 (5H, m)

Elemental analysis: C$_{12}$H$_{12}$N$_3$O$_3$ClS: Calcd. (%): C, 45.94; H, 3.85; N, 13.39. Found (%): C, 46.05; H, 3.99; N, 13.17.

REFERENCE EXAMPLE 39

In the same manner as Reference Example 33, 5-(2-aminoethylthio)imidazo[1,2-a]pyridine dihydrochloride is obtained as colorless powders.

NMR (D$_2$O) δ: 3.3–3.8 (4H, m), 7.7–8.1 (3H, m), 8.16 (1H, d, J=2 Hz), 8.43 (1H, d, J=2 Hz)

Elemental analysis: C$_9$H$_{11}$N$_3$S.2HCl.0.2H$_2$O: Calcd. (%): C, 40.07; H, 5.01; N, 15.57. Found (%): C, 40.11; H, 4.88; N, 15.55.

REFERENCE EXAMPLE 40

In the same manner as Reference Example 34, 5-(2-formylaminoethylthio)imidazo[1,2-a]pyridine is obtained as colorless crystals melting at 104 to 106° C.

IR (KBr) cm$^{-1}$: 3200, 3020, 2980, 2860, 1675.

NMR (d$_6$-DMSO) δ: 3.05–3.55 (4H, m), 7.05–7.45 (2H, m), 7.60 (1H, d, J=8 Hz), 7.72 (1H, s), 7.98 (1H, s), 8.09 (1H, s), 8.28 (1H, br.s)

REFERENCE EXAMPLE 41

In the same manner as Reference Example 12, 6-(3-tert-butoxycarbonylaminopropylamino)imidazo[1,2-b]pyridazine is obtained as light yellow crystals melting at 134.5° to 136° C.

IR (KBr) cm$^{-1}$: 3370, 3270, 1690, 1625, 1580.

NMR (CDCl$_3$) δ: 1.46 (9H, s), 1.6–2.0 (2H, m), 3.22 (2H, q, J=6 Hz), 3.41 (2H, q, J=6 Hz), 4.8–5.35 (2H, m), 6.41 (1H, d, J=9.5 Hz), 7.46 (1H, s), 7.57 (1H, d, J=9.5 Hz), 7.63 (1H, s).

REFERENCE EXAMPLE 42

In the same manner as Reference Example 13, 5-(3-tert-butoxycarbonylaminopropylamino)imidazo[1,2-a]pyridine is obtained as light yellow powders.

IR (KBr) cm$^{-1}$: 3440, 3230, 1695, 1630, 1575.

NMR (d$_6$-DMSO) δ: 1.38 (9H, s), 1.6–2.0 (2H, m), 2.9–3.1 (4H, m), 5.88 (1H, d, J=8 Hz), 6.57 (1H, t, J=5.5 Hz), 6.87 (1H, d, J=9 Hz), 6.88 (1H, br.s), 7.17 (1H, dd, J=9.8 Hz), 7.53 (1H, s), 7.93 (1H, s).

REFERENCE EXAMPLE 43

To a mixture of 69.3 g of 10% (w/w) aqueous potassium hydroxide solution and 50 ml of dimethyl sulfoxide is added 8.85 g of S-(3-aminopropyl)isothiourea dihydrobromide and the mixture is stirred at room temperature for 1 hour. Then, 3.07 g of 6-chloroimidazo[1,2-b]pyridazine and 50 ml of ethanol are added. The mixture is stirred at room temperature for 6 hours, at the end of which time 9.82 g of di-tert-butyl bicarbonate and 20 ml of ethanol are added. The mixture is stirred at room temperature for 50 hours. The ethanol is distilled off under reduced pressure, and the residue is diluted with water and extracted twice with ethyl acetate (200 ml and 100 ml). The extracts are pooled, washed with water and aqueous sodium chloride solution and dried over magnesium sulfate. The solvent is distilled off under reduced pressure and the residue is subjected to silica gel (300 g) column chromatography. The column is washed with hexane-ethyl acetate (1:2) and elution is carried out with ethyl acetate. The eluate is concentrated under reduced pressure to give 3.45 g of 6-(3-tertbutoxycarbonylaminopropylthio)imidazo[1,2-b]pyridazine as a colorless oil.

IR (Neat) cm$^{-1}$: 3350, 2980, 2940, 1700, 1605.

NMR(CDCl$_3$)δ: 1.47(9H,s), 1.75–2.15(2H,m), 3.1–3.45(4H,m), 4.95(1H,br.s), 6.83(1H,d,J=10 Hz), 7.66(1H,s), 7.73(1H,d,J=10 Hz), 7.90(1H,s).

EXAMPLE 1

7β[2-(5-Amino-1,2,4-thiadiazol-3-yl)-(Z)-2-methoxyiminoacetamido]-3-[[6-(2-aminoethylthio)imidazo[1,2-b]pyridazinium-1-yl]methyl]-cephem-4-carboxylate trifluoroacetic acid salt

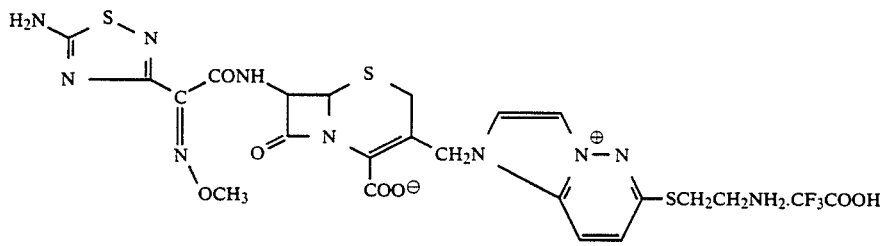

In 10 ml of dimethylformamide are dissolved 564 mg of sodium 7β-[2-(5-amino-1,2,4-thiadiazol-3-yl)-(Z)-2-methoxyiminoacetamido]-3-hydroxymethyl-3-cephem-4-carboxylate and 1.14 g of 6-(2-tert-butoxycarbonylaminoethylthio)imidazo[1,2-b]pyridazine. The solution is cooled to −20° C. and 1.293 g of ethyl o-phenylene phosphate is added. The mixture is stirred for 1 hour, with the temperature being raised gradually to 2° C. The reaction mixture is subjected to silica gel (100 g) column chromatography and after the column is washed with acetonitrile, elution is carried out with acetonitrile-water (6:1). The eluate is concentrated under reduced pressure and the residue is subjected to XAD-II (100 ml) column chromatography. The column is successively washed with water, 10% (v/v) ethanol and 20% (v/v) ethanol and elution is carried out with 30% (v/v) ethanol. The eluate is concentrated under reduced pressure and freeze-dried to give 299 mg of light yellow powder. In a mixture of 30 ml of dichloromethane and 2 ml of anisole is suspended 274 mg of the above product and 30 ml of trifluoroacetic acid is added. The mixture is stirred at room temperature for 1.5 hours. The solvent is distilled off under reduced pressure and 100 ml of ether is added to the residue. The crystals which separated out are collected by filtration, washed with ether, and dissolved in 20 ml of water. The solution is adjusted to pH 4.1 with 0.1N aqueous sodium hydroxide solution and subjected to XAD-II (100 ml) column chromatography. Elution is carried out with water and the eluate is concentrated under reduced pressure and freeze-dried to give 84 mg of the above-mentioned compound as colorless powders.

IR(KBr)cm$^{-1}$: 1770, 1670, 1610.

NMR(D$_2$O)δ: 4.12 (3H, s), 5.32 (1H, d, J=5 Hz), 5.43 (2H, s), 5.91 (1H, d, J=5 Hz), 7.81 (1H, d, J=10 Hz), 8.23 (1H, d, J=2 Hz), 8.40 (1H, d, J=2 Hz), 8.52 (1H, d, J=10 Hz):

Elemental analysis: C$_{21}$H$_{22}$N$_{10}$O$_5$S$_3$·CF$_3$COOH·3.5-H$_2$O: Calcd.(%): C, 35.98; H, 3.94; N, 18.24. Found (%): C, 36.20; H, 3.76; N, 18.06.

EXAMPLE 2

7β-[2-(5-Amino-1,2,4-thiadiazol-3-yl)-(Z)-2-ethoxyiminoacetamido]-3-[[6-(2-aminoethylthio)imidazo[1,2-b]pyridazinium-1-yl]methyl]-3-cephem-4-carboxylate trifluoroacetic acid salt

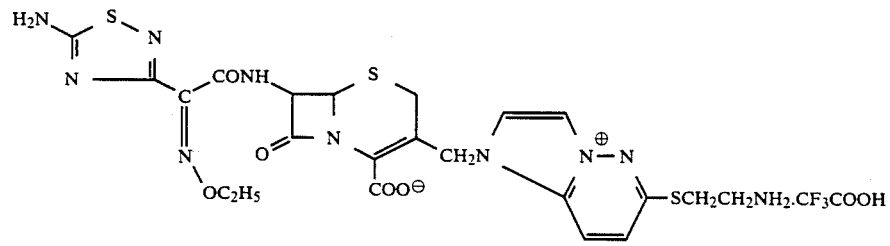

In the same manner as Example 1, the above-mentioned compound is obtained as light yellow powders.

IR(KBr)cm$^{-1}$: 1770, 1660, 1610.

NMR(D$_2$O+CD$_3$CN)δ: 1.32 (3H, t, J=7 Hz), 5.22 (1H, d, J=4.5 Hz), 5.35 (2H, ABq, J=15 Hz), 5.84 (1H, d, J=4.5 Hz), 7.75 (1H, d, J=10 Hz), 8.21 (1H, d, J=2 Hz), 8.34 (1H, d, J=2 Hz), 8.53 (1H, d, J=10 Hz)

EXAMPLE 3

7β-[2-(2-Aminothiazol-4-yl)-(Z)-2-methoxyiminoacetamido]-3-[[6-(2-aminoethylthio)imidazo[1,2-b]-pyridazinium-1-yl]methyl]-3-cephem-4-carboxylate trifluoroacetic acid salt

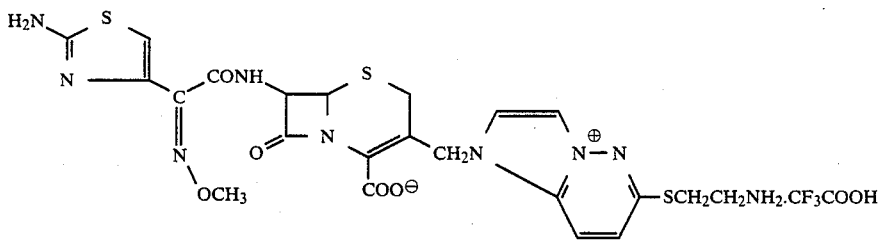

In 10 ml of dimethylformamide are dissolved 1.198 g of 7β-[2-(2-aminothiazol-4-yl)-(Z)-2-methoxyiminoacetamido]-3-hydroxymethyl-3-cephem-4-carboxylic acid tri-n-butylamine salt and 1.766 of 6-(2-tert-butoxycarbonylaminoethylthio)imidazo[1,2-b]pyridazine. After the solution is cooled to −20° C., 2.0 g of ethyl o-phenylene phosphate is added and the mixture is stirred for 1 hour, with the temperature being raised gradually to −5° C. The reaction mixture is subjected to silica gel (100 g) column chromatography and after the column is washed with acetonitrile, elution is carried out with acetonitrile-water (6:1). The eluate is concentrated under reduced pressure and the residue is subjected to XAD-II (100 ml) column chromatography. The column is successively washed with water, 10% (v/v) ethanol and 20% (v/v) ethanol in that order and elution is carried out with 30% (v/v) ethanol. The eluate is concentrated under reduced pressure and freeze-dried to give 261 mg of light yellow powders. In a mixture of 30 ml of dichloromethane and 2 ml of anisole is suspended 240 mg of the above product, and 30 ml of trifluoroacetic acid is added. The mixture is stirred at room temperature for 1 hour. The solvent is distilled off under reduced pressure and 50 ml of ether is added to the residue. The crystals are collected by filtration, washed with ether, and dissolved in 20 ml of water. The solution is adjusted to pH 3.9 with 0.1N-aqueous sodium hydroxide solution. This solution is subjected to XAD-II (120 ml) column chromatography and elution is carried out with water. The eluate is concentrated under reduced pressure and freeze-dried to give 112 mg of the above-mentioned compound as light yellow powders IR(KBr)cm$^{-1}$: 1775, 1680, 1615.

NMR(D$_2$O)δ: 4.07 (3H, s), 5.33 (1H, d, J=5 Hz), 5.45 (2H, s), 5.89 (1H, d, J=5 Hz), 7.03 (1H, s), 7.83 (1H, d, J=10 Hz), 8.25 (1H, d, J=2 Hz), 8.42 (1H, d, J=2 Hz), 8.56 (1H, d, J=10 Hz).

Elemental analysis: C$_{22}$H$_{23}$N$_9$O$_5$S$_3$·CF$_3$COOH·3.5-H$_2$O: Calcd.(%): C, 37.60; H, 4.08; N, 16.44. Found (%): C, 37.42; H, 3.69; N, 16.32.

EXAMPLE 4

7β-[2-(2-Aminothiazol-4-yl)-(Z)-2-ethoxyiminoacetamido]-3-[[6-(2-aminoethylthio)imidazo[1,2-b]-pyridazinium-1-yl]methyl]-3-cephem-4-carboxylate trifluoroacetic acid salt

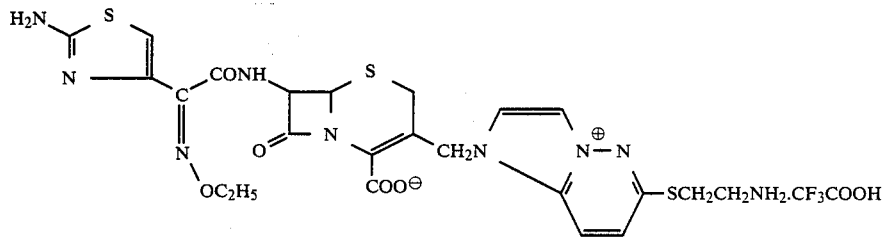

In the same manner as Example 3, the above-mentioned compound is obtained as light yellow powders.
IR(KBr)cm$^{-1}$: 1770, 1670, 1615.
NMR(D$_2$O)δ: 1.36 (3H, t, J=7 Hz), 3.49 (2H, ABq, J=18 Hz), 4.35 (2H, q, J=7 Hz), 5.32 (1H, d, J=4.5 Hz), 5.43 (2H, s), 5.88 (1H, d, J=4.5 Hz), 7.05 (1H, s), 7.81 (1H, d, J=9.5 Hz), 8.21 (1H, d, J=2 Hz), 8.40 (1H, d, J=2 Hz), 8.52 (1H, d, J=9.5 Hz).

EXAMPLE 5

7β-2-(2-Aminothiazol-4-yl)-(Z)-2-methoxyiminoacetamido]-3-[[6-(2-hydroxyethylthio)imidazo[1,2-b]-pyridazinium-1-yl]methyl]-3-cephem-4-carboxylate

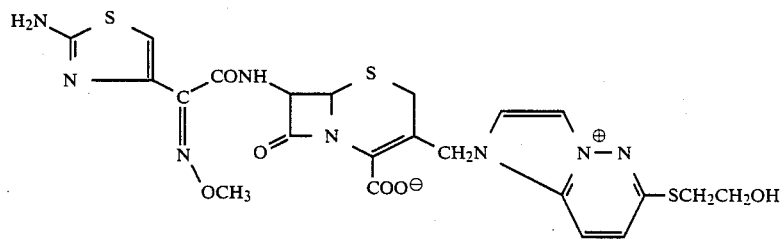

In a mixture of 35 ml of dichloromethane and 5 ml of dimethylformamide are dissolved 599 mg of 7β-[2-(2-aminothiazol-4-yl)-(Z)-2-methoxyiminoacetamido]-3-hydroxymethyl-3-cephem-4-carboxylic acid tri-n-butylamine salt and 390 mg of 6-(2-hydroxyethylthio)imidazo[1,2-b]pyridazine. After the solution is cooled to −30° C., 929 mg of 2-phenyl-2-oxo-1,3,2-benzodioxaphosphole is added and the mixture is stirred for 3 hours, with the temperature being gradually raised to 10° C. The reaction mixture is concnetrated under reduced pressure and the residue is subjected to silica gel (100 g) column chromatography, elution being carried out with acetonitrile-water (5:1). The eluate is concentrated under reduced pressure and the residue is subjected to XAD-II (100 ml) column chromatography. After the column is washed with water, elution is carried out with 10% (v/v) ethanol and the eluate is concentrated under reduced pressure and freeze-dried. The above procedure gives 39 mg of the above-mentioned compound as light yellow powders.

IR(KBr)cm$^{-1}$: 1775, 1670, 1615.

NMR(D$_2$O+CD$_3$CN)δ: 3.41 (2H, ABq, J=18 Hz), 3.52 (2H, t, J=6 Hz), 3.99 (2H, t, J=6 Hz), 4.02 (3H, s), 5.29 (1H, d, J=4.5 Hz), 5.40 (2H, s), 5.86 (1H, d, J=5 Hz), 6.98 (1H, s), 7.78 (1H, d, J=10 Hz), 8.21 (1H, d, J=2 Hz), 8.36 (1H, d, J=2 Hz), 8.51 (1H, d, J=10 Hz).

EXAMPLE 6

7β-[2-(5-Amino-1,2,4-thiadiazol-3-yl)-(Z)-2-methoxyiminoacetamido]-3-[[6-(2-aminoethylthio)imidazo[1,2-b]pyridazinium-1-yl]methyl]-3-cephem-4-carboxylate hydrochloride.

yellow powders. This product is added to 70 ml of 3N hydrochloric acid and the mixture is stirred at room temperature for 1 hour, after which it is adjusted to pH 4.0 with 3N-aqueous sodium hydroxide solution, and subjected to XAD-II(600 ml) column chromatography Elution is carried out with water. The eluate is concentrated under reduced pressure and the residue is freeze-dried to give 1.71 g of the above-mentioned compound as colorless powders.

IR(KBr)cm$^{-1}$: 1770, 1660, 1610.

NMR(D$_2$O)δ: 4.14 (3H, s), 5.32 (1H, d, J=5 Hz), 5.45 (2H, s), 5.91 (1H, d, J=5 Hz), 7.83 (1H, d, J=10 Hz), 8.25 (1H, d, J=2 Hz), 8.43 (1H, d, J=2 Hz), 8.55 (1H, d, J=10 Hz).

Elemental analysis: C$_{21}$H$_{22}$N$_{10}$O$_5$S$_3$·HCl·4H$_2$O: Calcd.(%): C, 36.07; H, 4.47; N, 20.03. Found (%): C, 35.98; J, 4.29; N, 19.95.

EXAMPLE 7

7β-[2-(2-Aminothiazol-4-yl)-(Z)-2-methoxyiminoacetamido]-3-[[5-(2-aminoethylthio)imidazo[1,2-a]-pyridinium-1-yl]methyl]-3-cephem-4-carboxylate trifluoroacetic acid salt

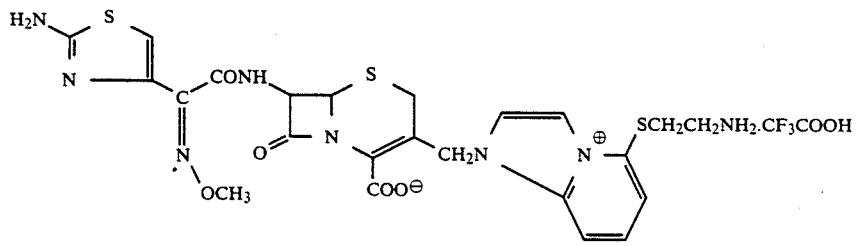

In 10 ml of dimethylformamide are dissolved 1.2 g of 7β-[2-(2-aminothiazol-4-yl)-(Z)-2-methoxyiminoacetamido]-3-hydroxymethyl-3-cephem-4-car-

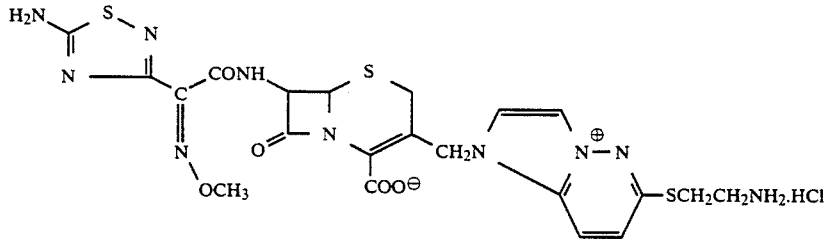

In 39 ml of dimethylformamide are dissolved 3.89 g of sodium 7β-[2-(5-amino-1,2,4-thiadiazol-3-yl)-(Z)-2-methoxyiminoacetamido]-3-hydroxymethyl-3-cephem-4-carboxylate and 7.87 g of 6-(2-tert-butoxycarbonylaminoethylthio)imidazo[1,2-b]pyridazine. After the solution is cooled to −20° C., 2.90 g of ethyl o-phenylene phosphate and 2.38 g of 2-phenyl-2-oxo-1,3,2-benzodioxaphosphole is added and the mixture is stirred for 1 hour, with the temperature being gradually raised to 0° C. The reaction mixture is subjected to silica gel (300 g) column chromatography and after the column is washed with acetonitrile, elution is carried out with acetonitrile-water (6:1). The eluate is concentrated under reduced pressure and the residue is subjected to XAD-II (400 ml) column chromatography. The column is successively washed with water, 10% (v/v) ethanol and 20% (v/v) ethanol and elution is carried out with 30% (v/v) ethanol. The eluate is concentrated under reduced pressure and freeze-dried to give 2.58 g of light boxylic acid tri-n-butylamine salt and 1.76 g of 5-(2-tert-butoxycarbonylaminoethylthio)imidazo[l,2-a]pyridine. After the solution is cooled to −20° C., 1.2 g of ethyl o-phenylene phosphate is added and the mixture is stirred for 1 hour, with the temperature being gradually increased to −3° C. The reaction mixture is then subjected to silica gel (100 g) column chromatography and after the column is washed with acetonitrile an acetonitrile-water mixtures (8:1 and 6:1) in the order mentioned, elution is carried out with acetonitrile-water (5:1). The eluate is concentrated under reduced pressure and the residue is subjected to XAD-II (100 ml) column chromatography. After the column is washed with water, 10% (v/v) ethanol and 20% (v/v) ethanol in the order mentioned, elution is carried out with 30% (v/v) ethanol. The eluate is concentrated under reduced pressure and the residue is freeze-dried to give 487 mg of light yellow powders. In a mixture of 40 ml of dichloromethane and 2 ml of anisole is suspended 451 mg of the above powders, followed by addition of 40 ml of trifluoroacetic acid and stirring at room temperature for 1 hour. The solvent is then distilled off under reduced pressure and 100 ml of ether is added to the residue. The crystals that separate out are collected by filtration, washed with ether and dissolved in 30 ml of water. This aqueous solution is adjusted to pH 3.8 with 0.1N-aqueous sodium hydroxide solution. The solution is then subjected to XAD-II (100 ml) column chromatography and elution is carried out with water. The eluate is concentrated under reduced pressure and the residue is freeze-dried to give 249 mg of the title compound as colorless powders.

IR(KBr)cm$^{-1}$: 1770, 1675, 1630.

NMR(D$_2$O)δ: 3.13–3.80 (6H, m), 4.05 (3H, s), 5.29 (1H, d, J=5 Hz), 5.43 (2H, s), 5.86 (1H, d, J=5 Hz), 6.99 (1H, s), 7.70–8.49 (5H, m).

EXAMPLE 8

7β-[2-(2-Aminothiazol-4-yl)-(Z)-2-ethoxyiminoacetamido]-3-[[5-(2-aminoethylthio)imidazo[1,2-a]-pyridinium-1-yl]methyl]-3-cephem-4-carboxylate hydrochloride

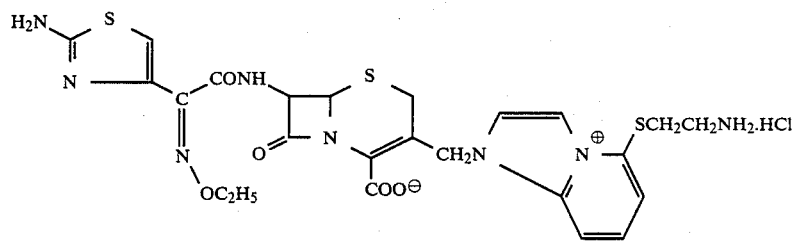

In 10 ml of dimethylformamide are dissolved 613 mg of 7β-[2-(2-aminothiazol-4-yl)-(Z)-2-ethoxyiminoacetamido]-3-hydroxymethyl-3-cephem-4-carboxylic acid tri-n-butylamine salt and 880 mg of 5-(2-tertbutoxycarbonylaminoethylthio)imidazo[1,2-a]pyridine. After the solution is cooled to −20° C., 697 mg of 2-phenyl-2-oxo-1,3,2-benzodioxaphosphole is added and the mixture is stirred for 1 hour, with the temperature being gradually increased to −5° C. The reaction mixture is subjected to silica gel (80 g) column chromatography and after the column is washed with acetonitrile and acetonitrile-water (8:1) in the order mentioned, elution is carried out with acetonitrile-water mixtures (6:1 and 5:1). The eluate is concentrated under reduced pressure and the residue is subjected to XAD-II (60 ml) column chromatography. After the column is successively washed with water, 10% (v/v) ethanol and 20% (v/v) ethanol, elution is carried out with 30% (v/v) ethanol. The eluate is concentrated under reduced pressure and the residue is freeze-dried to give 165 mg of light yellow powders. This product is added to 10 ml of 3N-hydrochloric acid and the mixture is stirred at room temperature for 30 minutes, after which it is adjusted to pH 3.7 with 1N-aqueous sodium hydroxide. The solution is then subjected to XAD-II (100 ml) column chromatography and elution is carried out with water. The eluate is concentrated under reduced pressure and the residue is freeze-dried to give 30 mg of the title compound as colorless powders.

IR(KBr)cm$^{-1}$: 1770, 1660, 1630.

NMR(D$_2$O)δ: 1.37 (3H, t, J=7 Hz), 3.17–3.83 (6H, m), 4.39 (2H, q, J=7 Hz), 5.32 (1H, d, J=5 Hz), 5.46 (2H, ABq, J=15 Hz), 5.91 (1H, d, J=5 Hz), 7.16 (1H, s), 7.73–7.90 (1H, m), 8.07–8.20 (2H, m), 8.24 (1H, d, J=2 Hz), 8.48 (1H, d, J=2 Hz).

EXAMPLE 9

7β-[2-(5-Amino-1,2,4-thiadiazol-3-yl)-(Z)-2methoxyiminoacetamido]-3-[[5-(2-aminoethylthio)imidazo[1,2-a]pyridinium-1-yl]methyl]-3-cephem-4carboxylate hydrochloride.

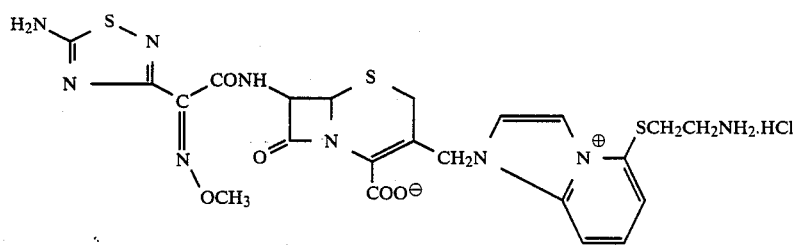

In 10 ml of dimethylformamide and dissolved 437 mg of sodium 7β-[2-(5-amino-1,2,4-thiadiazol-3-yl)-(Z)-2methoxyiminoacetamido]-3-hydroxymethyl-3-cephem-4carboxylate and 880 mg of 5-(2-tert-butoxycarbonylaminoethylthio)imidazo[1,2-a]pyridine. After the solution is cooled to −20° C., 600 mg of ethyl o-phenylene phosphate is added and the mixture is stirred for 1 hour, with the temperature being gradually increased to −3° C. The reaction mixture is subjected to silica gel (80 g) column chromatography and after the column is washed with acetonitrile and acetonitrile-water (8:1) in the order mentioned, elution is carried out with acetonitrile-water (6:1). The eluate is concentrated under reduced pressure and the residue is freeze-dried to give 296 mg of light yellow powders This product is added to 10 ml of 3N-hydrochloric acid and the mixture is stirred at room temperature for 1 hour. The solution is then adjusted to pH 3.8 with 1N-aqueous sodium hydroxide solution. This solution is subjected to XAD-II (100 ml) column chromatography and elution is carried out with water. The eluate is concentrated under reduced pressure and the residue is freeze-dried to give 86 mg of the title compound as colorless powders.

IR(KBr)cm$^{-1}$: 1765, 1660, 1625.

NMR(D₂O)δ: 3.15–3.80 (6H, m), 4.13 (3H, s), 5.31 (1H, d, J=5 Hz), 5.45 (2H, s), 5.91 (1H, d, J=5 Hz), 7.72–8.50 (5H, m).

Elemental analysis: C₂₂H₂₄N₁₀O₅S₂.HCl.4H₂O. Calcd. (%): C, 38.79; H, 4.88; N, 20.56. Found (%): C, 38.75; H, 4.71; N, 20.60.

EXAMPLE 10

7β-[2-(Aminothiazol-4-yl)-(Z)-2-methoxyiminoacetamido]-3-[[6-(2-aminoethylamino)imidazo[1,2-b]pyridazinium-1-yl]methyl]-3-cephem-4-carboxylate hydrochloride

EXAMPLE 11

7β-[2-(2-Aminothiazol-4-yl)-(Z)-2-ethoxyiminoacetamido]-3-[[6-(2-aminoethylamino)imidazo[1,2-b]pyridazinium-1-yl]methyl]-3-cephem-4-carboxylate hydrochloride

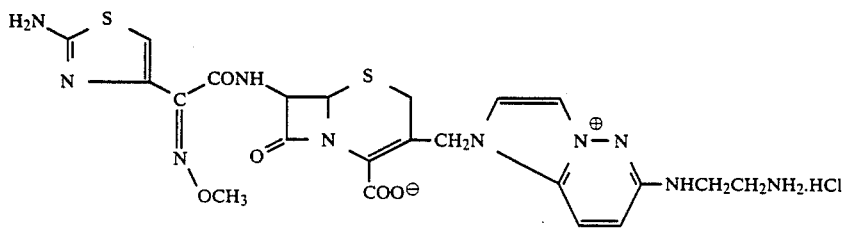

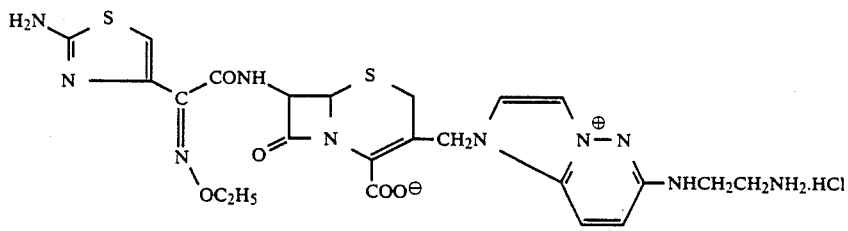

In 15 ml of dimethylformamide are dissolved 898 mg of 7β-[2-(2-aminothiazol-4-yl)-(Z)-2-methoxyiminoacetamido-]3-hydroxymethyl-3-cephem-4-carboxylic acid tri-n-butylamine salt and 1.248 g of 6-(2-tert-butoxycarbonylaminoethylamino)imidazo[1,2-b]pyridazine. After the solution is cooled to −20° C., 1.045 g of 2-phenyl-2-oxo-1,3,2-benzodioxaphosphole is added and the mixture is stirred for 1 hour, with the temperature being gradually raised to −3° C. The reaction mixture is subjected to silica gel (80 g) column chromatography and after the column is washed with acetonitrile and acetonitrile-water (8:1) in the order mentioned, elution is carried out with acetonitrile-water (5:1). The eluate is concentrated under reduced pressure and the residue is chromatographed on a Diaion HP 20 (70 ml) column. The column is washed with water, 10% (v/v) ethanol and 20% (v/v) ethanol in the order mentioned and elution is carried out with 30% (v/v) ethanol. The eluate is concentrated under reduced pressure and the residue is freeze-dried to give 403 mg of light yellow powders. This product is added to 10 ml of 3N-hydrochloric acid and the mixture is stirred at room temperature for 30 minutes. Then, under ice-cooling, the solution is adjusted to pH 3.8 with 1N-aqueous sodium hydroxide solution. This solution is subjected to XAD-II (100 ml) column chromatography and elution is carried out with water. The eluate is concentrated under reduced pressure and the residue is freeze-dried to give 223 mg of the title compound as colorless powders.

IR(KBr)cm⁻¹: 1770, 1660.

NMR(D₂O)δ: 3.15–3.95 (6H, m), 4.09 (3H, s), 4.33 (1H, d, J=4.5 Hz), 5.36 (2H, s), 5.87 (1H, d, J=4.5 Hz), 7.04 (1H, s), 7.36 (1H, d, J=9.5 Hz), 8.02 (1H, d, J=2 Hz), 8.10 (1H, d, J=2Hz), 8.28 (1H, d, J=9.5 Hz).

In 10 ml of dimethylformamide are dissolved 613 mg of 7β-[2-(2-aminothiazol-4-yl)-(Z)-2-ethoxyiminoacetamido]-3-hydroxymethyl-3-cephem-4-carboxylic acid tri-n-butylamine salt and 832 mg of 6-(2-tert-butoxycarbonylaminoethylamino)imidazo[1,2-b]pyridazine. After the solution is cooled to −20° C., 600 mg of ethyl o-phenylene phosphate is added and the mixture is stirred for 1.5 hours, with the temperature being gradually raised to 5° C. The reaction mixture is subjected to silica gel (80 g) column chromatography and after the column is washed with acetonitrile and acetonitrile-water (8:1) in the order mentioned, elution is carried out with acetonitrile-water (6:1). The eluate is concentrated under reduced pressure and the residue is freeze-dried to give 325 mg of light yellow powders. This product is added to 10 ml of 3N-hydrochloric acid and the mixture is stirred at room temperature for 1 hour. Under icecooling, the solution is adjusted to pH 3.4 with 3Naqueous sodium hydroxide solution. This solution is subjected to XAD-II (100 ml) column chromatography and elution is carried out with water. The eluate is concentrated under reduced pressure and the residue is freeze-dried to give 112 mg of the title compound as colorless powders.

IR(KBr)cm⁻¹: 1775, 1660.

NMR(D₂O)δ: 1.37 (3H, t, J=7 Hz), 3.18–3.93 (6H, m), 4.36 (2H, q, J=7 Hz), 5.33 (1H, d, J=5 Hz), 5.35 (2H, s), 5.90 (1H, d, J=5 Hz), 7.10 (1H, s), 7.36 (1H, d, J=10 Hz), 8.00 (1H, d, J=2 Hz), 8.09 (1H, d, J=2 Hz), 8.26 (1H, d, J=10 Hz).

Elemental analysis: C₂₃H₂₆N₁₀O₅S₂.HCl.5½H₂O: Calcd. (%): C, 38.25; H, 5.30; N, 19.39. Found (%): C, 38.38; H, 4.91; N, 19.29.

EXAMPLE 12

7β-[2-(5-Amino-1,2,4-thiadiazol-3-yl)-(Z)-2-methoxyiminoacetamido]-3-[[6-(2-aminoethylamino)imidazo[1,2-b]pyridazinium-1-yl]methyl]-3-cephem-4-carboxylate hydrochloride

[1,2-a]pyridinium-1-yl]methyl]-3-cephem-4-carboxylate hydrochloride

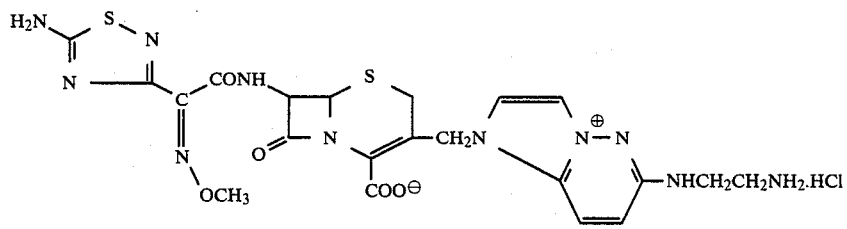

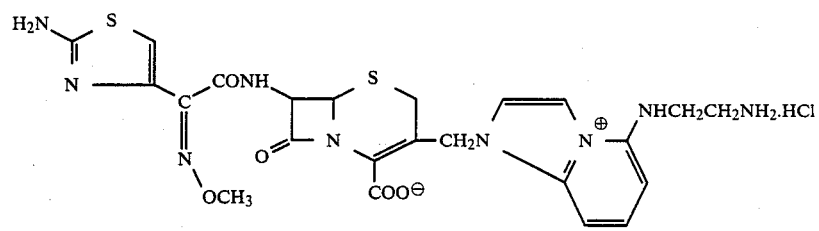

In 10 ml of dimethylformamide are dissolved 436 mg of sodium 7β-[2-(5-amino-1,2,4-thiadiazol-3-yl)-(Z)-2-methoxyiminoacetamido]-3-hydroxymethyl-3-cephem-4-carboxylate and 832 mg of 6-(2-tert-butoxycarbonyl-aminoethylamino)imidazo[1,2-b]pyridazine. After the solution is cooled to −15° C., 600 mg of ethyl o-phenylene phosphate is added and the mixture is stirred for 1 hour, with the temperature being gradually increased to 0° C. The reaction mixture is subjected to silica gel (80 g) column chromatography and after the column is washed with acetonitrile and acetonitrile-water (8:1) in the order mentioned, elution is carried out with acetonitrile-water (5:1). The eluate is concentrated under reduced pressure and the residue is freeze-dried to give 380 mg of light yellow powders. This product is added to 10 ml of 3N-hydrochloric acid and the mixture is stirred at room temperature for 1 hour, after which it is adjusted to pH 3.0 with 3N-aqueous sodium hydroxide solution. This solution is subjected to XAD-II (100 ml) column chromatography and elution is carried out with water. The eluate is concentrated and the residue is freeze-dried to give 143 mg of the title compound as colorless powders.

IR(KBr)cm$^{-1}$: 1770, 1660, 1600.

NMR(D$_2$O)δ: 3.17–3.93 (6H, m), 4.13 (3H, s), 5.30 (1H, d, J=5 Hz), 5.33 (2H, s), 5.91 (1H, d, J=5 Hz), 7.33 (1H, d, J=10 Hz), 7.98 (1H, d, J=2 Hz), 8.06 (1H, d, J=2 Hz), 8.23 (1H, d, J=10 Hz).

Elemental analysis: C$_{21}$H$_{23}$N$_{11}$O$_5$S$_2$.HCl.5H$_2$O. Calcd. (%): C, 36.03; H, 4.89; N, 22.01. Found (%): C, 35.89; H, 4.68; N, 21.81.

EXAMPLE 13

7β-[2-(2-Aminothiazol-4-yl)-(Z)-2-methoxyiminoacetamido]-3-[[5-(2-aminoethylamino)imidazo- In 10 ml of dimethylformamide are dissolved 599 mg of 7β-[2-(2-aminothiazol-4-yl)-(Z)-2-methoxyiminoacetamido]-3-hydroxymethyl-3-cephem-4-carboxylic acid tri-n-butylamine salt and 691 mg of 5-(2-tert-butoxycarbonyl-aminoethylamino)imidazo[1,2-a]pyridine. After the solution is cooled to −20° C., 600 mg of ethyl o-phenylene phosphate is added and the mixture is stirred for 1 hour, with the temperature being gradually increased to 0° C. The reaction mixture is subjected to silica gel (80 g) column chromatography and after the column is washed with acetonitrile and acetonitrile-water (8:1), elution is carried out with acetonitrile-water (6:1). The eluate is concentrated under reduced pressure and the residue is freeze-dried to give 263 mg of light yellow powders. This product is added to 10 ml of 3N-hydrochloric acid and the mixture is stirred at room temperature for 1 hour. It is then diluted with 20 ml of water and adjusted to pH 3.8 with 3N-aqueous sodium hydroxide solution under ice-cooling. The solution is then subjected to XAD-II (100 ml) column chromatography and elution is carried out with water. The eluate is concentrated under reduced pressure and the residue is freeze-dried to give 75 mg of the title compound as colorless powders.

IR(KBr)cm$^{-1}$: 1770, 1640.

NMR(D$_2$O)δ: 3.16–4.03 (6H, m), 4.07 (3H, s), 5.27 (1H, d, J=5 Hz), 5.30 (2H, ABq, J=15 Hz), 5.86 (1H, d, J=5 Hz), 6.71 (1H, d, J=8 Hz), 7.06 (1H, s), 7.36 (1H, d, J=9 Hz), 7.88–8.13 (3H, m).

EXAMPLE 14

7β-[2-(2-Aminothiazol-4-yl)-(Z)-2-ethoxyiminoacetamido]-3-[[5-(2-aminoethylamino)imidazo-[1,2-a]pyridinium-1-yl]methyl]-3-cephem-4-carboxylate hydrochloride

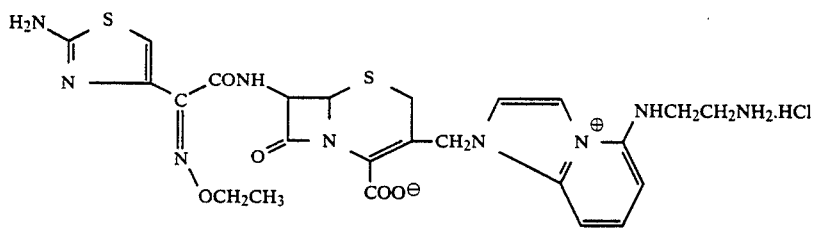

In 10 ml of dimethylformamide are dissolved 613 mg of 7β-[2-(2-aminothiazol-4-yl)-(Z)-2-ethoxyiminoacetamido]-3-hydroxymethyl-3-cephem-4-carboxylic acid tri-n-butylamine salt and 892 mg of 5-(2-tert-butoxycarbonylaminoethylamino)imidazo[1,2-a]pyridine. After the solution is cooled to −20° C., 600 mg of ethyl o-phenylene phosphate is added and the mixture is stirred for 1 hour, with the temperature being gradually increased to 0° C. Thereafter, the reaction mixture is worked up in the same manner as Example 13 to give 69 mg of the title compound as colorless powders.

IR(KBr)cm$^{-1}$: 1770, 1640.

NMR(D$_2$O)δ: 1.37 (3H, t, J=7 Hz), 3.16–4.03 (6H, m), 4.38 (2H, q, J=7 Hz), 5.29 (1H, d, J=5 Hz), 5.32 (2H, ABq, J=15 Hz), 5.89 (1H, d, J=5 Hz), 6.74 (1H, d, J=8 Hz), 7.13 (1H, s), 7.37 (1H, d, J=9 Hz), 7.90–8.17 (3H, m).

EXAMPLE 15

7β-[2-(5-Amino-1,2,4-thiadiazol-3-yl)-(Z)-2-methoxyiminoacetamido]-3-[[5-(2-aminoethylamino)imidazo[1,2-a]pyridinium-1-yl]methyl]-3-cephem-4-carboxylate hydrochloride

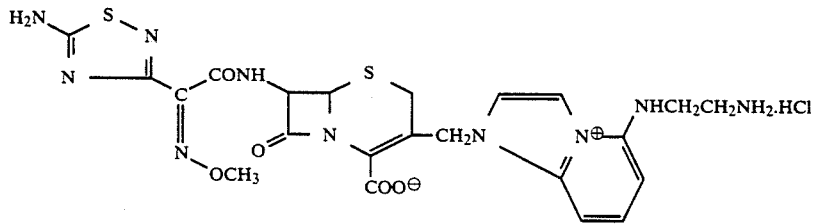

In 10 ml of dimethylformamide are dissolved 436 mg of sodium 7β-[2-(5-amino-1,2,4-thiadiazol-3-yl)-(Z)-2-methoxyiminoacetamido]-3-hydroxymethyl-3-cephem-4-carboxylic acid and 829 mg of 5-(2-tert-butoxycarbonylaminoethyl-amino)imidazo[1,2-a]pyridine. After the solution is cooled to −20° C., 600 mg of ethyl o-phenylene phosphate is added and the mixture is stirred for 1 hour, with the temperature being gradually increased to 0° C. Thereafter, the reaction mixture is worked up in the same manner as Example 13 to give 102 mg of the title compound as colorless powders.

IR(KBr)cm$^{-1}$: 1770, 1645.

NMR(D$_2$O+CD$_3$CN)δ: 3.05–4.00 (6H, m), 4.10 (3H, s), 5.25 (1H, d, J=5 Hz), 5.31 (2H, s), 5.88 (1H, d, J=5 Hz), 6.72 (1H, d, J=8 Hz), 7.42 (1H, d, J=9 Hz), 7.89–8.15 (3H, m).

EXAMPLE 16

7β-[2-(2-Aminothiazol-4-yl)-(Z)-2-ethoxyiminoacetamido]-3-[[6-(2-aminoethylthio)imidazo[1,2-b]-pyridazinium-1-yl]methyl]-3-cephem-4-carboxylate hydrochloride

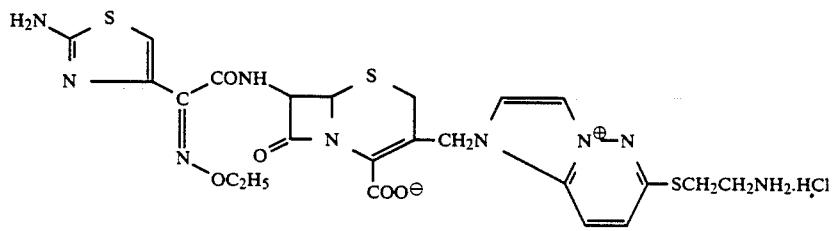

In 67 ml of dimethylformamide are dissolved 8.22 g of 7β-[2-(2-aminothiazol-4-yl)-(Z)-2-ethoxyiminoacetamido]-3-hydroxymethyl-3-cephem-4-carboxylic acid tri-n-butylamine salt and 11.84 g of 6-(2-tert-butoxycarbonylaminoethylthio)imidazo[1,2-b]pyridazine and after the solution is cooled to −20° C., 8.05 g of ethyl o-phenylene phosphate is added and the mixture is stirred for 1.5 hours with the temperature being gradually raised to 0° C. The reaction mixture is subjected to silica gel (700 g) column chromatography and after the column is washed with acetonitrile, elution is carried out with acetonitrile-water (8:1, 6:1 and 5:1). The fractions rich in the desired product are pooled and concentrated under reduced pressure and the residue is freeze-dried to give 2.63 g of a light yellow powders. This product is added to 70 ml of 3 N-hydrochloric acid and the mixture is stirred at room temperature for 1 hour. Then, with ice-cooling, the mixture is adjusted to pH 3.8 with 3 N-aqueous sodium hydroxide solution. The mixture is subjected to XAD-II (600 ml) column chromatography and elution is carried out with water. The eluate is concentrated and freeze-dried to give 1.26 g of the title compound as light yellow powders.

IR (KBr) cm$^{-1}$: 1765, 1660, 1610.

NMR (D₂O) δ: 1.36 (3H, t, J=7 Hz), 3.15–4.0 (6H, m), 4.34 (2H, q, J=7 Hz), 5.34 (1H, d, J=5 Hz), 5.45 (2H, s), 5.89 (1H, d, J=5 Hz), 7.03 (1H, s), 7.84 (1H, d, J=9.5 Hz), 8.25 (1H, d, J=2 Hz), 8.43 (1H, d, J=2 Hz), 8.55 (1H, d, J=9.5 Hz).

Elemental analysis: $C_{23}H_{25}N_9O_5S_3 \cdot HCl \cdot 4.5H_2O$. Calcd. (%): C, 38.30; H, 4.89; N, 17.48. Found (%): C, 38.25; H, 4.68; N, 17.46.

EXAMPLE 17

7β-[2-(2-Aminothiazol-4-yl)-(Z)-2-[2-(2-methoxyethoxy)ethoxyimino]acetamido]-3-[[6-(2-aminoethylthio)imidazo[1,2-b]pyridazinium-1-yl]methyl]-3-cephem-4-carboxylate hydrochloride

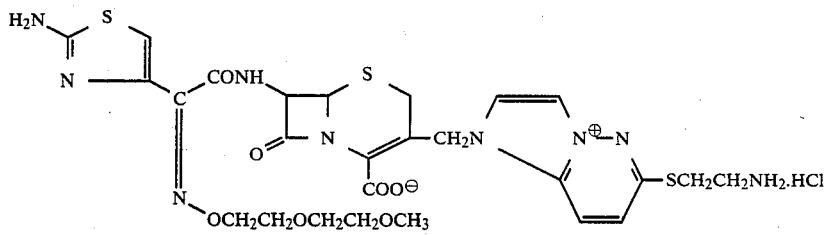

In 12 ml of dichloromethane are dissolved 475 mg of 2-(2-tritylaminothiazol-4-yl)-(Z)-2-[2-(2-methoxyethoxy)ethoxyimino]acetic acid and 0.125 ml of triethylamine, and with ice-cooling and stirring, 195 mg of phosphorus pentachloride is added. The mixture is stirred at 0° C. for 10 minutes and then at room temperature for 30 minutes. The reaction mixture is concentrated under reduced pressure and the solid residue is washed with hexane and dissolved in 10 ml of dry tetrahydrofuran. The insolubles are filtered off from the solution. On the other hand, 300 mg of 7β-amino-3-[[6-[2-(2-methylsulfonylethoxycarbonylamino)ethylthio]-imidazo[1,2-b]pyridazinium-1-yl]methyl]-3-cephem-4-carboxylate and 189 mg of sodium hydrogen carbonate are dissolved in a mixture of 25 ml of water and 15 ml of tetrahydrofuran and with ice-cooling and stirring, the tetrahydrofuran solution of the acid chloride prepared as above is added dropwise. The reaction mixture is stirred under ice-cooling for 1 hour and, then, concentrated under reduced pressure. The residual aqueous solution is diluted with 75 ml of methanol, followed by addition of 4 ml of 3 N-hydrochloric acid. The mixture is stirred at room temperature for 2 hours. The methanol is then distilled off under reduced pressure, the residual aqueous solution is filtered, and the filtrate is adjusted to pH 5. The solution is subjected to XAD-II (200 ml) column chromatography and after the column is washed with water, elution is carried out with 20% ethanol. The eluate is concentrated under reduced pressure and freeze-dried to give 306 mg of colorless powders. In 25 ml of water is dissolved 275 mg of the above product and with ice-cooling and stirring, the solution is adjusted to pH 12.5 with 1 N-aqueous sodium hydroxide solution. At pH 12.3 to 12.5, the mixture is stirred under ice-cooling for 40 minutes, after which it is adjusted to pH 3.9 with 1 N-hydrochloric acid and concentrated under reduced pressure. The residue is subjected to XAD-II (200 ml) column chromatography and after the column is washed with water, elution is carried out with 20% (v/v) ethanol, 30% (v/v) ethanol, 40% (v/v) ethanol, and water-acetonitrile (3:2). The fractions rich in the desired compound are pooled and concentrated under reduced pressure and the residual aqueous solution is adjusted to pH 4.0. This solution is chromatographed on a Sephadex LH-20 (400 ml) column and elution is carried out with water. The eluate is concentrated under reduced pressure and freeze-dried to give 77 mg of the title compound as light yellow powders.

IR (KBr) cm⁻¹: 2930, 1770, 1660, 1610.

NMR (D₂O) δ: 3.49 (3H, s), 3.6–4.1 (12H, m), 4.4–4.6 (2H, m), 5.39 (1H, d, J=5 Hz), 5.53 (2H, br.s), 5.99 (1H, d, J=5 Hz), 7.13 (1H, s), 7.88 (1H, d, J=10 Hz), 8.33 (1H, br.s), 8.52 (1H, br.s), 8.65 (1H, d, J=10 Hz).

EXAMPLE 18

7β-[2-(2-Aminothiazol-4-yl)-(Z)-2-(3-aminopropoxyimino)acetamido]-3-[[6-(2-aminoethylthio)imidazo[1,2-b]pyridazinium-1-yl]methyl]-3-cephem-4-carboxylate trihydrochloride

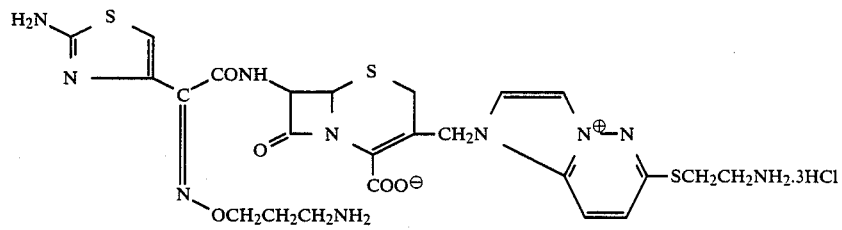

In 15 ml of dichloromethane are dissolved 505 mg of 2-(2-chloroacetamidothiazol-4-yl)-(Z)-2-(3-tert-butoxycarbonylaminopropoxyimino)acetic acid and 0.168 ml of triethylamine and with ice-cooling and stirring, 262 mg of phosphorus pentachloride is added. The mixture is stirred at 0° C. for 5 minutes and, then, at room temperature for 30 minutes. The solvent is distilled off under reduced pressure and the solid residue is washed with hexane. This solid is dissolved in 10 ml of dry tetrahydrofuran and the insolubles are filtered off. The filtrate is used as the acid chloride solution.

On the other hand, 304 mg of 7β-amino-3-[[6-(2-tert-butoxycarbonylaminoethylthio)imidazo[1,2-b]-pyridazinium-1-yl]methyl]-3-cephem-4-carboxylate and 252 mg of sodium hydrogen carbonate are dissolved in a mixture of 20 ml of water and 10 ml of tetrahydrofuran and with ice-cooling and stirring, the acid chloride solution prepared above is added dropwise to the solution. The mixture is stirred under ice-cooling for 15 minutes and, then, adjusted to pH 6.5, followed by addition of 310 mg of sodium N-methyldithiocarbamate. The mixture is stirred at room temperature for 30 minutes and after a further addition of 310 mg of sodium N-methyldithiocarbamate, further stirred for one hour. The reaction mixture is adjusted to pH 5.0 and concentrated under reduced pressure. The residue is subjected to silica gel (100 g) column chromatography and elution is carried out with acetonitrile-water (7:1 and 5:1). The fractions rich in the desired compound are pooled and concentrated under reduced pressure to about 50 ml. The residue is diluted with 20 ml of methanol and 2 ml of 12 N-hydrochloric acid and stirred at room temperature for 3 hours and at 0° to 5° C. for 70 hours. The methanol is distilled off under reduced pressure and the residual aqueous solution is adjusted to pH 2.5 and subjected to XAD-II (200 ml) column chromatography. After the column is washed with water and 5% (v/v) ethanol, elution is carried out with 30% (v/v) ethanol. The eluate is concentrated under reduced pressure and freeze-dried to give 103 mg of the title compound as light yellow powders.

IR (KBr) cm$^{31}$ $^1$: 2980, 1770, 1660, 1615, 1525.

NMR (D$_2$O) δ: 2.1–2.5 (2H, m), 3.2–4.0 (8H, m), 4.54 (2H, t, J=6 Hz), 5.45 (1H, d, J=5 Hz), 5.53 (2H, br.s), 6.03 (1H, d, J=5 Hz), 7.23 (1H, s), 7.94 (1H, d, J=10 Hz), 8.32 (1H, d, J=2 Hz), 8.53 (1H, d, J=2 Hz), 8.61 (1H, d, J=10 Hz).

EXAMPLE 19

7β-[2-(2-Aminothiazol-4-yl)-(Z)-2-(2-cyanomethylthioethoxyimino)acetamido]-3-[[6-(2-aminoethylthio)imidazo[1,2-b]pyridazinium-1-yl]methyl]-3-cephem-4-carboxylate dihydrochloride In the same manner as Example 17, 2-(2-tritylaminothiazol-4-yl)-(Z)-2-(2-cyanomethylthioethoxyimino)acetic acid is converted to the corresponding acid chloride and then reacted with 7β-amino-3-[[6-[2-(2-methylsulfonylethoxycarbonylamino)ethylthio]imidazo[1,2-b]pyridazinium-1-yl]methyl]-3-cephem-4-carboxylate, followed by elimination of protective groups to give the title compound as colorless powders.

IR (KBr) cm$^{-1}$: 3400, 3100, 2240, 1770, 1670, 1620.

NMR (D$_2$O) δ: 3.1–4.0 (10H, m), 5.43 (1H, d, J=5 Hz), 5.54 (2H, br.s), 5.98 (1H, d, J=5 Hz), 7.27 (1H, s), 7.93 (1H, d, J=10 Hz), 8.33 (1H, d, J=2 Hz), 8.52 (1H, d, J=2 Hz), 8.63 (1H, d, J=10 Hz).

EXAMPLE 20

7β-[2-(2-Aminothiazol-4-yl)-(Z)-2-(4-aminobutoxyimino)acetamido]-3-[[6-(2-aminoethylthio)imidazo[1,2-b]pyridazinium-1-yl]methyl]-3-cephem-4-carboxylate trifluoroacetic acid salt In 10 ml of dichloromethane are dissolved 601 mg of 2-(2-tritylaminothiazol-4-yl)-(Z)-2-(4-tert-butoxycarbonylaminobutoxyimino)acetic acid and 0.14 ml of triethylamine, and with ice-cooling and stirring, 219 mg of phosphorus pentachloride is added. The mixture is stirred under ice-cooling for 5 minutes and, then, at room temperature for 30 minutes. The reaction mixture is concentrated under reduced pressure and the residue is washed with hexane and dissolved in tetrahydrofuran. The solution is filtered and the filtrate is used as the acid chloride solution. On the other hand, 303 mg of 7β-amino-3-[[6-(2-tert-butoxycarbonylaminoethylthio)imidazo[1,2-b]pyridazinium-1-yl]methyl]- 3-cephem-4-carboxylate and 300 mg of sodium hydrogen carbonate are dissolved in a mixture of 10 ml of water and 10 ml of tetrahydrofuran and with ice-cooling and stirring, the above acid chloride solution is added dropwise. The mixture is stirred under ice-cooling for 1 hour, after which the tetrahydrofuran is distilled off under reduced pressure and 70 ml of acetonitrile is added to the residue. The mixture is subjected to silica gel (80 g) column chromatography and elution is carried out with acetonitrile-water (7:1 and 6:1). The eluate is concentrated under reduced pressure and freeze-dried. The resulting powders are suspended in 30 ml of dichloromethane and with ice-cooling and stirring, 3 ml of anisole and 30 ml of trifluoroacetic acid are added. The mixture is stirred under ice-cooling for 1 hour and, then, concentrated under reduced pressure. To the residue are added 100 ml of ether and 100 ml of petroleum ether and the resulting powder is collected by filtration and dissolved in water. The solution is subjected to XAD-II (200 ml) column chromatography and after the column is washed with water, elution is carried out with 5% (v/v)

ethanol. The eluate is concentrated under reduced pressure and freeze-dried to give 225 mg of the title compound as colorless powders.

IR (KBr) cm$^{-1}$: 1770, 1680, 1620, 1530.

NMR (D$_2$O) δ: 1.8–2.1 (4H, m), 3.1–3.95 (8H, m), 4.35 (2H, m), 5.43 (1H, d, J=5 Hz), 5.55 (2H, br.s), 6.03 (1H, d, J=5 Hz), 7.18 (1H, s), 7.93 (1H, d, J=10 Hz), 8.38 (1H, d, J=2 Hz), 8.53 (1H, d, J=2 Hz), 8.62 (1H, d, J=10 Hz).

EXAMPLE 21

7β-[2-(2-Aminothiazol-4-yl)-(Z)-2-allyloxyiminoacetamido]-3-[[6-(2-aminoethylthio)imidazo[1,2-b]pyridazinium-1-yl]methyl]-3-cephem-4-carboxylate hydrochloride

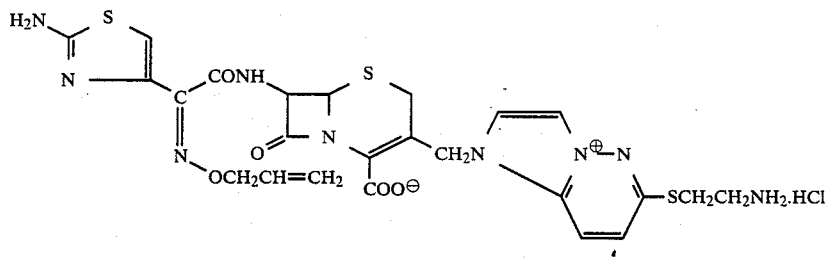

In the same manner as Example 16, the title compound is obtained as colorless powders.

IR (KBr) cm$^{-1}$: 3100, 1770, 1670, 1620, 1520.

NMR (D$_2$O+DCl) δ: 3.25–3.8 (6H,m), 5.2–5.8 (5H, m), 5.94 (1H, d, J=5 Hz), 5.95–6.3 (1H, m), 7.22 (1H, s,), 7.8–8.55 (4H, m).

EXAMPLE 22

7β-[2-(5-Amino-1,2,4-thiadiazol-3-yl)-(Z)-2-methoxyiminoacetamido]-3-[[6-[2-(N-formimidoylamino)ethylthio]imidazo[1,2-b]pyridazinium-1-yl]methyl]-3-cephem-4-carboxylate hydrochloride

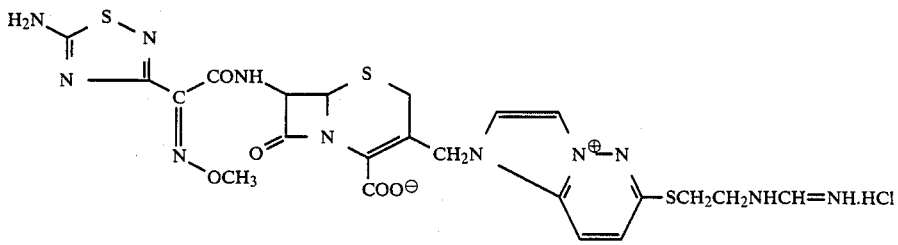

In 20 ml of water is dissolved 200 mg of 7β-[2-(5-amino-1,2,4-thiadiazol-3-yl)-(Z)-2-methoxyiminoacetamido]-3-[[6-(2-aminoethylthio)imidazo[1,2-b]pyridazinium-1-yl]methyl]-3-cephem-4-carboxylate hydrochloride of Example 6 and with ice-cooling, the solution is adjusted to pH 8.5 with 0.1 N-aqueous sodium hydroxide solution. Then, at this pH 8.5, 344 mg of O-benzyl formimidate hydrochloride is added in small portions and the mixture is stirred under ice-cooling for 1 hour. The reaction mixture is adjusted to pH 3.0 with 0.1 N-hydrochloric acid and washed with 50 ml of ethyl acetate. The water layer is concentrated to about 15 ml. The concentrate is subjected to XAD-II (100 ml) column chromatography and elution is carried out with water. The eluate is concentrated under reduced pressure and the residue is freeze-dried to give 73 mg of the title compound as colorless powders.

IR (KBr) cm$^{-1}$: 1775, 1710, 1665, 1615, 1560.

NMR (D$_2$O) δ: 3.15–4.05 (6H, m), 4.15 (3H, s , 5.35 (1H, d, J=5 Hz), 5.50 (2H, s), 5.93 (1H, d, J=5 Hz), 7.83 (1H, d, J=10 Hz), 7.98 (1H, s), 8.22–8.45 (2H, m), 8.52 (1H, d, J=10 Hz).

EXAMPLE 23

7β-[2-(5-Amino-1,2,4-thiadiazol-3-yl)-(Z)-2-methoxyiminoacetamido]-3-[[6-[2-(N-acetimidoylamino)ethylthio]imidazo[1,2-b]pyridazinium-1-yl]methyl]-3-cephem-4-carboxylate hydrochloride

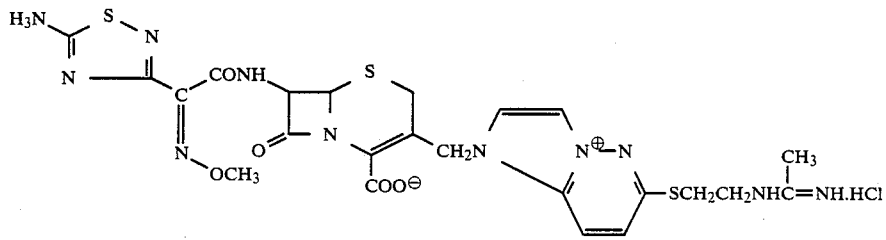

In the same manner as Example 22, 7β-[2-(5-amino-1,2,4-thiadiazol-3-yl)-(Z)-2-methoxyiminoacetamido]-3-[[6-(2-aminoethylthio)imidazo[1,2-b]pyridazinium-1-yl]methyl]-3-cephem-4-carboxylate hydrochloride is reacted with O-benzyl acetimidate hydrochloride at pH 8.5 and the reaction product is purified by XAD-II column chromatography to give the title compound as colorless powders.

IR (KBr) cm$^{-1}$: 1775, 1675, 1630, 1560.

NMR (D$_2$O) δ: 2.33, 2.42 (3H in all), 3.15–4.0 (6H, m), 4.13 (3H, s), 5.35 (1H, d, J=5 Hz), 5.50 (2H, s), 5.93

(1H, d, J=5 Hz), 7.83 (1H, d, J=10 Hz), 8.26 (1H, d, J=2 Hz), 8.41 (1H, d, J=2 Hz), 8.53 (1H, d, J=10 Hz).

Elemental analysis: $C_{23}H_{25}N_{11}O_5S_3 \cdot HCl \cdot 4.5H_2O$. Calcd. (%): C, 36.87; H, 4.71; N, 20.56. Found (%): C, 36.96; H, 4.57; N, 20.62.

EXAMPLE 24

7β-[2-(2-Aminothiazol-4-yl)-(Z)-2-ethoxyiminoacetamido]-3-[[6-(2-hydroxyethylthio)imidazo[1,2-b]pyridazinium-1-yl]methyl]-3-cephem-4-carboxylate

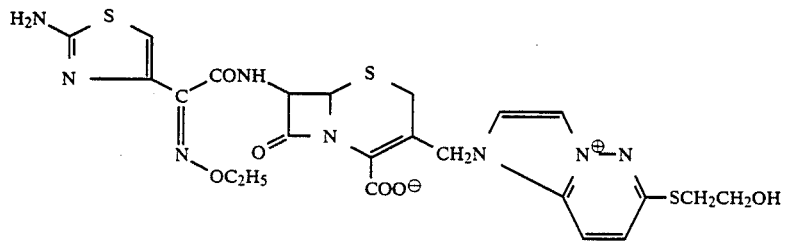

In 5 ml of dimethylformamide are dissolved 1.23 g of 7β-[2-(2-aminothiazol-4-yl)-(Z)-2-ethoxyiminoacetamido]-3-hydroxymethyl-3-cephem-4-carboxylic acid tri-n-butylamine salt and 1.4 g of 6-[2-(2-tetrahydropyranyloxy)ethylthio]imidazo[1,2-b]pyridazine and after the solution is cooled to −20° C., 1.2 g of ethyl o-phenylene phosphate is added. The mixture is stirred for 1.5 hours, with the temperature being gradually raised to 0° C. The reaction mixture is subjected to silica gel (100 g) column chromatography and after the column is washed with acetonitrile (600 ml) and acetonitrile-water (19:1, 400 ml; 9:1, 200 ml), elution is carried out with 700 ml of acetonitrile-water (4:1). The eluate is concentrated under reduced pressure and the residue is dissolved in 20 ml of dimethylformamide and re-chromatographed on a silica gel (80 g) column. After the column is washed with acetonitrile (500 ml) and acetonitrile-water (19:1, 400 ml; 9:1, 600 ml), elution is carried out with 300 ml of acetonitrile-water (4:1). The eluate is concentrated under reduced pressure to 5 ml and the residue is diluted with 5 ml of water and 7 ml of tetrahydrofuran. With ice-cooling and stirring, 4.5 ml of 1 N-hydrochloric acid is added dropwise thereto over 30 minutes, and the mixture is stirred at room temperature for 1 hour. Then, with ice-cooling, the mixture is adjusted to pH 5.0 with 1 N-aqueous sodium hydroxide solution and the tetrahydrofuran is distilled off under reduced pressure. The residual aqueous solution is subjected to XAD-II (80 ml) column chromatography. After the column is washed with 300 ml of water, 200 ml of 5% (v/v) ethanol and 150 ml of 10% (v/v) ethanol, elution is carried out with 600 ml of 10% (v/v) ethanol. The eluate is concentrated under reduced pressure and filtered and the filtrate is freeze-dried to give 245 mg of the title compound as light yellow powders.

IR (KBr) cm$^{-1}$: 3300, 1770, 1670, 1610.

NMR (D$_2$O+DCl) δ: 1.44 (3H, t, J=7 Hz), 3.63 (2H, t, J=6 Hz), 3.67 (2H, ABq, J=18 Hz), 4.10 (2H, t, J=6 Hz), 4.48 (2H, q, J=7 Hz), 5.47 (1H, d, J=5 Hz), 5.64 (2H, ABq, J=15 Hz), 6.02 (1H, d, J=5 Hz), 7.27 (1H, s), 7.85–8.6 (4H, m).

EXAMPLE 25

7β-[2-(2-Aminothiazol-4-yl)-(Z)-2-methoxyiminoacetamido]-3-[[6-(2-carbamoylaminoethylthio)imidazo-[1,2-b]pyridazinium-1-yl]methyl]-3-cephem-4-carboxylate

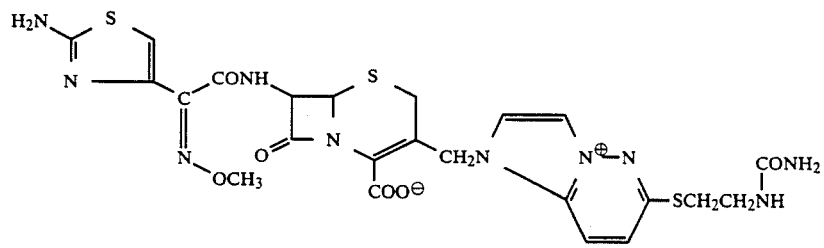

In 100 ml of dimethylformamide is dissolved 712 mg of 6-(2-carbamoylaminoethylthio)imidazo[1,2-b]pyridazine with warming. After cooling, 599 mg of 7β-[2-(2-aminothiazol-4-yl)-(Z)-2-methoxyiminoacetamido]-3-hydroxymethyl-3-cephem-4-carboxylic acid tri-n-butylamine salt is added. Then, at −10° C., 800 mg of ethyl o-phenylene phosphate is added and the mixture is stirred for 1 hour, with the temperature being gradually raised to 0° C. The reaction mixture is then concentrated under reduced pressure to 10 ml. The concentrate is subjected to silica gel (100 g) column chromatography and after the column is washed with acetonitrile, elution is carried out with acetonitrile-water (3:1). The eluate is concentrated under reduced pressure and the residue is subjected to XAD-II (150 ml) column chromatography. After the column is washed with water, elution is carried out with 20% (v/v) ethanol. The eluate is concentrated under reduced pressure and the residue is freeze-dried to give 100 mg of the title compound as yellow powders.

IR (KBr) cm$^{-1}$: 1765, 1660, 1610, 1530.

NMR (D$_2$O+DCl) δ: 3.4–4.1 (6H, m), 4.25 (3H, s), 5.33 (1H, d, J=5 Hz), 5.72 (2H, ABq, J=15 Hz), 6.05 (1H, d, J=5 Hz), 7.33 (1H, s), 7.96 (1H, d, J=10 Hz), 8.37 (1H, d, J=2 Hz), 8.55 (1H, d, J=2 Hz), 8.61 (1H, d, J=10 Hz).

EXAMPLE 26

7β-[2-(5-Amino-1,2,4-thiadiazol-3-yl)-(Z)-2-methoxyiminoacetamido]-3-[[6-(2-hydroxyethylthioo)imidazo[1,2-b]pyridazinium-1-yl]methyl]-3-cephem-4-carboxylate

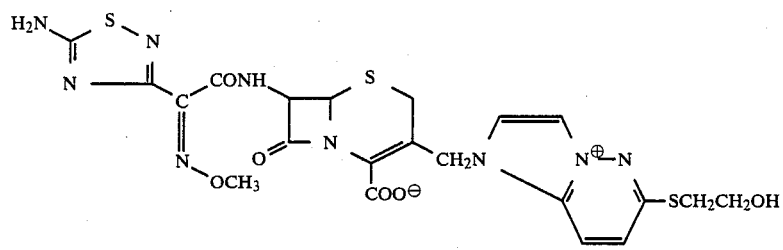

In 7 ml of dimethylformamide are dissolved 654 mg of sodium 7β-[2-(5-amino-1,2,4-thiadiazol-3-yl)-(Z)-2-methoxyiminoacetamido]-3-hydroxymethyl-3-cephem-4-carboxylate and 1.05 g of 6-[[2-(2-tetrahydropyranyloxy)ethylthio]imidazo[1,2-b]pyridazine, followed by addition of 3 g of sodium sulfate. Under cooling at −20° C. and stirring, 900 mg of ethyl o-phenylene phosphate is added dropwise and the mixture is stirred for 1.5 hours with the temperature being gradually raised to 0° C. The reaction mixture is subjected to silica gel (100 g) column chromatography and after the column is washed with acetonitrile (500 ml) and acetonitrile-water (19:1, 600 ml; 12:1, 600 ml; 9:1, 200 ml), elution is carried out with 1 liter of acetonitrile-water (17:3). The eluate is concentrated under reduced pressure to 30 ml and 20 ml of tetrahydrofuran is added to the residue. Then, with stirring at room temperature, 8 ml of 1 N-hydrochloric acid is added dropwise over 30 minutes. After completion of dropwise addition, the mixture is further stirred for 30 minutes, after which it is adjusted to pH 5.0 with 1 N-aqueous sodium hydroxide solution under ice-cooling. The tetrahydrofuran is distilled off under reduced pressure and the residual solution is subjected to XAD-II (80 ml) column chromatography. After the column is washed with 500 ml of water and 70 ml of 5% (v/v) ethanol, elution is carried out with 500 ml of 10% (v/v) ethanol. The eluate is concentrated under reduced pressure and filtered and the filtrate is freeze-dried to give 385 mg of the title compound as light yellow powders.

IR (KBr) cm$^{-1}$: 3350, 1770, 1670, 1610.

NMR (D$_2$O+CD$_3$CN) δ: 3.1–3.9 (4H, m), 4.07 (2H, t, J=5 Hz), 4.20 (3H, s), 5.33 (1H, d, J=5 Hz), 5.50 (2H, s), 5.98 (1H, d, J=5 Hz), 7.85–8.7 (4H, m).

EXAMPLE 27

7β-[2-(2-Aminothiazol-4-yl)-(Z)-2-methoxyiminoacetamido]-3-[[6-(3-hydroxypropylthio)imidazo[1,2-b]pyridazinium-1-yl]methyl]-3-cephem-4-carboxylate

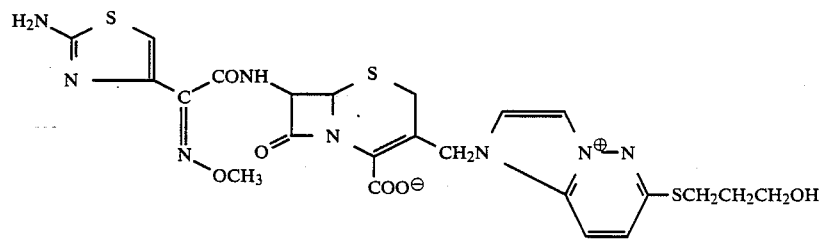

In the same manner as Example 24, the title compound is obtained as light yellow powders.

IR (KBr) cm$^{-1}$: 3300, 1770, 1670, 1610, 1530.

NMR (D$_2$O+CD$_3$CN) δ: 1.95–2.3 (2H, m), 3.42 (2H, ABq, J=17 Hz), 3.45 (2H, t, J=7 Hz), 3.84 (2H, t, J=6 Hz), 4.07 (3H, s), 5.32 (1H, d, J=5 Hz), 5.47 (2H, br.s), 5.91 (1H, d, J=5 Hz), 7.03 (1H, s), 7.7–8.7 (4H, m).

EXAMPLE 28

7β-[2-(2-Aminothiazol-4-yl)-(Z)-2-methoxyiminoacetamido]-3-[[6-(2-carbamoyloxyethylthio)imidazo[1,2-b]pyridazinium-1-yl]methyl]-3-cephem-4-carboxylate

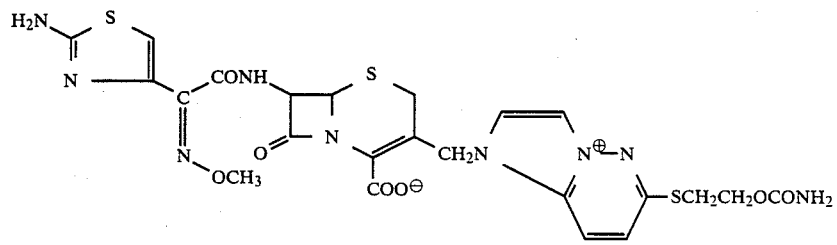

In 5 ml of dimethylformamide are dissolved 479 mg of 7β-[2-(2-aminothiazol-4-yl)-(Z)-2-methoxyiminoacetamido]-3-hydroxymethyl-3-cephem-4-carboxylic acid tri-n-butylamine salt and 600 mg of 6-[2-(N-chloroacetylcarbamoyloxy)ethylthio]imidazo[1,2-b]pyridazine, followed by addition of 1.5 g of sodium sulfate. Under cooling at −20° C. and stirring, 480 mg of ethyl o-phenylene Phosphate is added dropwise and the mixture is stirred for 1.5 hours with the temperature being gradually raised to 0° C. The reaction mixture is subjected to silica gel (100 g) column chromatography and after the column is washed with acetonitrile (500 ml) and acetonitrile-water (19:1, 600 ml; 9:1, 400 ml; 17:3, 400 ml), elution is carried out with 500 ml of acetonitrile-water (33:7). The eluate is concentrated to 50 ml under reduced pressure and 10 ml of tetrahydrofuran is added to the residue. With ice-cooling, 300 mg of sodium N-methyldithiocarbamate is added and the mixture is stirred under ice-cooling for 30 minutes. The tetrahydrofuran is distilled off under reduced pressure and the residual aqueous solution is washed with 20 ml of ethyl acetate. The water layer is subjected to XAD-II (80 ml) column chromatography and after the column is washed with 500 ml of water, 200 ml of 5% (v/v) ethanol, and 200 ml of 10% (v/v) ethanol, elution is carried In the same manner as Example 28, the title compound is obtained as light yellow powders.
IR (KBr) cm$^{-1}$: 3300, 1770, 1700, 1670, 1610.
NMR D$_2$O+CD$_3$CN) δ: 3.1–3.8 (4H, m), 4.06 (3H, s), 4.29 (2H, t, J=6 Hz), 5.33 (1H, d, J=5 Hz), 5.45 (2H, br.s), 5.90 (1H, d, J=5 Hz), 7.03 (1H, s), 7.81 (1H, d, J=10 Hz), 8.27 (1H, d, J=2 Hz), 8.42 (1H, d, J=2 Hz), 8.59 (1H, d, J=10 Hz).

EXAMPLE 30

7β-[2-(2-Aminothiazol-4-yl)-(Z)-2-ethoxyiminoacetamido]-3-[[6-(2-carbamoyloxyethylthio)imidazo[1,2-b]pyridazinium-1-yl]methyl]-3-cephem-4-carboxylate

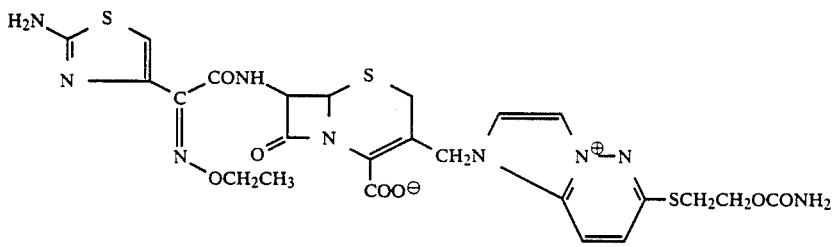

out with 15% (v/v) ethanol. The eluate is concentrated under reduced pressure and filtered, and the filtrate is freeze-dried to give 95 mg of the title compound as light yellow powders.
IR (KBr) cm$^{-1}$: 3350, 1770, 1710, 1660, 1600.
NMR (D$_2$O+CD$_3$CN) δ: 3.1–3.8 (4H, m), 4.06 (3H, s), 4.52 (2H, t, J=7 Hz), 5.32 (1H, d, J=5 Hz), 5.45 (2H, br.s), 5.90 (1H, d, J=5 Hz), 7.03 (1H, s), 7.85 (1H, d, J=10 Hz), 8.31 (1H, d, J=2 Hz), 8.45 (1H, d, J=2 Hz), 8.63 (1H, d, J=10 Hz).
Elemental analysis: C$_{23}$H$_{23}$N$_9$O$_7$S$_3$.2.5H$_2$O. Calcd. (%): C, 40.70; H, 4.16; N, 18.57. Found (%): C, 40.51; H, 3.89; N, 18.44.

EXAMPLE 29

7β-[2-(2-Aminothiazol-4-yl)-(Z)-2-methoxyiminoacetamido]-3-[[6-(3-carbamoyloxypropylthio)imidazo[1,2-b]pyridazinium-1-yl]methyl]-3-cephem-4-carboxylate In the same manner as Example 28, the title compound is obtained as light yellow powders.
IR (KBr) cm$^{-1}$: 3350, 1770, 1720, 1670, 1610.
NMR (D$_2$O+CD$_3$CN) δ: 1.40 (3H, t, J=6 Hz), 3.15–3.85 (4H, m), 4.38 (2H, q, J=6 Hz), 4.56 (2H, t, J=6 Hz), 5.40 (1H, d, J=5 Hz), 5.50 (2H, br.s), 5.96 (1H, d, J=5 Hz), 7.05 (1H, s), 7.89 (1H, d, J=10 Hz), 8.33 (1H, d, J=2 Hz), 8.49 (1H, d, J=2 Hz), 8.63 (1H, d, J=10 Hz).

EXAMPLE 31

7β-[2-(5-Amino-1,2,4-thiadiazol-3-yl)-(Z)-2-methoxyiminoacetamido]-3-[[6-(2-carbamoyloxyethylthio)imidazo[1,2-b]pyridazinium-1-yl]methyl]-3-cephem-4-carboxylate

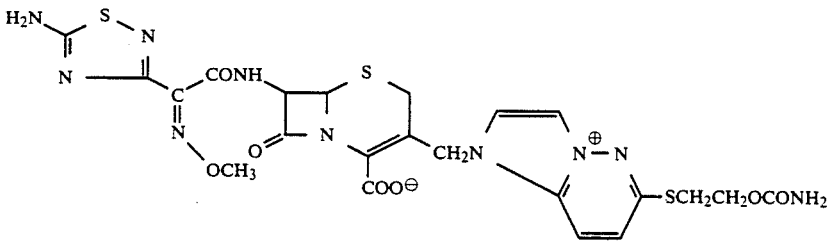

In 10 ml of dimethylformamide are dissolved 349 mg of sodium 7β-[2-(5-amino-1,2,4-thiadiazol-3-yl)-(Z)-2-methoxyiminoacetamido]-3-hydroxymethyl-3-cephem-4-carboxylate and 630 mg of 6-[2-(N-chloroacetylcar-

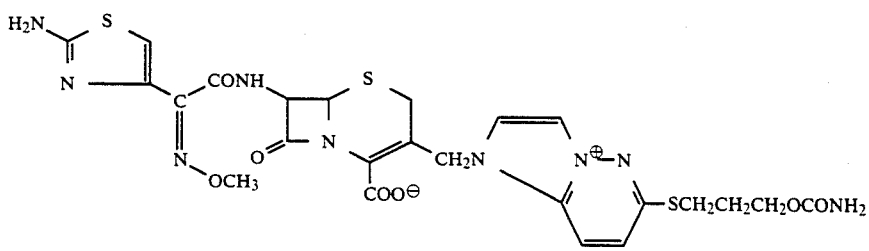

bamoyloxy)ethylthio]imidazo[1,2-b]pyridazine, followed by addition of 1.5 g of sodium sulfate. With stirring and cooling at −20° C., 480 mg of ethyl o-phenylene phosphate is added dropwise and the mixture is stirred for 1.5 hours with the temperature being gradually increased to 0° C. The reaction mixture is subjected to silica gel (100 g) column chromatography and after the column is washed with acetonitrile (500 ml) and acetonitrilewater (19:1, 400 ml; 9:1, 400 ml), elution is carried out with 400 ml of acetonitrile-water (17:3). The eluate is concentrated to 20 ml under reduced pressure and 10 ml of tetrahydrofuran is added. With ice-cooling, 258 mg of sodium N-methyldithiocarbamate is added and the mixture is stirred under ice-cooling for 20 minutes. The tetrahydrofuran is distilled off under reduced pressure and the residual aqueous solution is washed with 20 ml of ethyl acetate. The water layer is subjected to XAD-II (80 ml) column chromatography and after the column is washed with 300 ml of water and 200 ml of 5% (v/v) ethanol, elution is carried out with 300 ml of 10% (v/v) ethanol. The eluate is concentrated under reduced pressure and filtered and the filtrate is freeze-dried to give 140 mg of the title compound as light yellow powders.

IR (KBr) cm$^{-1}$: 3350, 1770, 1710, 1670, 1610.

NMR (D$_2$O+CD$_3$CN) δ: 3.42 (2H, ABq, J=18 Hz), 3.66 (2H, t, J=6 Hz), 4.13 (3H, s), 5.30 (1H, d, J=5 Hz), 5.44 (2H, br.s), 5.92 (1H, d, J=5 Hz), 7.85 (1H, d, J=10 Hz), 8.31 (1H, d, J=2 Hz), 8.43 (1H, d, J=2 Hz), 8.63 (1H, d, J=10 Hz).

EXAMPLE 32

7β-[2-(2-Aminothiazol-4-yl)-(Z)-2-methoxyiminoacetamido]-3-[[6-(2-acetylaminoethylthio)imidazo[1,2-b]pyridazinium-1-yl]methyl]-3-cephem-4-carboxylate

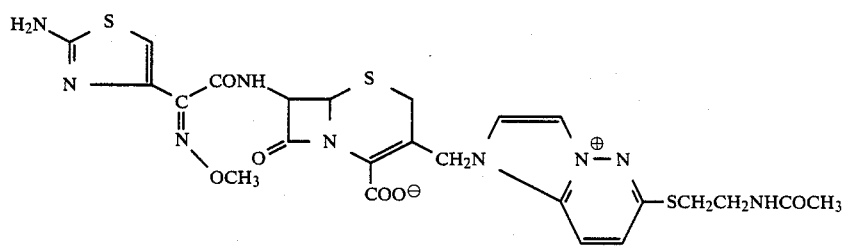

To 35 ml of dichloromethane are added 599 mg of 7β-[2-(2-aminothiazol-4-yl)-(Z)-2-methoxyiminoacetamido]-3-hydroxymethyl-3-cephem-4-carboxylic acid tri-n-butylamine salt and 709 mg of 6-(2-acetylaminoethylthio)imidazo[1,2-b]pyridazine and under cooling at −30° C., 697 mg of 2-phenyl-2-oxo-1,3,2-benzodioxaphosphole is added. The mixture is stirred for 2 hours with the temperature being gradually raised to 5° C. The solvent is then distilled off under reduced pressure and the residue is subjected to silica gel (100 g) column chromatography, elution being carried out with acetonitrile-water (6:1, 5:1 and 4:1). The fractions rich in the desired compound are pooled and concentrated under reduced pressure. The residue is subjected to XAD-II (100 ml) column chromatography and after the column is washed with water, elution is carried out with 10% (v/v) ethanol. The eluate is concentrated under reduced pressure and freeze-dried to give 68 mg of the title compound as light yellow powders.

IR (KBr) cm$^{-1}$: 3420, 1770, 1660, 1640, 1610.

NMR (D$_2$O) δ: 2.05 (3H, s), 3.1–3.85 (6H, m), 4.04 (3H, s), 5.32 (1H, d, J=4.5 Hz), 5.43 (2H, s), 5.87 (1H, d, J=4.5 Hz), 6.95 (1H, s), 7.77 (1H, d, J=10 Hz), 8.24 (1H, d, J=1.5 Hz), 8.39 (1H, d, J=1.5 Hz), 8.53 (1H, d, J=10 Hz).

Elemental analysis: C$_{24}$H$_{25}$N$_9$O$_6$S$_3$·2.5H$_2$). Calcd. (%): C, 42.60; H, 4.47; N, 18.63. Found (%): C, 42.35; H, 4.31; N, 18.54.

EXAMPLE 33

7β-[2-(2-Aminothiazol-4-yl)-(Z)-2-methoxyiminoacetamido]-3-[[6-(2-formylaminoethylthio)imidazo[1,2-b]pyridazinium-1-yl]methyl]-3-cephem-4-carboxylate

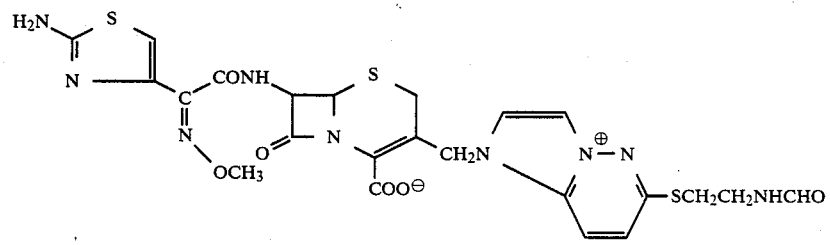

In the same manner as Example 32, the title compound is obtained as light yellow powders.

IR (KBr) cm$^{-1}$: 1770, 1660, 1610, 1530.

NMR (D$_2$O+CD$_3$CN) δ: 3.0–3.85 (6H, m), 4.02 (3H, s), 5.28 (1H, d, J=5 Hz), 5.42 (2H, s), 5.86 (1H, d, J=5 Hz), 6.98 (1H, s), 7.79 (1H, d, J=10 Hz), 8.18 (1H, s), 8.27 (1H, d, J=2 Hz), 8.41 (1H, d, J=2 Hz), 8.58 (1H, d, J=10 Hz).

EXAMPLE 34

7β-[2-(2-Aminothiazol-4-yl)-(Z)-2-hydroxyiminoacetamido]-3-[[6-(2-carbamoyloxyethylthio)imidazo[1,2-b]pyridazinium-1-yl]methyl]-3-cephem-4-carboxylate

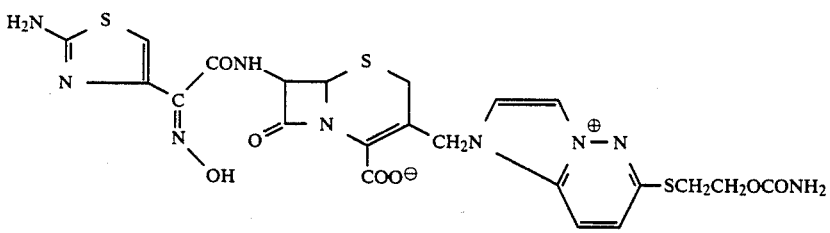

In 10 ml of dimethylformamide are dissolved 400 mg of sodium 7β-[2-(2-tritylaminothiazol-4-yl)-(Z)-2-(trityloxyimino)acetamido]-3-hydroxymethyl-3-cephem-4-carboxylate and 417 mg of 6-[2-(N-chloroacetylcarbamoyloxy)ethylthio]imidazo[1,2-b]pyridazine and while the solution is stirred under cooling at −20° C., 354 mg of o-phenylene phosphate is added dropwise. The mixture is stirred for 1.5 hours, with the temperature being gradually increased to 0° C. The reaction mixture is subjected to silica gel (100 g) column chromatography and after the column is washed with acetonitrile (500 ml) and acetonitrile-water (19:1, 400 ml; 37:3, 400 ml), elution is carried out with 400 ml of acetonitrile-water (17:3). The eluate is concentrated under reduced pressure and freeze-dried and the resulting light yellow powders are suspended in 10 ml of dichloromethane. While the mixture is stirred at room temperature, 3 ml of 99% formic acid is added dropwise. The mixture is stirred at room temperature for 24 hours, after which it is concentrated under reduced pressure. The residue is dissolved in a mixture of 10 ml of water and 10 ml of tetrahydrofuran. Under ice-cooling, the solution is adjusted to pH 7.0 with 1N-aqueous sodium hydroxide solution, followed by addition of 200 mg of sodium N-methyldithiocarbamate. The mixture is stirred under ice-cooling for 30 minutes and, then, washed with 20 ml of ethyl acetate. The water layer is subjected to XAD-II (70 ml) column chromatography and after the column is washed with 200 ml of water, 100 ml of 2.5% (v/v) ethanol, 100 ml of 5% (v/v) ethanol and 50 ml of 10% (v/v) ethanol, elution is carried out with 300 ml of 15% (v/v) ethanol. The eluate is concentrated under reduced pressure and filtered. The filtrate is freeze-dried to give 18 mg of the title compound as light yellow powders.

IR (KBr) cm$^{-1}$: 3400, 1770, 1715, 1610.

NMR (D$_2$O+CD$_3$CN) δ: 3.1–3.8 (4H, m), 5.34 (1H, d, J=5 Hz), 5.46 (2H, br.s), 5.94 (1H, d, J=5 Hz), 7.01 (1H, s), 7.85 (1H, d, J=10 Hz), 8.30 (1H, d, J=2 Hz), 8.44 (1H, d, J=2 Hz), 8.63 (1H, d, J=10 Hz).

EXAMPLE 35

7β-[2-(2-Aminothiazol-4-yl)-(Z)-2-allyloxyiminoacetamido]-3-[[5-(2-aminoethylthio)imidazo[1,2-a]pyridinium-1-yl]methyl]-3-cephem-4-carboxylate hydrochloride

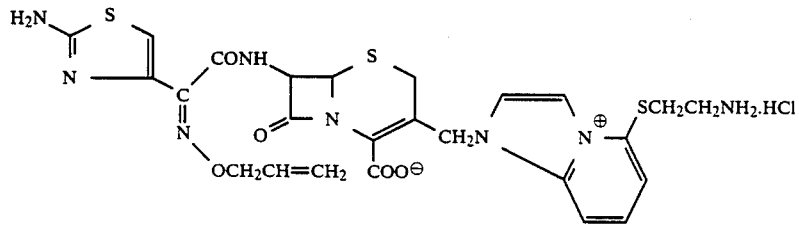

In the same manner as Example 16, the title compound is obtained as colorless powders.

IR (KBr) cm$^{-1}$: 3350, 3100, 1770, 1630, 1530.

NMR (D$_2$O+DCl) δ: 3.3–3.7 (6H, m), 5.2–5.8 (5H, m), 6.96 (1H, d, J=5 Hz), 5.95–6.4 (1H, m), 7.24 (1H, s), 7.75–8.5 (5H, m).

EXAMPLE 36

7β-[2-(2-Aminothiazol-4-yl)-(Z)-2-ethoxyiminoacetamido]-3-[[5-(2-(N-acetimidoylamino)ethylthio]imidazo[1,2-a]pyridinium-1-yl]methyl]-3-cephem-4-carboxylate hydrochloride

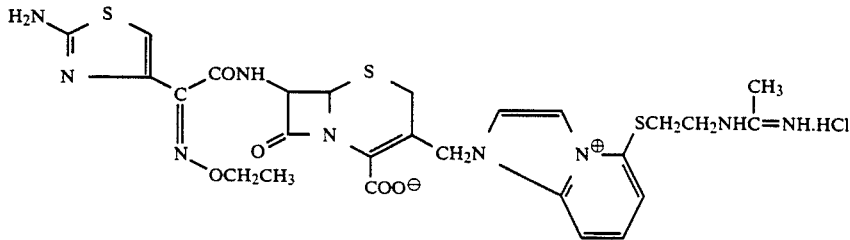

In the same manner as Example 22, 7β-[2-(2-aminothiazol-4-yl)-(Z)-2-ethoxyiminoacetamido]-3-[[5-(2-aminoethylthio)imidazo[1,2-a]pyridinium-1-yl]methyl]-3-cephem-4-carboxylate hydrochloride is reacted with O-benzyl acetimidate hydrochloride at pH 8.5 and the reaction product is purified by XAD-II column chromatography to give the title compound as light yellow powders.

IR (KBr) cm$^{-1}$: 1770, 1630, 1530.

NMR (D₂O) δ: 1.38 (3H, t, J=7 Hz), 2.29 (3H, s), 3.2–3.85 (6H, m), 4.39 (2H, q, J=7 Hz), 5.33 (1H, d, J=5 Hz), 5.47 (2H, ABq), 5.92 (1H, d, J=5 Hz), 7.17 (1H, s), 7.7–7.9 (1H, m), 8.05–8.55 (4H, m).

EXAMPLE 37

7β-[2-(2-Aminothiazol-4-yl)-(Z)-2-methoxyiminoacetamido]-3-[[5-(3-hydroxypropylthio)imidazo[1,2-a]pyridinium-1-yl]methyl]-3-cephem-4-carboxylate

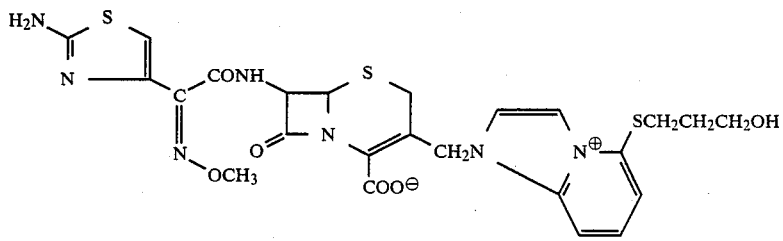

In the same manner as Example 24, the title compound is obtained as light yellow powders.

IR (KBr) cm⁻¹: 3300, 2930, 1770, 1670, 1610.

NMR (D₂O+CD₃CN) δ: 2.0–2.2 (2H, m), 3.40 (2H, ABq, J=16 Hz), 3.44 (2H, t, J=7 Hz), 3.83 (2H, t, J=7 Hz), 4.06 (3H, s), 5.30 (1H, d, J=5 Hz), 5.45 (2H, br.s), 5.90 (1H, d, J=5 Hz), 7.01 (1H, s), 7.6–8.4 (5H, m).

EXAMPLE 38

7β-[2-(2-Aminothiazol-4-yl)-(Z)-2-methoxyiminoacetamido]-3-[[5-(2-carbamoyloxyethylthio)imidazo[1,2-a]pyridinium-1-yl]methyl]-3-cephem-4-carboxylate IR (KBr) cm⁻¹: 3300, 3150, 1770, 1720, 1670, 1610.

NMR (D₂O+CD₃CN) δ: 3.40 (2H, ABq, J=17 Hz), 3.60 (2H, t, J=6 Hz), 4.05 (3H, s), 4.42 (2H, t, J=6 Hz), 5.30 (1H, d, J=5 Hz), 5.47 (2H, br.s), 5.89 (1H, d, J=5 Hz), 7.01 (1H, s), 7.75–8.45 (5H, m).

EXAMPLE 39

7β-[2-(2-Aminothiazol-4-yl)-(Z)-2-ethoxyiminoacetamido]-3-[[5-(2-carbamoyloxyethylthio)imidazo[1,2-a]pyridinium-1-yl]methyl]-3-cephem-4-carboxylate

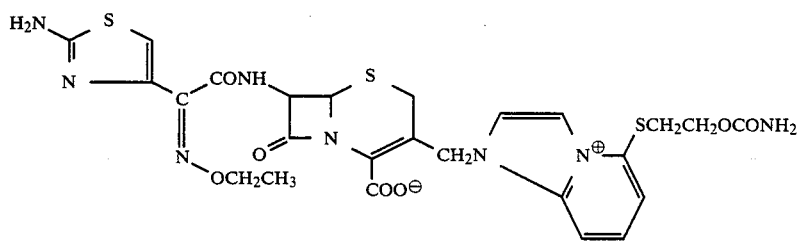

In the same manner as Example 28, the title compound is obtained as light yellow powders.

IR (KBr) cm⁻¹: 3350, 3150, 1765, 1715, 1660, 1610.

NMR (D₂O+CD₃CN) δ: 1.39 (3H, t, J=7 Hz), 3.43 (2H, ABq, J=18 Hz), 3.62 (2H, t, J=6 Hz), 4.35 (2H, q, J=7 Hz), 4.44 (2H, t, J=6 Hz), 5.34 (1H, d, J=5 Hz), 5.48 (2H, br.s), 5.91 (1H, d, J=5 Hz), 7.03 (1H, s), 7.75–8.5 (5H, m).

EXAMPLE 40

7β-[2-(2-Aminothiazol-4-yl)-(Z)-2-methoxyiminoacetamido]-3-[[5-(2-formylaminoethylthio)imidazo[1,2-a]pyridinium-1-yl]methyl]-3-cephem-4-carboxylate

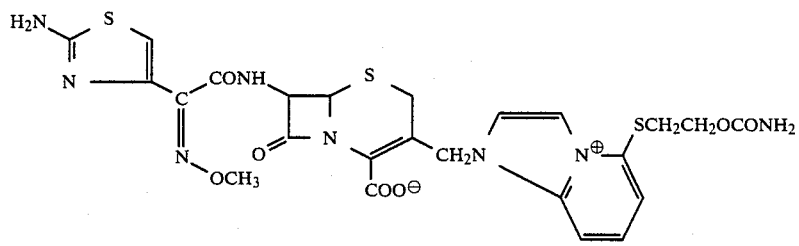

In the same manner as Example 28, the title compound is obtained as colorless powders.

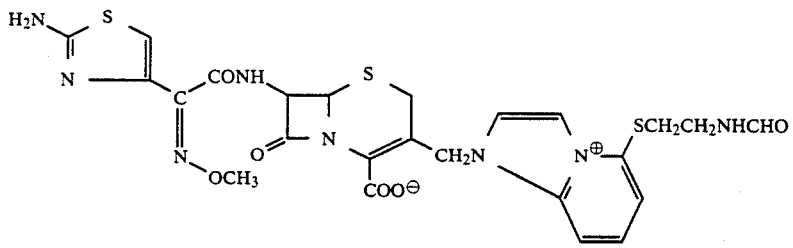

In the same manner as Example 32, the title compound is obtained as light yellow powders.
IR (KBr) cm$^{-1}$: 1765, 1665, 1625, 1610, 1530.
NMR (D$_2$O+CD$_3$CN) δ: 3.0–3.75 (6H, m), 4.02 (3H, s), 5.26 (1H, d, J=5 Hz), 5.41 (2H, s), 5.85 (1H, d, J=5 Hz), 6.98 (1H, s), 7.71 (1H, dd, J=2,6 Hz), 7.8–8.2 (3H, m), 8.26 (1H, d, J=2 Hz), 8.37 (1H, d, J=2 Hz).

EXAMPLE 41

7β-[2-(5-Amino-1,2,4-thiadiazol-3-yl)-(Z)-2-methoxyiminoacetamido]-3-[[6-(3-aminopropylamino)imidazo[1,2-b]pyridazinium-1-yl]methyl]-3-cephem-4-carboxylate hydrochloride

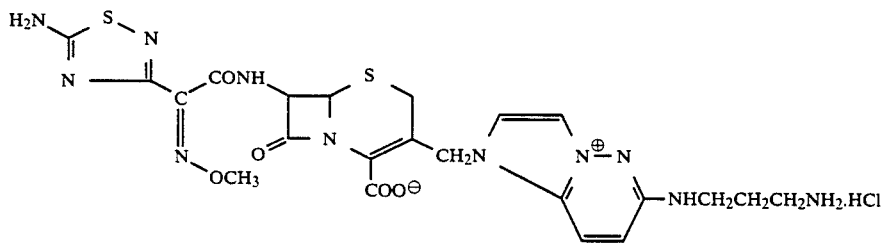

In the same manner as Example 12, the title compound is obtained as colorless powders.
IR (KBr) cm$^{-1}$: 1770, 1665, 1600.
NMR (D$_2$O) δ: 2.0–2.35 (2H, m), 3.1–3.85 (6H, m), 4.16 (3H, s), 5.38 (1H, d, J=5 Hz), 5.41 (2H, s), 5.98 (1H, d, J=5 Hz), 7.35 (1H, d, J=10 Hz), 8.00 (1H, d, J=2 Hz), 8.08 (1H, d, J=2 Hz), 8.22 (1H, d, J=10 Hz).

EXAMPLE 42

7β-[2-(2-Aminothiazol-4-yl)-(Z)-2-methoxyiminoacetamido]-3-[[6-(3-aminopropylamino)imidazo[1,2-b]pyridazinium-1-yl]methyl]-3-cephem-4-carboxylate hydrochloride

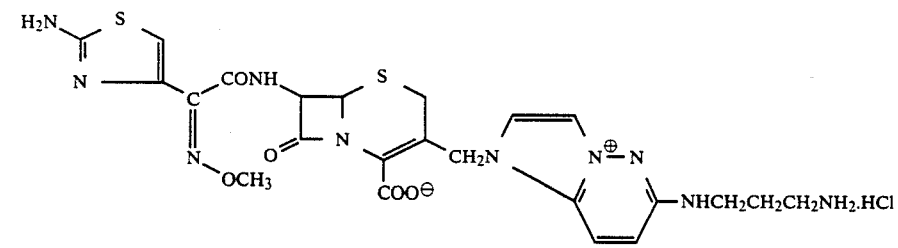

In the same manner as Example 11, the title compound is obtained as colorless powders.
IR (KBr) cm$^{-1}$: 1770, 1660, 1595.
NMR (D$_2$O) δ: 1.95–2.35 (2H, m), 3.05–3.85 (6H, m), 4.09 (3H, s), 5.32 (1H, d, J=5 Hz), 5.35 (2H, s), 5.88 (1H, d, J=5 Hz), 7.08 (1H, s), 7.31 (1H, d, J=10 Hz), 7.98 (1H, d, J=2 Hz), 8.06 (1H, d, J=2 Hz), 8.21 (1H, d, J=10 Hz).

EXAMPLE 43

7β-[2-(2-Aminothiazol-4-yl)-(Z)-2-ethoxyiminoacetamido]-3-[[6-(3-aminopropylamino)imidazo[1,2-b]pyridazinium-1-yl]methyl]-3-cephem-4-carboxylate hydrochloride

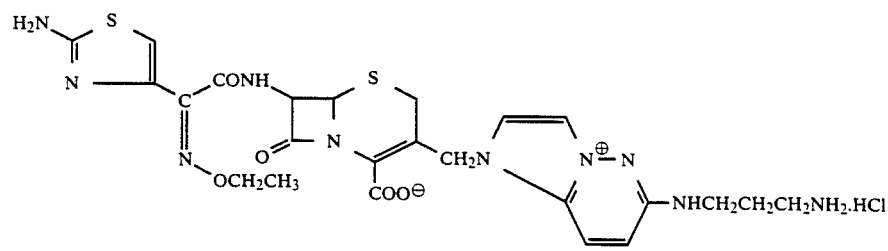

In the same manner as Example 11, the title compound is obtained as colorless powders.

IR (KBr) cm$^{-1}$: 1770, 1655, 1595.

NMR (D$_2$O) δ: 1.36 (3H, t, J=7 Hz), 1.95–2.35 (2H, m), 3.05–3.8 (6H, m), 4.34 (2H, q, J=7 Hz), 5.32 (1H, d, J=5 Hz), 5.33 (2H, s), 5.89 (1H, d, J=5 Hz), 7.05 (1H, s), 7.29 (1H, d, J=10 Hz), 7.97 (1H, d, J=2 Hz), 8.05 (1H, d, J=2 Hz), 8.20 (1H, d, J=10 Hz).

EXAMPLE 44

7β-[2-(2-Aminothiazol-4-yl)-(Z)-2-methoxyiminoacetamido]-3-[[5-(3-aminopropylamino)imidazo[1,2-a]pyridinium-1-yl]methyl]-3-cephem-4-carboxylate hydrochloride In the same manner as Example 14, the title compound is obtained as colorless powders IR (KBr) cm$^{-1}$: 1770, 1650, 1590, 1535.

NMR (D$_2$O) δ: 1.35 (3H, t, J=7 Hz), 2.0–2.4 (2H, m), 3.1–3.8 (6H, m), 4.33 (2H, q, J=7 Hz), 5.29 (1H, d, J=4.5 Hz), 5.31 (2H, s), 5.87 (1H, d, J=4.5 Hz), 6.65 (1H, d, J=8 Hz), 7.04 (1H, s), 7.28 (1H, d, J=8.5 Hz), 7.8–8.15 (3H, m).

EXAMPLE 46

7β-[2-(5-Amino-1,2,4-thiadiazol-3-yl)-(Z)-2-methoxyiminoacetamido]-3-[[5-(3-aminopropylamino)imidazo[1,2-a]pyridinium-1-yl]methyl]-3-cephem-4-carboxylate hydrochloride

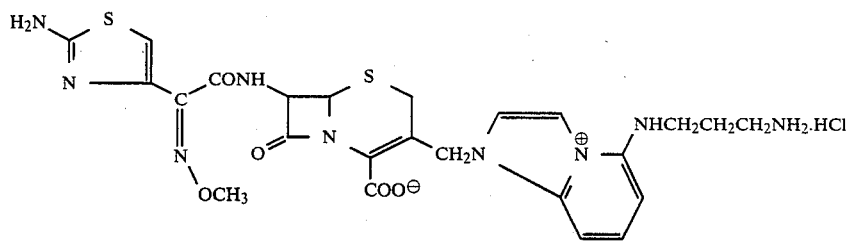

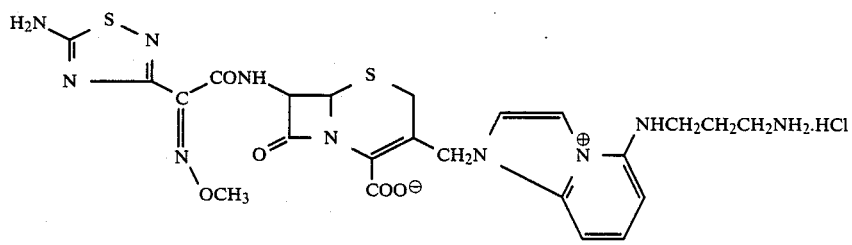

In the same manner as Example 13, the title compound is obtained as colorless powders.

IR (KBr) cm$^{-1}$: 1765, 1645, 1585.

NMR (D$_2$O) δ: 2.0–2.4 (2H, m), 3.05–3.8 (6H, m), 4.04 (3H, s), 5.26 (1H, d, J=5 Hz), 5.27 (2H, ABq, J=15 Hz), 5.84 (1H, d, J=5 Hz), 6.62 (1H, d, J=8.5 Hz), 6.98 (1H, s), 7.28 (1H, d, J=9 Hz), 7.8–8.1 (3H, m).

EXAMPLE 45

7β-[2-(2-Aminothiazol-4-yl)-(Z)-2-ethoxyiminoacetamido]-3-[[5-(3-aminopropylamino)imidazo[1,2-a]pyridinium-1-yl]methyl]-3-cephem-4-carboxylate hydrochloride In the same manner as Example 15, the title compound is obtained as colorless powders.

IR (KBr) cm$^{-1}$: 1770, 1645, 1590, 1525.

NMR (D$_2$O) δ: 2.0–2.4 (2H, m), 3.1–3.8 (6H, m), 4.09 (3H, s), 5.26 (1H, d, J=4.5 Hz), 5.28 (2H, s), 5.88 (1H, d, J=4.5 Hz), 6.59 (1H, d, J=8 Hz), 7.24 (1H, d, J=9 Hz), 7.8–8.1 (3H, m).

EXAMPLE 47

7β-[2-(2-Aminothiazol-4-yl)-(Z)-2-allyloxyiminoacetamido]-3-[[6-(2-aminoethylamino)imidazo[1,2-b]pyridazinium-1-yl]methyl]-3-cephem-4-carboxylate hydrochloride

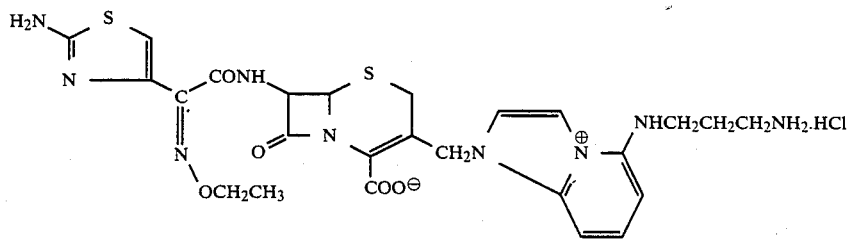

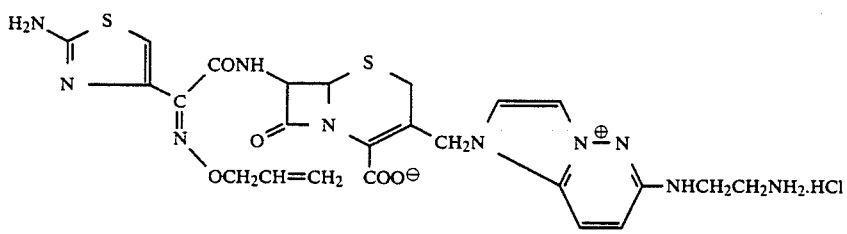

In the same manner as Example 11, the title compound is obtained as colorless powders.

IR (KBr) cm$^{-1}$: 3100, 1770, 1595.

NMR (D$_2$O+DCl) δ: 3.3–4.2 (6H, m), 5.2–5.75 (5H, m), 5.97 (1H, d, J=5 Hz), 6.0–6.4 (1H, m), 7.26 (1H, s), 7.35–8.35 (4H, m).

EXAMPLE 48

7β-[2-(2-Aminothiazol-4-yl)-(Z)-2-ethoxyiminoacetamido]-3-[[6-[2-(N-acetimidoylamino)ethylamino]imidazo[1,2-b]pyridazinium-1-yl]methyl]-3-cephem-4-carboxylate hydrochloride

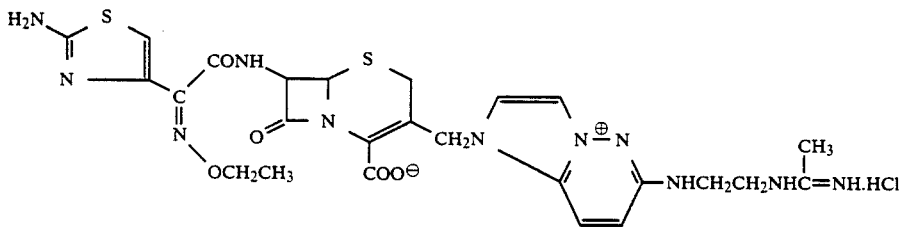

In the same manner as Example 22, 7β-2-(2-aminothiazol-4-yl)-(Z)-2-ethoxyiminoacetamido]-[[6-(2-aminoethylamino)imidazo[1,2-b]pyridazinium-1-yl]methyl]-3-cephem-4-carboxylate hydrochloride is reacted with O-benzyl acetimidate hydrochloride at pH 8.5 and the reaction product is purified by XAD-II column chromatography to give the title compound as colorless powders.

IR (KBr) cm$^{-1}$: 1770, 1625, 1600.

NMR (D$_2$O) δ: 1.37 (3H, t, J=7 Hz), 2.31 (3H, s), 3.49 (2H, ABq, J=18 Hz), 3.72 (4H, s), 4.37 (2H, q, J=7 Hz), 5.33 (1H, d, J=5 Hz), 5.36 (2H, s), 5.90 (1H, d, J=5 Hz), 7.11 (1H, s), 7.34 (1H, d, J=10 Hz), 8.01 (1H, d, J=2 Hz), 8.08 (1H, d, J=2 Hz), 8.25 (1H, d, J=10 Hz)

EXAMPLE 49

7β-[2-(2-aminothiazol-4-yl)-(Z)-2-ethoxyiminoacetamido]-3-[[5-(2-formylaminoethylthio)imidazo[1,2-a]pyridazinium-1-yl]methyl]-3-cephem-4-carboxylate

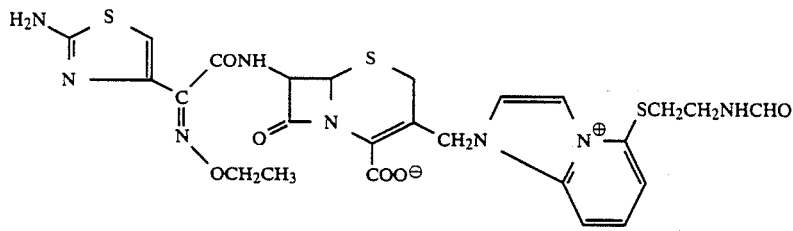

In the same manner as Example 32, the title compound is obtained as light yellow powders.

IR (KBr) cm$^{-1}$: 1770, 1660, 1625, 1610.

NMR (D$_2$O+CD$_3$CN) δ: 1.32 (3H, t, J=7Hz), 3.0–3.75 (6H, m), 4.28 (2H, q, J=7H$_z$), 5.27 (1H, d, J=5H$_z$), 5.41 (2H, s), 5.86 (1H, d, J=5H$_z$), 6.97 (1H, s), 7.71 (1H, dd, J=2, 6H=), 7.85–8.25 (3H, m), 8.25 (1H, d, J=2H$_z$), 8.37 (1H, d, J=2H$_z$).

Elemental analysis: C$_{25}$H$_{26}$N$_8$O$_6$S$_3$.2.5H$_2$O: Calcd.(%): C, 44.43; H, 4.62; N, 16.58. Found (%): C, 44.69; H, 4.52; N, 16.60.

EXAMPLE 50

7β-[2-(2-aminothiazol-4-yl)-(Z)-2-methoxyiminoacetamido]-3-[[6-(3-aminopropylthio)imidazo[1,2-b]pyridazinium-1-yl]methyl]-3-cephem-4-carboxylate.hydrochloride

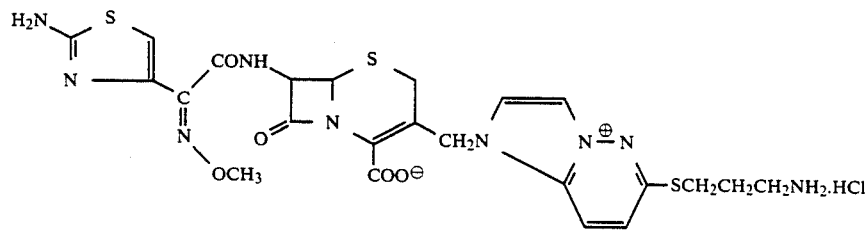

In the same manner as Example 16, the title oompound is obtained as light yellow powders.

IR (KBr) cm$^{-1}$: 1770, 1615, 1525.

NMR (D$_2$O+d$_6$-DMSO) δ: 2.1–2.45 (2H, m), 3.05–3.8 (6H, m), 4.05 (3H, s), 5.28 (1H, d, J=5H$_z$), 5.44 (2H, s, 5.88 (1H, d, J=5H$_z$), 7.02 (1H, s), 7.84 (1H, d, J=10H$_z$), 8.30 1H, d, J=2H$_z$), 8.47 (1H, d, J=2H$_z$), 8.59 (1H, d, J=10H$_z$).

EXAMPLE 51

7β-[2-(2-aminothiazol-4-yl)-(Z)-2-ethoxyiminoacetamido]-3-[[6-(3-aminopropylthio)imidazo[1,2-b]pyridazinium-1-yl]methyl]-3-cephem-4-carboxylate.hydrochloride

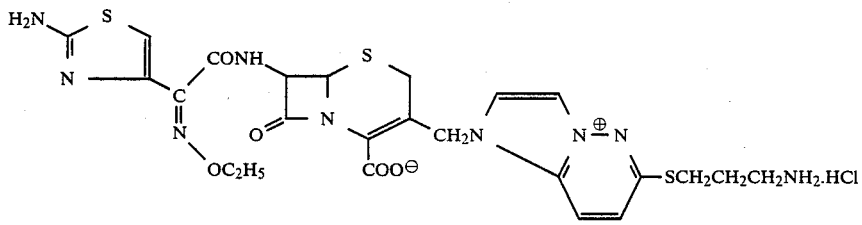

In the same manner as Example 16, the title compound is obtained as light yellow powders.

IR (KBr) cm$^{-1}$: 1770, 1615, 1525.

NMR (D$_2$O+d$_6$-DMSO) δ: 1.36 (3H, t, J=7H$_z$), 2.1–2.4 (2H, m), 3.0–3.75 (6H,m), 4.30 (2H, q, J=7H$_z$), 5.27 (1H, d, J=5H$_z$), 5.43 (2H, s , 5.88 (1H, d, J=5H$_z$), 6.98 (1H, s), 7.84 (1H, d, J=10H$_z$), 8.31 (1H, d, J=2H$_z$), 8.48 (1H, d, J=2H$_z$), 8.60 (1H, d, J=10H$_z$).

TEST EXAMPLE 1

The MIC (minimal inhibitory concentration) values of the compond prepared in Examples 8, 11, 16, 39 are shown below.

(a) Assay method

The MIC values of the test compound were determined by the agar dilution method. Thus, 1.0 ml aliquots of a series of dilutions prepared from a stock solution of the test compound are poured in Petri dishes and 9.0 ml aliquots of Trypticase soy agar are added to the dishes and mixed. A suspension of the test microorganism (about 10$^8$ CFU/ml) is smeared on each agar plate and incubated at 37° C. for 18 hours. The lowest concentration which causes a complete inhibition of growth of the test microorganism is designated as the minimal inhibitory concentration (MIC).

(b) Test microorganisms
 (1) *Staphylococcus aureus* 308 A-1
 (2) *Escherichia coli* 0-111
 (3) *Pseudomonas aeruginosa* P9
 (4) *Citrobacter freundii* TN 474
 (5) *Enterobacter cloacae* TN 583

(c) Results

The MIC (minimal inhibitory concentration) values of the test compounds (Examples 8, 16 and 39) are shown in Table 1.

The MIC values of the test compound (Example 11) are shown in Table 2.

TABLE 1

| | MIC value (mcg) | | |
|---|---|---|---|
| | Test compound (Example No.) | | |
| Test microorganism | 8 | 16 | 39 |
| (1) | 0.2 | 0.39 | 0.2 |
| (2) | <0.1 | <0.1 | <0.1 |
| (3) | 0.78 | 0.78 | 1.56 |

TABLE 2

| | MIC values (mcg) |
|---|---|
| | Test compound (Example No.) |
| Test microorganism | 11 |
| (1) | 0.39 |
| (2) | <0.1 |
| (3) | 0.78 |
| (4) | 0.78 |
| (5) | 0.78 |

What is claimed is:

1. A compound of the formula:

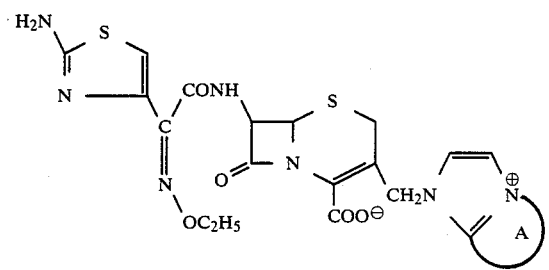

wherein ring A is a pyridine or pyridazine ring which is substituted at the ring constituting carbon atom by a group of the formula

—E—(CH$_2$)$_2$—NH$_2$ in which E is sulfur or NH, or a pharmaceutically acceptable salt thereof.

2. A compound as claimed in claim 1, wherein ring A is a pyridazine ring which is substituted at the ring-constituting carbon atom by a group of the formula:

—S—(CH$_2$)$_2$—NH$_2$.

3. A compound as claimed in claim 1, wherein ring A is a pyridine ring which is substituted at the ring-constituting carbon atom by a group of the formula:

—S—(CH$_2$)$_2$—NH$_2$.

4. A compound as claimed in claim 1, wherein E is NH.

5. A compound as claimed in claim 3, namely 7β-[2-(2-aminothiazol-4-yl)-(Z)-2-ethoxyiminoacetamido]-

3[[5-(2aminoethylthio)imidazo[1,2a]pyridinium-1-yl]methyl]-3-cephem-4-carboxylat or a pharmaceutically acceptable salt thereof.

6. A compound as claimed in claim 4, namely 7β-[2-(2-aminothiazol-4-yl)-(Z)-2-ethoxyiminoacetamido]-3-[[6-(2-aminoethylamino)imidazo[1,2-b]pyridazinium-1-yl]methyl]-3-cephem-4-carboxylate or a pharmaceutically acceptable salt thereof.

7. A compound as claimed in claim 2, namely 7β-[2-(2-aminothiazol-4-yl)-(Z)-2-ethyoxyiminoacetamido]-3-[[6-(2-aminoethylthio)imidazo[1,2-b]pyridazinium-1-yl]methyl]-3-cephem-4 -carboxylate or a pharmaceutically acceptable salt thereof.

8. A pharmaceutical composition containing an antibacterially effective amount of at least one of the compounds as claimed in claim 1, and a pharmaceutically acceptable excipient.

* * * * *